US007323490B2

(12) United States Patent
Lockhart et al.

(10) Patent No.: US 7,323,490 B2
(45) Date of Patent: Jan. 29, 2008

(54) PYRROLE COMPOUNDS AND USES THEREOF

(75) Inventors: David J. Lockhart, Del Mar, CA (US); Hitesh K. Patel, Encinitas, CA (US); Zdravko V. Milanov, San Diego, CA (US); Shamal Anil Mehta, San Diego, CA (US); Patrick Parvis Zarrinkar, San Diego, CA (US); William H. Biggs, III, San Clemente, CA (US); Pietro Ciceri, La Jolla, CA (US); Miles A. Fabian, La Jolla, CA (US); Daniel K. Treiber, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 506 days.

(21) Appl. No.: 10/848,584

(22) Filed: May 17, 2004

(65) Prior Publication Data

US 2004/0259880 A1 Dec. 23, 2004

Related U.S. Application Data

(60) Provisional application No. 60/471,425, filed on May 16, 2003, provisional application No. 60/480,289, filed on Jun. 20, 2003, provisional application No. 60/488,178, filed on Jul. 16, 2003, provisional application No. 60/488,172, filed on Jul. 16, 2003, provisional application No. 60/480,475, filed on Jun. 20, 2003, provisional application No. 60/516,610, filed on Oct. 30, 2003, provisional application No. 60/516,651, filed on Oct. 30, 2003, provisional application No. 60/516,616, filed on Oct. 30, 2003.

(51) Int. Cl.
*A61K 31/40* (2006.01)
*C07D 207/32* (2006.01)

(52) U.S. Cl. ............ 514/423; 514/427; 514/428; 514/429; 548/537; 548/561; 548/563

(58) Field of Classification Search ............ 514/427, 514/423; 548/561, 562, 563
See application file for complete search history.

(56) References Cited

U.S. PATENT DOCUMENTS

| | | | |
|---|---|---|---|
| 2,714,082 A | 7/1955 | Davies et al. | |
| 3,803,316 A | 4/1974 | Bosshard et al. | |
| 3,983,140 A | 9/1976 | Endo et al. | |
| 4,137,322 A | 1/1979 | Endo et al. | |
| 4,198,425 A | 4/1980 | Mitsui et al. | |
| 4,255,444 A | 3/1981 | Oka et al. | |
| 4,262,013 A | 4/1981 | Mistui et al. | |
| 4,375,475 A | 3/1983 | Willard et al. | |
| 4,572,909 A | 2/1986 | Campbell et al. | |
| 4,596,821 A | 6/1986 | Cragoe, Jr. et al. | |
| 4,604,403 A | 8/1986 | Cragoe, Jr. et al. | |
| 4,605,663 A | 8/1986 | Cragoe, Jr. et al. | |
| 4,605,664 A | 8/1986 | Cragoe, Jr. et al. | |
| 4,647,576 A | 3/1987 | Hoefle et al. | |
| 4,681,893 A | 7/1987 | Roth | |
| 4,879,303 A | 11/1989 | Davison et al. | |
| 5,003,080 A | 3/1991 | Butler et al. | |
| 5,089,514 A | 2/1992 | Hulin | |
| 5,097,045 A | 3/1992 | Butler et al. | |
| 5,103,024 A | 4/1992 | Millar et al. | |
| 5,124,482 A | 6/1992 | Butler et al. | |
| 5,149,837 A | 9/1992 | Butler et al. | |
| 5,155,251 A | 10/1992 | Butler et al. | |
| 5,216,174 A | 6/1993 | Butler et al. | |
| 5,245,047 A | 9/1993 | Butler et al. | |
| 5,248,793 A | 9/1993 | Millar et al. | |
| 5,260,305 A | 11/1993 | Dennick | |
| 5,273,995 A | 12/1993 | Roth | |
| 5,280,126 A | 1/1994 | Butler et al. | |
| 5,298,627 A | 3/1994 | Butler et al. | |
| 5,306,726 A | 4/1994 | Hulin | |
| 5,342,952 A | 8/1994 | Butler et al. | |
| 5,397,792 A | 3/1995 | Butler et al. | |
| 5,656,644 A | 8/1997 | Adams et al. | |
| 5,686,104 A * | 11/1997 | Mills et al. | 424/451 |
| 5,969,156 A | 10/1999 | Briggs | |

(Continued)

FOREIGN PATENT DOCUMENTS

EP 0160891 11/1985

(Continued)

OTHER PUBLICATIONS

Ostrum, Kenneth G., Science IP The CAS Search Service, Apr. 4, 2005, 1-30, Columbus, OH.

Stanley, Kerry G., Science IP The CAS Search Service, Apr. 8, 2005, 1-33, Columbus, OH.

Bruce D. Roth, The Discovery and Development of Atorvastatin, a Potent Novel Hypolipidemic Agent, Progress in Medical Chemistry, 2002, pp. 1-22, vol. 40.

Peter W.K. Woo, Atorvastatin, An HMG-COA Reductase Inhibitor and Effective Lipid-Regulating Agent Part III Synthesis of [$^2$H$_3$] [$^{13}$C$_8$], And [$^{13}$C$_7$, $^{15}$N] Atorvastatin And Their Application in Metabolic And Pharmacokinetic Studies, Journal of Labelled Compounds and Radiopharmaceuticals, 1999, pp. 135-145, vol. 42.

(Continued)

*Primary Examiner*—Rebecca Anderson
*Assistant Examiner*—Yong Chu
(74) *Attorney, Agent, or Firm*—Jones Day

(57) ABSTRACT

The invention provides pyrrole-containing compounds and methods of use thereof. Kits and pharmaceutical compositions comprising the pyrrole compounds of the invention are also provided. The compounds and compositions disclosed herein are preferably used in the treatment of neurodegenerative diseases, cardiovascular diseases, proliferative diseases, and visual disorders. In particular, methods and compositions for the treatment of stroke are disclosed herein.

16 Claims, 40 Drawing Sheets

U.S. PATENT DOCUMENTS

| | | | |
|---|---|---|---|
| 5,985,884 | A | 11/1999 | Lohray et al. |
| 6,048,883 | A | 4/2000 | Haigh et al. |
| 6,054,453 | A | 4/2000 | Lohray et al. |
| 6,126,971 | A | 10/2000 | Mills et al. |
| 6,130,214 | A | 10/2000 | Lohray et al. |
| 6,166,049 | A | 12/2000 | Smith |
| 6,274,603 | B1 | 8/2001 | Poirier |
| 6,440,966 | B1 | 8/2002 | Barrett et al. |
| 6,455,574 | B1 | 9/2002 | Buch |
| 6,541,636 | B2 | 4/2003 | Harada et al. |
| 2003/0186221 | A1 | 10/2003 | Lockahart |
| 2003/0199498 | A1 | 10/2003 | Lohray et al. |
| 2003/0236254 | A1 | 12/2003 | Lohray et al. |
| 2004/0009470 | A1 | 1/2004 | Lockhart |
| 2004/0072893 | A1 | 4/2004 | Srinath et al. |
| 2005/0014954 | A1 | 1/2005 | Ohrlein et al. |
| 2005/0043357 | A1 | 2/2005 | Coleman et al. |

FOREIGN PATENT DOCUMENTS

| | | |
|---|---|---|
| EP | 0657426 | 6/1995 |
| EP | 1176140 | 12/2004 |
| WO | WO97/10217 | 3/1997 |
| WO | WO 03/027069 | 4/2003 |
| WO | WO03/086379 | 4/2003 |
| WO | WO 03/055479 | 7/2003 |
| WO | WO 03/057669 | 7/2003 |
| WO | WO 03/064411 | 8/2003 |
| WO | WO 03/082816 | 10/2003 |

OTHER PUBLICATIONS

Kebin Wu, Catalytic Properties of NAD(P) H : Quinone Oxidoreductase-2 (NQO2), a Dihydronicotinamide Riboside Dependent Oxidoreductase, 1997, pp. 221-228, vol. 347, No. 2 Article No. BB970344.

Paul R Graves, Discovery of Novel Targets of Quinoline Drugs in the Human Purine Binding Proteome, Molecular Pharmacology, pp. 1364-1372, vol. 62, No. 6.

Terry A Cook, The δ Subunit of Type 6 Phosphodiesterase Reduces Light-induced cGMP Hydrolysis in Rod Outer Segments, The Journal of Biological Chemistry, 2001, pp. 5248-5254, vol. 276, No. 7.

Vanessa Nancy, The δ Subunit of Retinal Rod cGMP Phosphodiesterase Regulates the Membrane Association of Ras and Rap GTPases, The Journal of Biological Chemistry, 2002, pp. 15076-15084, vol. 277, No. 17.

Houbin Zhang et al., Photoreceptor cGMP Phosphodiesterase δ Subunit (PDEδ) Functions as a Prenyl-binding Protein, The Journal of Biological Chemistry, 2004, pp. 407-413, vol. 279, No. 1.

Christine E. Foster, Structures of Mammalian Cytosolic Quinone Reductase, Free Radical Biology & Medicine, 2000, pp. 241-245, vol. 29, Nos. 3/4.

Krisztian J. Kapinya, Role of NAD(P)H:quinone oxidoreductase in the progression of neuronal cell death in vitro and the following cerebral ischaemia in vivo, Journal of Neurochemistry, 2003, pp. 1028-1039, vol. 84.

Ahlke Strassburg, Differential Gene Expression of NAD(P)H: Quinone Oxidoreductase and NRH: Quinone Oxidoreductase in Human Hepatocellular and Biliary Tissue, Molecular Pharmacology, 2002, pp. 32-325, vol. 61, No. 2.

Shiuan Chen, Structure-Function Studies of DT-Diaphorase (NQ01) And NRH: Quinone Oxidoreductase (NQO2), Free Radical Biology & Medicine, 2000, pp. 276-284, vol. 29, Nos. 3/4.

Richard J. Knox, Bioactivation of 5-(Aziridin-1-yl)-2,4-dinitrobenzamide (CB 1954) by Human NAD(P)H Quinone Oxidoreductase 2: A Novel Co-substrate-mediated Antitumor Prodrug Therapy, 2000, pp. 4179-4186, vol. 60.

Delwin J. Long, NRH: quinone Oxidoreductase (NQO2), Chemical Biological Interactionns, 2000, pp. 99-112, vol. 129.

Christine E. Foster et al., Crystal Structure of Human Quinone Type 2, a Metalloflavoprotein, Biochemistry, 1999, pp. 9881-9886, vol. 38.

Serge N. Schiffmann et al., Impaired Motor Coordination and Purkinje cell excitability in mice lacking calretinin, Proc. Natl. Acad., pp. 5257-5262, vol. 96.

Masao Takemoto, Pleiotropic Effects of 3-Hydroxy-3 Methylglutaryl Coenzyme A Reductase Inhibitors, Arterioscler Thromb Vasc Biol, 2001, pp. 1712-1719.

James K. Liao, Beyond Lipid Lowering: The Role of Statins in Vascular Protection, International Journal of Cardiology, 2002, pp. 1-18, vol. 86.

James K. Liao, Isoprenoid As Mediators of the Biological Effects of Statins, The Journal of Clinical Investigation, 2002, pp. 285-288, vol. 110, No. 3.

Carl J. Vaughan, MD, Prevention of Stroke and Dementia With Statins: Effects Beyond Lipid Lowering, Am J. Cardiol, 2003, pp. 23B-29B.

Zhi Jun Zhang, A Selective Decrease in the Relative Density of Parvalbumin-immunoreactive Neurons in the hippocampus in Schizophrenia, Schizophrenia Research, 2002, pp. 1-10, vol. 55.

Jun-Ho Maeng, Ph.D., Trip Report: CU-Array Biopharma Symposium on Medicinal and Synthetic Organic Chemistry, 2001, pp. 1-10, vol. 6, No. 33.

Olivier Nosjean, Identification of the Melatonin-binding Site $MT_3$ as the Quinone Reductase 2, The Journal of Biological Chemistry, 2000, pp. 31311-31317, vol. 275, No. 4.

Olivier Nosjean, Comparative Pharmacological Studies of Melatonin Receptors: MT1, MT2 and MT3/QR2. Tissue distribution of MT3/QR2, Biochemical Pharmacology, 2001, pp. 1369-1379, vol. 61.

Paula A Witt-Enderby, Melatonin Receptors and Their Regulation: Biochemical and Structural Mechanism, Life Sciences, 2003, pp. 2183-2198, vol. 72.

Shoji Harada, An Association between Idiopathic Parkinson's Disease and Polymorphisms of Phase II Detoxification Enzymes: Glutathione S- Transferase M1 and Quinone Oxidoreductase 1 and 2, Biochemical and Biophysical Research Communication, 2001, pp. 887-892, vol. 288.

Louis Renault et al., Co-expression, Copurification,crystallization and preliminary X-ray Analysis of a complex of ARL2-GTP and PDE δ, Crystallization papers, ISSN 0907-4449, 2001, pp. 1167-1170, Section D.

Pramod S. Pandey, An Efficient Synthesis of N3,4-dipheny-5-(4-fluorophenyl)-2-isopropyl-1H-3-pyrrolecarbonxamide, a key intermediate for atorvastatin synthesis, Bioorganic Medicinal Chemistry letters, 2004, pp. 129-131, vol. 14.

Katarzyna Billing Marczak et al, AP2-like cis Element is Required for Calretinin Gene Promoter Activity in Cells of Neuronal Phenotype Differentiated from Multipotent Human Cell Line DEV, 2002, pp. 412-420, vol. 1577.

Terry A. Cook, Binding of the Delta Subunit to Rod Phosphodiesterase Catalytic Subunits Required Methylated, Prenylated C- Termini of the Catalytic Subunits, Biochemistry, 2000, pp. 13516-13523, vol. 39.

Bettina. Lorenza, Cloning and gene Structure of the Rod CGMP Phosphodiesterase Delta Subunit Gene (PDED) in man and Mouse, European Journal of Human Genetics, 1998, pp. 283-290, vol. 6.

Anne-Marie Marzesco, The Rod cGMP Phosphodiestrase δ Subunit Dissociated the Small GTPase Rab13 from Membranes, The Journal of Biological Chemistry, 1998, pp. 22340-22345, vol. 273, No. 35.

Michael Hanzal Bayer, The Complex of Arl2-GTP and PDEδ: from Structure of function, The EMBO Journal, pp. 2095-2106, vol. 21, No. 9.

Krystyna R. Isaacs et al., Calretinin-Immunoreactive Dopaminergic Neurons from Embryonic Rat Mecencephalon Are Resistant to Levodopa-Induced Neurotoxicity, Experimental neurological, 1997, pp. 25-32.

G. Leuba et al., Quantitative Distribution of Parvalbumin, Calretinin, and Calbindin D-28k Immunoreactive Neurons in the Visual Cortex of Normal and Alzheimer Cases, Experimental Neurology, 1998, pp. 278-291, vol. 152.

Ning Li et al., Expression and Characterization of human PDEδ and its Caenorhabdits Elegans Ortholog CEδ, FEBS Letters, 1998, pp. 454-457, vol. 440.

Marco Linari, The Delta Subunit of Rod Specific Cyclic GMP phosphodiesterase, PDE δ, interacts with the Ard-like protein Arl3 in a GTP specific manner, FEBS Letters, pp. 55-59, vol. 458.

Akira Kobayashi et al, Photoreceptor synaptic Protein HRG4 (UNC119) interacts with ARL2 via a putative conserved domain, FEBS Letters, 2003, pp. 26-32, vol. 534.

Weiquan Wang, Molecular Characterization and Mapping of Cacine cGMP-Phosphodiesterase Delta Subunit (PDE6D), The International Journal on Genes and Genomes, 1999, pp. 325-332, vol. 236.

Ning Li, Characterization of Human and Mouse Rod cGMP Phosphodiesterase δ Subunit (PDE6D) and Chromosomal Localization of the Human Gene, University of Utah, 1998, pp. 76-82.

Richard L. Hurwitz et al., Immunology Characterization of the Photoreceptor Outer Segment Cyclic GMP Phosphodiesterase, The journal of Biological Chemistry, 1984, pp. 8612-8618, vol. 259, No. 13.

Peter G. Gillespie et al., A Soluble Form of Bovine Rod Photoreceptor Phosphodiesterase has a Novel 15-kDa Subunit, The Journal of Biological Chemistry, 1989, pp. 12187-12193, vol. 264, No. 21.

Lubert Stryer, Visual Excitation and Recovery, The Journal of Biological Chemistry, 1991,pp. 10711-10714, vol. 266, No. 17.

Stephanie K. Florio, Solubilization of Membrane-bound Rod Phosphodiesterase by the Rod Phosphodiesterase Recombinant δ Subunit, The Journal of Biological Chemistry, 1996, pp. 24036-24047, vol. 271, No. 39.

Hongmei Mou et al., cGMP Binding to Noncatalytic Sites on Mammalian Rod Photoreceptor Phosphodiesterase Is Regulated Binding of Its γ and δ Subunites, The Journal of Biological Chemistry, 1999, pp. 18813-18820, vol. 274, No. 26.

Anil K. Jaiswal, Human NAD (P) H: Quinone Oxidoreductase$_2$, Gene Structure, Activity, and Tissue-Specific Expression, The Journal of Biological Chemistry, 1994, pp. 14502-14508, vol. 269, No. 20.

Delwin J. Long, Disruption of Dihydronicotinamide Riboside:Quinone Oxidoreductase 2 (NQO2) Leads to Myeloid Hyperlasia of Bone Marrow and Decreased Sensitivity to Menadione Toxicity, The Journal of Biological Chemistry, 2002, pp. 46131-46139, vol. 277, No. 48.

Lorna Goshman, R.Ph, Perspective on Cholesterol Lowering Agents: Atorvastatin, 1998, pp. 28-34.

Derrick L.J. Clive et al., Total Synthesis of Both (+)-Compactin and (+)-Mevinolin. A General Strategy Based on the Use of a Special Titanium Reagent for Dicarbonyl Coupling, J. Am. Chem. Soc., 1990, pp. 3018-3028, vol. 112.

Jun-Ho Maeng, Ph.D., Trip Report: CU-Array Biopharma Symposium on Medicinal and Synthetic Organic Chemistry, Technical Reports, 2001, pp. 1-10, vol. 6, No. 33.

G. Beck. K. Kesseler et al., Synthesis and Biological Activity of New HMG-CoA Reductase Inhibitors. I. Lactones of Pyridine- and Pyrimidine-Substituted 3,5—Dihydroxy-6-heptenoic, J. Med. Chem., 1990, pp. 52-60, vol. 33.

A Document for Use by NHS Managers and Budget Holders as an Adjunct to the UKMI/NPC "New Drugs in Clinical Developement" Scheme, paper prepared by UKMI and NHS, 2002, pp. 1-12.

Anthoney Trippe, Patentability and FTO Search Report, 2004, pp. 1-269.

Beilstein Crossfire Search, , 2004, pp. 1-10.

Prous Science Integrity Search CAS Registry No. CAS Registry No. 147098-20-2, 147098-18-8, 287714-41-4, 2003, pp. 1-7.

Prous Science Integrity Search CAS Registry No. 147526-32-7, 141750-63-2, 147511-69-1, 192565-91-6, 2003, pp. 1-17.

Prous Science Integrity Search CAS Registry No. 132100-55-1, 135910-20-2, 2003, pp. 1-3.

Prous Science Integrity Search CAS Registry No. 122254-45-9, 2003, pp. 1-2.

Prous Science Integrity Search CAS Registry No. 132017-01-7, 2003, pp. 1-3.

Prous Science Integrity Search CAS Registry No. 120551-59-9, 2003, pp. 1-2.

Prous Science Integrity Search CAS Registry No. 134523-03-8, 2003, pp. 1-18.

Prous Science Integrity Search CAS Registry No. 125035-66-7,2003, pp. 1-2.

Prous Science Integrity Search CAS Registry No. 075330-75-5, 2003, pp. 1-5.

Prous Science Integrity Search CAS Registry No. 079902-63-9, 2003, pp. 1-11.

Prous Science Integrity Search CAS Registry No. 081131-70-6,081093-37-0, 2003,pp. 1-8.

Prous Science Integrity Search CAS Registry No. 093957-55-2, 093957-54-1, 2003, pp. 1-11.

Prous Science Integrity Search CAS Registry No. 143201-11-0, 145599-86-6, 2003, pp. 1-10.

* cited by examiner

PDE6D::HA11

A = Atorvastatin    R = Rosuvastatin    C = Cerivastatin

P = Pravastatin     S = Simvastatin     F = Fluvastatin

L = Lovastatin

A = Atorvastatin

A = Atorvastatin     S = Simvastatin

781430 = 30          782236 = 36

COMPETITORS:

- A, F, Q used at 10 μM

- M and FAD used at 100 μM

▶ = NQO2

Lipitor Intermediate M-4

D-Glucamine
1-Amino-1-deoxy D-glucitol

780390

C₃₃H₃₆FN₃O₂
Mol. Wt.: 525.66

780416

C₃₅H₃₃FN₂O₂
Mol. Wt.: 532.65

780442

C₃₄H₃₁FN₂O₂
Mol. Wt.: 518.62

780468

C₃₀H₃₁FN₂O₂
Mol. Wt.: 470.58

780494

C₃₂H₃₅FN₂O
Mol. Wt.: 482.63

780520

C₃₃H₃₄FN₃O₂
Mol. Wt.: 523.64

780650

C$_{33}$H$_{35}$FN$_2$O$_3$
Mol. Wt.: 526.64

780624

C$_{31}$H$_{27}$FN$_2$O$_2$
Mol. Wt.: 478.56

780598

C$_{30}$H$_{31}$FN$_2$O$_3$
Mol. Wt.: 486.58

780572

C$_{33}$H$_{29}$FN$_2$O
Mol. Wt.: 488.59

780546

C$_{32}$H$_{33}$FN$_2$O$_3$
Mol. Wt.: 512.61

780676

C$_{31}$H$_{33}$FN$_2$O$_2$
Mol. Wt.: 484.60

780702

C₃₂H₃₅FN₂O₂
Mol. Wt.: 498.63

780728

C₃₃H₃₅FN₂O₃
Mol. Wt.: 526.64

780832

C₃₁H₃₃FN₂O₂
Mol. Wt.: 484.60

780962

C₃₁H₃₃FN₂O₂
Mol. Wt.: 484.60

780936

C₃₂H₃₅FN₂O₂
Mol. Wt.: 498.63

780910

C₃₆H₃₅FN₂O₃
Mol. Wt.: 562.67

780884

C$_{36}$H$_{35}$FN$_2$O$_2$S
Mol. Wt.: 578.74

780754

C$_{30}$H$_{30}$FN$_3$O$_2$
Mol. Wt.: 483.58

782184

C$_{28}$H$_{25}$FN$_2$O$_4$
Mol. Wt.: 472.51

782210

C$_{29}$H$_{27}$FN$_2$O$_4$
Mol. Wt.: 486.53

782236

C$_{32}$H$_{35}$FN$_2$O$_6$
Mol. Wt.: 562.63

782366

C$_{31}$H$_{33}$FN$_2$O
Mol. Wt.: 468.60

783770

C₃₀H₂₉FN₂O₄
Mol. Wt.: 500.56

783796

C₂₉H₂₉FN₂O₂
Mol. Wt.: 456.55

783900

C₄₂H₅₆FN₃O₈
Mol. Wt.: 749.91

783874

C₂₈H₂₅FN₂O₃
Mol. Wt.: 456.51

783016

C₂₆H₂₅FN₂
Mol. Wt.: 384.49

780858

C₂₆H₂₄N₂O
Mol. Wt.: 380.48

780988

C₂₇H₂₆N₂O₂
Mol. Wt.: 410.51

781014

C$_{30}$H$_{32}$N$_2$O
Mol. Wt.: 436.59

782028

C$_{21}$H$_{22}$N$_2$O
Mol. Wt.: 318.41

783588

C$_{19}$H$_{17}$NO$_2$
Mol. Wt.: 291.34

783718

C$_{17}$H$_{13}$NO$_2$
Mol. Wt.: 263.29

782080

C$_{21}$H$_{20}$FNO
Mol. Wt.: 321.39

782054

C$_{23}$H$_{22}$FNO$_2$
Mol. Wt.: 363.42

PYRROLE COMPOUNDS AND USES THEREOF

CROSS-REFERENCE TO RELATED APPLICATIONS

This application claims the benefit of U.S. Provisional Application No. 60/471,425 filed May 16, 2003, U.S. Provisional Application No. 60/480,289 filed Jun. 20, 2003, U.S. Provisional Application No. 60/488,178 filed Jul. 16, 2003, U.S. Provisional Application No. 60/488,172 filed Jul. 16, 2003, U.S. Provisional Application No. 60/480,475 filed Jun. 20, 2003, U.S. Provisional Application No. 60/516,610 filed Oct. 30, 2003, U.S. Provisional Application No. 60/516,651 filed Oct. 30, 2003 and U.S. Provisional Application No. 60/516,616 filed Oct. 30, 2003 all of which are incorporated herein by reference.

BACKGROUND OF THE INVENTION

Phosphodiesterase 6 delta (PDE6D) was originally identified as a regulatory (non-catalytic) subunit of the enzyme PDE6. PDE6 is expressed exclusively in photoreceptor cells, and plays a critical role in retinal phototransduction. (Stryer, L. (1991) J. Biol. Chem. 266:10711-14; (Florio, S. K. et al. (1996) J. Biol. Chem. 271:24036-47. The PDE6 holoenzyme exists as both membrane-associated and soluble forms, and only the membrane-associated form is active in phototransduction, whereas, only the soluble form contains the PDE6D subunit. PDE6D regulates the subcellular localization and thus the activity of PDE6, and the release of PDE6 from membranes is mediated by PDE6D. PDE6D has been observed to reduce light-induced cGMP hydrolysis in rod outer segments (Cook et al., J. Biol. Chem 276(7):5248-5255 (2001)), presumably by removing the PDE6 holoenzyme from the membrane. PDE6D solubilizes PDE6 by binding specifically to prenylated peptide sequences near the C-termini of the PDE6A and PDE6B subunits. PDE6D is referred to in the scientific literature using several different designations, including PDE delta, PDEδ, PDE6 delta, PDE6δ, PDE6D and PDED.

PDE6D interacts specifically with a host of important cell signaling proteins through their post-translational modification with isoprenoid intermediates, which are products of the cholesterol biosynthetic pathway. One such modification is called prenylation and involves the attachment of phospholipids to proteins after translation, particularly the large class of GTP-binding proteins. Prenyl groups are important for proper cellular localization and trafficking. The availability of isoprenoid intermediates for prenylation of GTP-binding proteins has been associated with various cardiovascular, inflammatory, cancerous and neurological diseases. A reduction in the amount of available prenyl groups has been associated with improved endothelial function, decreased oxidative stress, decreased inflammation and increased neuroprotective effects.

Due to the possible role of PDE6 in several diseases, there is a need to develop PDE6 modulators.

SUMMARY OF THE INVENTION

In one aspect, the present invention provides pyrrole compounds and uses thereof. The compounds described herein are useful in the treatment of various diseases; in particular diseases in which modulation of PDE6, quinone reductase 2 (QR2) (also known as NQO2), and/or calbindin-2 (CLB2) is desired.

The compounds and compositions of the invention are useful as therapeutic and/or prophylactic agents for diseases caused by or aggravated by PDE6, QR2, or CLB2. Examples of such diseases include, but are not limited to, cardiovascular diseases, such as arteriosclerosis, hypertension, arrhythmia (e.g. ischemic arrhythmia, arrhythmia due to myocardial infarction, myocardial stunning, myocardial dysfunction, arrhythmia, and the like), angina pectoris, cardiac hypertrophy, myocardial infarction, heart failure (e.g. congestive heart failure, acute heart failure, cardiac hypertrophy, etc.); renal diseases, diabetes mellitus, diabetic nephropathy, ischemic acute renal failure, acute renal failure, and the like; cerebrovascular diseases, such as ischemic stroke, hemorrhagic stroke, and the like; and cerebro-ischemic disorders, such as disorders associated with cerebral infarction, disorders caused after cerebral apoplexy as sequelae, or cerebral edema, and any combination thereof, as described in detail below.

In another aspect, the present invention provides compositions and methods for treating and/or preventing neurodegenerative conditions and diseases. Certain compounds of the invention exhibit neuroprotective effects. The pyrrole compounds can be delivered alone or in combination with additional agents, and can be used for the treatment and/or prevention of neurodegenerative conditions and diseases such as those resulting from ischemic strokes. The neurodegenerative diseases that can be treated with the compounds of the present invention include, but are not limited to, ischemic stroke, basal ganglia or Parkinson's disease, epilepsy or brain or spinal cord ischemia or trauma; Alzheimer's disease, diabetic peripheral neuropathy, multiple sclerosis, amyotrophic lateral sclerosis, traumatic brain injury, spinal cord injury, Huntington's disease, heart failure (e.g. congestive heart failure, acute heart failure, cardiac hypertrophy, etc.) or renal diseases, but is preferably ischemic stroke, traumatic brain injury, or Parkinson's disease and combinations thereof.

The pyrrole compounds and other compounds of the present invention can be administered per se or in a pharmaceutical composition containing a pharmaceutically acceptable excipient. The pyrrole compounds and the pharmaceutical compositions can be administered orally. Other suitable routes of administration include intravenous, intramuscular, subcutaneous, transdermal, buccal, or inhalation or in the form of a suppository.

These and other aspects of the present invention will become evident upon reference to the following detailed description. In addition, various references are set forth herein which describe in more detail certain procedures or compositions, and are incorporated by reference in their entirety.

DISCLOSURE OF THE INVENTION

Figure 1:
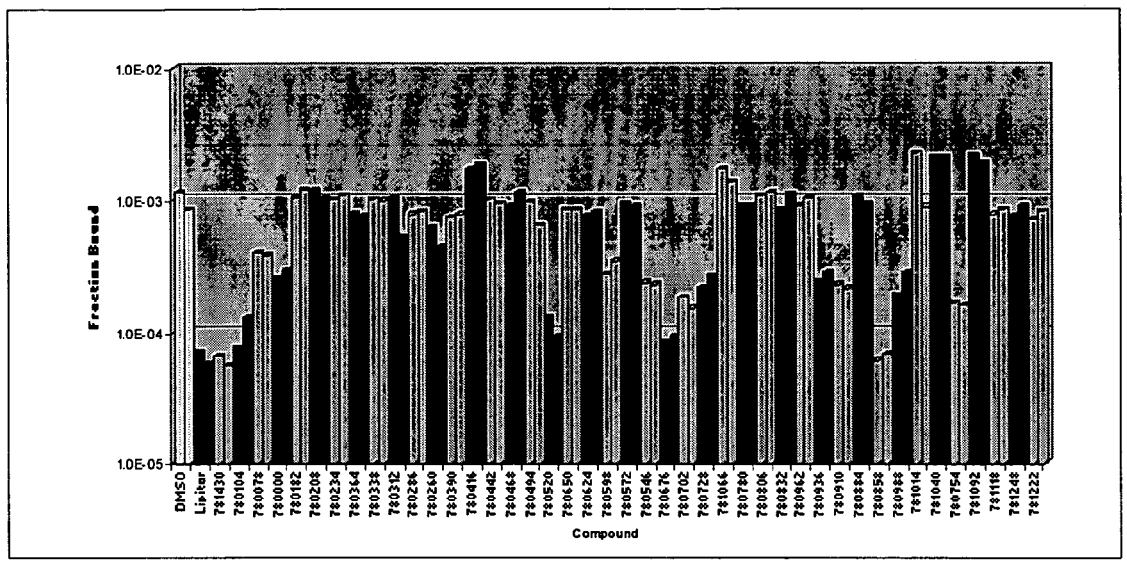
FIG. 1 shows the results of a screen for novel molecules that bind phage displayed PDE6D in the presence of immobilized atorvastatin. The y-axis relates to the fractional amount of phage bound to the immobilized atorvastatin in the presence of 2 µM of various compounds, DMSO was used as a control.

The present inventors have identified novel interactions between atorvastatin and PDE6, QR2, and CLB2. Pyrrole compounds that preferably interact with PDE6, QR2, or CLB2 are described herein. In some embodiments, the pyrrole compounds exhibit minimal interaction with HMG CoA reductase.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, NMR, HPLC, protein chemistry, biochemistry, recombinant DNA techniques and pharmacology, within the skill of the art.

The terms "effective amount" or "pharmaceutically effective amount" refer to a nontoxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of the compound having the imidazole skeleton as disclosed herein per se or a composition comprising the compound herein required to provide a clinically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

As used in herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

As used herein, the term "halogen" includes fluorine, chlorine, bromine, and iodine.

The term "alkyl" as used herein refers to a substituted or unsubstituted straight, branched, or cyclic hydrocarbon chain fragment or radical, preferably containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having ten or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like. Alkyl groups containing double bonds such as just described will also be referred to herein as "alkylenes".

The term "aryl" as used herein refers to cyclic aromatic, hydrocarbon chains having twenty or fewer carbon atoms, e.g., phenyl, naphthyl, biphenyl and anthracenyl. One or more carbon atoms of the aryl group may also be substituted with, e.g., alkyl; aryl; heterocycle; formyl; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; ureido; or thioureido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

As used herein, "aliphatic" includes alkanes, olefins (alkenes or alkyldienes), and alkynes.

Alicyclic includes substituted or unsubstituted cycloparaffins (saturated), cycloolefins (unsaturated with two or more double bonds), and cycloacetylenes (cyclynes) with at least one triple bond. Non-limiting examples include cyclopropane, cyclohexane, cyclopentane, cyclopentadiene, and cycloctatetraene.

Aromatic refers to substituted or unsubstituted unsaturated cyclic hydrocarbons of one or more rings and includes aryl structures typified, but not limited to, phenyl, naphthalyl, phenanthrenyl, and anthracenyl. Non-limiting aromatic examples include 6 membered (typified by benzene) as well as 5 membered (typified by furan, thiophene, pyrrole, and indole) rings.

Heterocycle refers to the presence of at least one non-carbon atom in a cyclic structure. Non-limiting examples include the presence of a nitrogen, oxygen, and sulfur atom to result in heterocyclic rings including, but not limited to, phenyl, naphthyl, pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl andindazolyl; wherein such phenyl, naphthyl or heterocyclic group is optionally substituted with one to five groups selected from the group consisting of a C1-6 branched or unbranched alkyl, phenyl, naphthyl, heterocycle selected from the group hereinabove described, C1-6 branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl C1-5 alkyl, naphthyl C1-5 alkyl, halo, hydroxy, cyano, C1-3 alkyloxy which may optionally be partially or fully halogenated, phenyloxy, naphthyloxy, heteraryloxy wherein the heterocyclic moiety is selected from the group hereinabove described, nitro, amino, mono- or di-(C1-3)alkylamino, phenylamino, naphthylamino, heterocyclylamino wherein the heterocyclyl moiety is selected from the group hereinabove described, $NH_2C(O)$, a mono- or di-(C1-3)alkyl aminocarbonyl, C1-5 alkyl-C(O)—C1-4 alkyl, amino-C1-5 alkyl, mono-or di-(C1-3)alkylamino-C1-5 alkyl, amino-S(O)2, or di-(C1-3) alkylamino-S(O)2; or a fused aryl selected from the group consisting of benzocyclobutanyl, indanyl, indenyl, dihydronaphthyl, tetrahydronaphthyl, benzocycloheptanyl and benzocycloheptenyl, or a fused heterocyclic moiety selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoitnidazole, cyclohexanoimidazole, cyclopentanothiophene and cyclohexanothiophene, wherein the fused aryl or fused heterocyclic ring is substituted with 0 to 3 groups independently selected from phenyl, naphthyl and heterocyclic moiety selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, C1-6 branched or unbranched alkyl which is optionally partially or fully halogenated, halo, cyano, C1-3 alkyloxy which is optionally partially or fully halogenated, phenyloxy, naphthyloxy, heterocyclyloxy wherein the heterocyclic moiety is selected from the group hereinabove described, nitro, amino, mono- or di-(C1-3) alkylamino, phenylamino, naphthylarnino, heterocyclylamino wherein the heterocyclic moiety is selected from the group hereinabove described, $NH_2C(O)$, a mono- or di-(C1-3)alkyl aminocarbonyl, C1-4 alkyl-OC(O), C1-5 alkyl-C(O)-C1-4 branched or unbranched alkyl, an amino-C1-5 alkyl, or mono- or di-(C1-3)alkylamino-C1-5 alkyl; or c) cycloalkyl selected from the group consisting of cyclopentanyl, cyclohexanyl, cycloheptanyl, bicyclopentanyl, bicyclohexanyl and bicycloheptanyl, wherein the cycloalkyl may optionally be partially or fully halogenated and which may optionally be substituted with one to three C1-3 alkyl groups; or azetidinyl, pyrrolidinyl, piperidinyl, morpholino, piperazinyl, hexahydroazepinyl or octahydroazocinyl.

All of the above described aliphatic, carboxyalkyl, carbalkoxyalkyl, alkoxy, alicyclic, aryl, aromatic, and heterocyclic moieties may, of course, also be optionally substituted with 1-3 substituents independently selected from halo (fluoro, chloro, bromo or iodo), alkyl, and alkoxy.

Sulfonyl refers to the presence of a sulfur atom, which is optionally linked to another moiety such as an aliphatic group, an aromatic group, an aryl group, an alicyclic group, or a heterocyclic group. Aryl or alkyl sulfonyl moieties have the formula —$SO_2R'$, and alkoxy moieties have the formula —O—R', wherein R' is alkyl, as defined above, or is aryl wherein aryl is phenyl, optionally substituted with 1-3 substituents independently selected from halo (fluoro, chloro, bromo or iodo), lower alkyl (1-6C) and lower alkoxy (1-6C).

Pyrrole Compounds

The present invention is directed to pyrrole compounds and methods for their use as drugs. The pyrrole compounds and other compounds of the invention may be used to treat a variety of diseases. Preferably, the compounds described herein are used in the treatment of PDE6-related, QR2-related and CLB2-related conditions.

Those of skill in the art will recognize that the pyrrole compounds described herein may exhibit the phenomena of tautomerism, conformational isomerism, geometric isomerism and/or optical isomerism. It should be understood that the invention encompasses any tautomeric, conformational isomeric, optical isomeric and/or geometric isomeric forms of the pyrrole compounds described herein, as well as mixtures of these various different forms. For example, the compounds of the present invention comprise several chiral atoms and it is intended that the present invention encompass all possible stereoisomers and racemic mixtures thereof. Accordingly, the compounds described herein may be administered in their entantiomerically pure forms or as a mixture of enantiomers, such as a racemic mixture.

It will also be appreciated that in many instances the pyrrole compounds may metabolize to produce active pyrrole compounds. The use of active metabolites is also within the scope of the present invention.

In one embodiment, the invention provides compounds as represented by the following formula I or a diastereomer, enantiomer, or pharmaceutically acceptable salt thereof

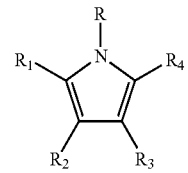

(I)

wherein R is any suitable substituent, except the following—

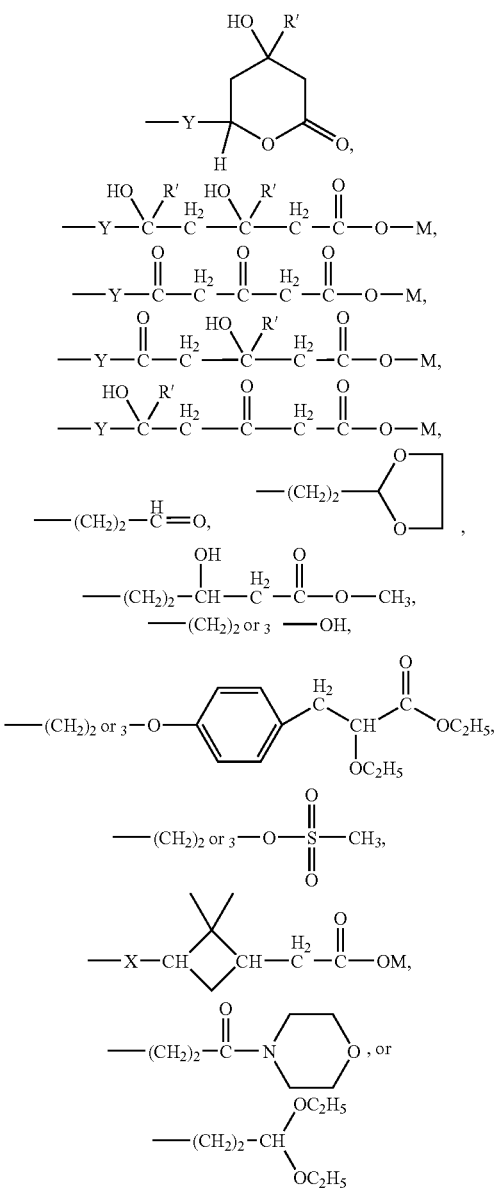

wherein R', X, Y, and M are any suitable substituents and wherein $R_1$ is optionally substituted aromatic or heterocycle ring. $R_2$ and $R_3$ are independently —$CONR_5R_6$ where $R_5$ and $R_6$ are independently hydrogen; optionally substituted alkyl, aromatic or heterocycle ring. $R_4$ is optionally substituted alkyl or —OR" wherein R" is optionally substituted alkyl or aryl. When R₁, R₂, or R₃ is an aromatic or heterocyclic moiety, it is optionally linked to the rest of the molecule by a straight or branched carbon chain.

R can be hydrogen, a straight or branched, saturated or unsaturated aliphatic, including alkyl, carboxyalkyl, carbalkoxyalkyl, or alkoxy; a alicyclic; a single or multiring aromatic substituted aliphatic; an aliphatic-substituted single or multiring aromatic; a single or multiring aromatic heterocycle; a single or multiring heterocyclic aliphatic; an amine; or a sulfonyl; or cyano; or a naturally or non-naturally occurring amino acid. R can also be an alcohol, acetal, thioacetal, ether, thioether, acetal, thioacetal, epoxide, aldehyde, ketone, carboxylic acid, thiol, imino, phosphoric acid, urea, thiourea, sulfonamide, or a halogen. In some preferred embodiments, R is a polyethylene glycol chain. In one embodiment, R is not H. In certain embodiments when R is H, the pyrrole compound is an isolated, stable, preferably non-charged moiety.

In particular, R can be OH, C1-10, C2-C9, C3-C8, C4-C7, C5-C6 alkyl, alkene or alkyldiene. Preferably, R is a lower alkyl group, such as methyl, ethyl, n-propyl, isopropyl, t-butyl and n-pentyl; a lower alkyl carboxylic acid, such as formyl, carboxymethyl, carboxyethyl, carboxy-n-butyl, carboxy-sec-butyl, carboxy-n-hexyl; —(CH₂)$_n$OH or —(CH₂)$_n$COO⁻ or an ester thereof represented by —(CH₂)$_n$COO(CH₂)$_n$CH₃, wherein each occurrence of n is independently an integer, preferably from 1-6, and each CH₂ position may be optionally substituted by OH, fluoro, chloro, bromo or iodo. Non-limiting examples of R include —CH₂CH₂COOCH₃, —CH₂CH₂COOCH₂CH₃, —CH₂CH(CH₃)COOCH₂CH₃, —CH₂CH₂CH₂COOCH₂CH₂CH₃, —CH₂CH(CH₃)₂COOCH₂CH₃.

Preferably R₁ is 1-naphthyl; 2-naphthyl; cyclohexyl; norbornenyl; 2-, 3-, or 4-pyridinyl; phenyl or benzyl; phenyl or benzyl substituted with fluorine, chlorine, bromine, iodine, hydroxyl, trifluoromethyl, difluoromethyl, fluoromethyl, trifluoromethoxy, difluoromethoxy, fluoromethoxy, alkyl of from one to four carbon atoms, alkoxy of from one to four carbon atoms, a heterocyclic moiety, or alkanoyloxy of from two to eight carbon atoms. R₅ and R₆ are preferably independently hydrogen; alkyl of from one to six; 2-, 3-, or 4-pyridinyl; phenyl or benzyl; phenyl or benzyl substituted with fluorine, chlorine, bromine, iodine, cyano, trifluoromethyl, difluoromethyl, fluoromethyl, trifluoromethoxy, difluoromethoxy, fluoromethoxy, pyridine, or carboalkoxy of from three to eight carbon atoms. R₄ is preferably alkyl of from one to six carbon atoms as described herein; isopropyl, isobutyl, isopentyl, as well as the sec-, normal, tert- or neo-forms thereof, such as n-butyl, and t-butyl; cyclopropyl, cyclobutyl, cyclopentyl or cyclohexyl; F; Br; Cl; I; trifluoromethyl or —OR' wherein R' is alkyl or aryl of C1-C10.

Even more preferably, R₁ is phenyl substituted with fluorine, chlorine, bromine, iodine, trifluoromethyl, difluoromethyl, fluoromethyl, trifluoromethoxy, difluoromethoxy, fluoromethoxy or hydroxyl. The most preferred substitution being fluorine, optionally at the para position relative to the bond linking the phenyl group to the rest of the molecule. In another preferred embodiment, R₂ is phenyl or —C(O)NR₅R₆ where R₅ and R₆ are phenyl. In yet another preferred embodiment, R₃ is phenyl or —C(O)NR₅R₆ where R₅ and R₆ are phenyl. In another embodiment, R₄ is —CH(CH₃)₂ or -trifluoromethyl; -difluoromethyl; -fluoromethyl; -trifluoromethoxy; -difluoromethoxy; -fluoromethoxy.

In some embodiments, pyrrole compounds represented by the following formula Ia or a diastereomer, enantiomer, or pharmaceutically acceptable salt thereof are provided:

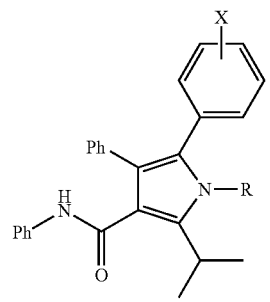

(Ia)

wherein X is a halogen, optionally substituted alkyl, alicyclic, aryl, or heterocycle and R is as described above. Preferably X is fluorine, trifluoromethyl, difluoromethyl, fluoromethyl, trifluoromethoxy, difluoromethoxy, or fluoromethoxy.

In other embodiments, the pyrrole compounds represented by the following formula Ib are provided

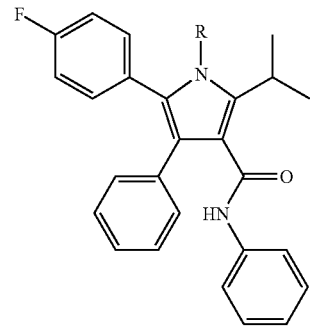

(Ib)

wherein R is as defined above.

In some embodiments, the pyrrole compounds of formula I are quarternany amine salts such as the following formula Ic

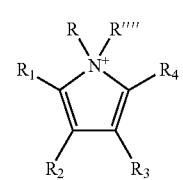

(Ic)

wherein R"" is any suitable substitutent.

Preferred R groups include the following:

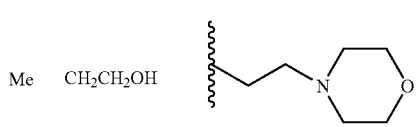

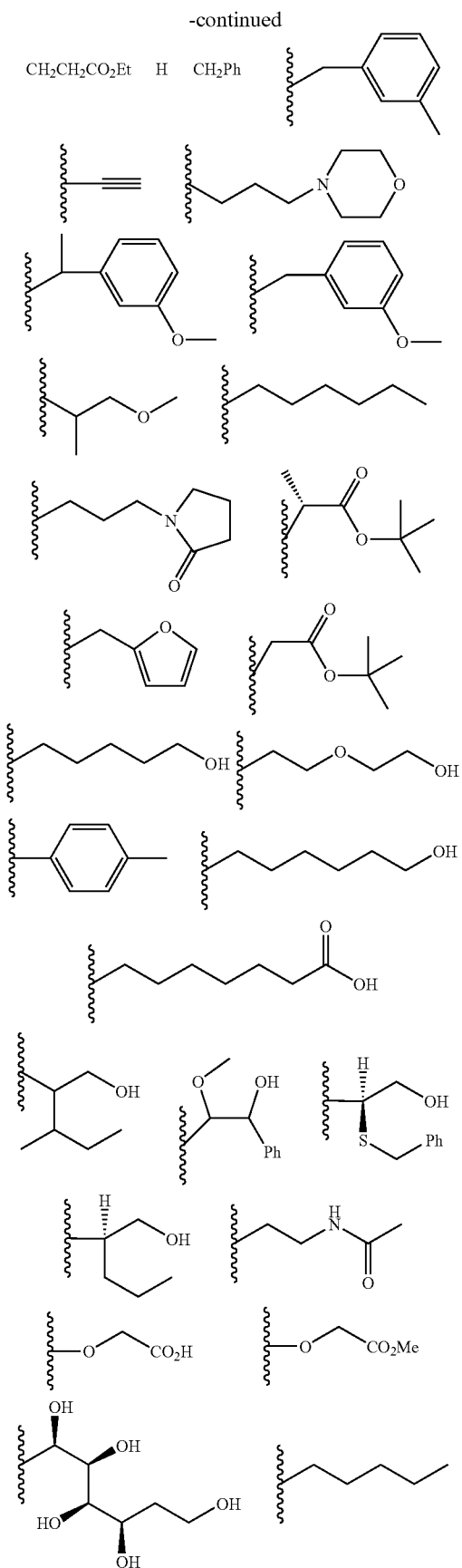
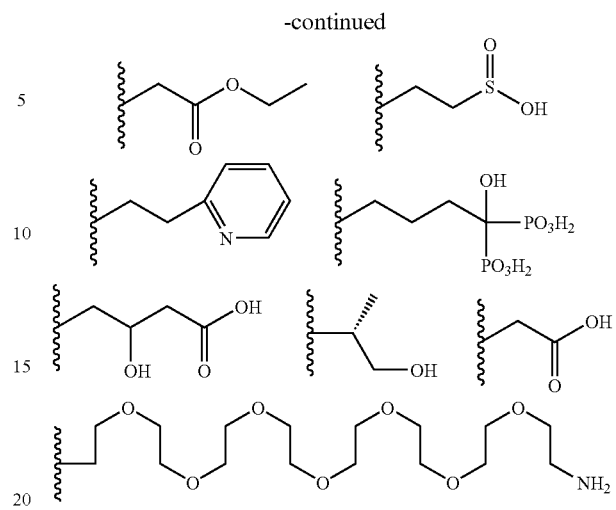

The chiral carbon atoms depicted above in the preferred R groups include all possible stereoisomers, as well as racemic mixtures thereof.

In some embodiment, the R group in the compounds of formula I is $(CR_7R_8)_m(CR_9R_{10}CR_{11}OH)_n-CR_{12}R_{13}R_{14}$ where $R_7$, $R_8$, $R_9$, $R_{10}$, and $R_{11}$ are independently selected from the group consisting of H, OH, or alkyl, preferably lower alkyl; $R_{12}$, $R_{13}$, and $R_{14}$ are independently selected to be H, OH, or $PO_3H_2$; m is an integer, preferably between 0 and 4 and n is an integer, preferably between 0 and 5. It is to be understood that the present invention encompasses these compounds in any of their tautomeric forms or as an a mixture thereof; or as a mixture of diastereomers, as well as in the form of an individual diastereomer, and that the present invention encompasses compounds as a mixture of enantiomers, as well as in the form of an individual enantiomer. Exemplary compounds of formula Ib are shown below and in FIG. 33.

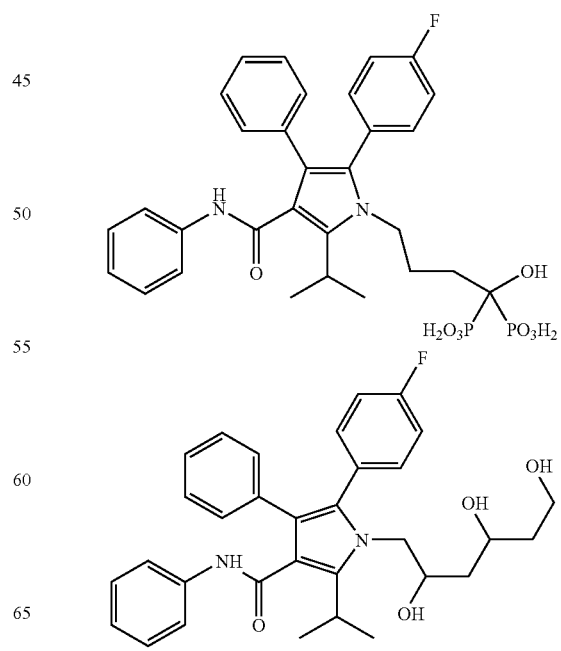

-continued

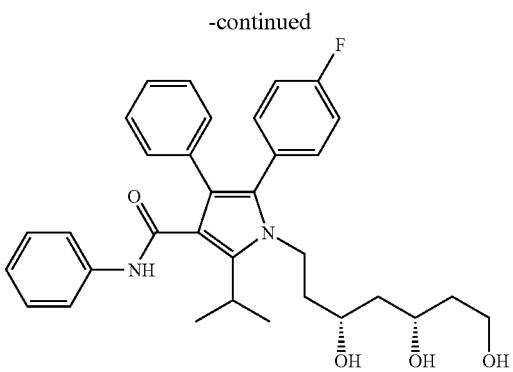

One aspect of the invention is methods of using the pyrrole compounds described herein. The methods include therapeutic and prophylactic uses and also uses in certain assays. Most preferably these methods are carried with the compounds depicted in FIG. 33A-33H.

The invention also provides pyrrole compounds of the following formula or a diastereomer, enantiomer, or pharmaceutically acceptable salt thereof,

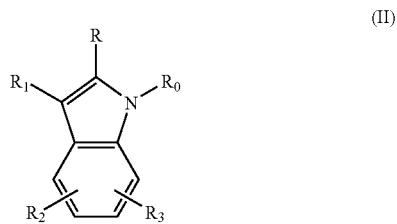

(II)

wherein R is as defined above for formula I and wherein one of $R_1$ or $R_0$ is

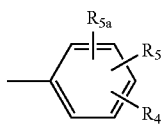

and the other is optionally substituted alkyl, preferably a $C_{1-6}$ alkyl, not containing an asymmetric carbon atom, cycloalkyl, preferably $C_{3-6}$, or phenyl. The optional substitutents include fluorine, chlorine, bromine, iodine, trifluoromethyl, difluoromethyl, fluoromethyl, trifluoromethoxy, difluoromethoxy, fluoromethoxy, alkoxy, hydroxyl, or phenyl-$(CH_2)_m$—. $R_4$ is hydrogen, $C_{1-3}$ alkyl, n-butyl, i-butyl, t-butyl, $C_{1-3}$ alkoxy, n-butoxy, i-butoxy, trifluoromethyl, difluoromethyl, fluoromethyl, trifluoromethoxy, difluoromethoxy, fluoromethoxy, fluoro, chloro, bromo, iodo, phenoxy or benzyloxy. $R_5$ is hydrogen, $C_{1-3}$ alkyl, $C_{1-3}$ alkoxy, fluoro, chloro, bromo, iodo, trifluoromethyl, difluoromethyl, fluoromethyl, trifluoromethoxy, difluoromethoxy, fluoromethoxy, alkoxy, phenoxy or benzyloxy. $R_{5a}$ is hydrogen, $C_{1-2}$ alkyl, $C_{1-2}$ alkoxy, fluoro, chloro, bromo, iodo, trifluoromethyl, difluoromethyl, fluoromethyl, trifluoromethoxy, difluoromethoxy, fluoromethoxy, or alkoxy and m is 1, 2 or 3, with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, difluoromethyl, fluoromethyl, trifluoromethoxy, difluoromethoxy, fluoromethoxy, and not more than one of $R_4$ and $R_5$ is phenoxy, and not more than one of $R_4$ and $R_5$ is benzyloxy. Alternatively, $R_0$ is isopropyl, prenyl, allyl, isobutyl, isopentyl, as well as the sec-, normal, tert- or neo-forms thereof, such as n-butyl, and t-butyl; cyclopropyl, cyclobutyl, cyclopentyl or cyclohexyl; F; Br; Cl; I; trifluoromethyl; difluoromethyl; fluoromethyl; trifluoromethoxy; difluoromethoxy; fluoromethoxy or —OR' wherein R' is alkyl or aryl of C1-C10 and $R_1$ is as described above. $R_2$ is hydrogen, $C_{1-3}$ alkyl, prenyl, allyl, n-butyl, i-butyl, t-butyl, $C_{3-6}$ cycloalkyl, $C_{1-3}$ alkoxy, n-butoxy, i-butoxy, trifluoromethyl, difluoromethyl, fluoromethyl, trifluoromethoxy, difluoromethoxy, fluoromethoxy, fluoro, chloro, phenoxy or benzyloxy. $R_3$ is hydrogen, $C_{1-3}$ alkyl, $C_{1-3}$ alkoxy, trifluoromethyl, difluoromethyl, fluoromethyl, trifluoromethoxy, difluoromethoxy, fluoromethoxy fluoro, chloro, phenoxy or benzyloxy, with the provisos that $R_3$ must be hydrogen when $R_2$ is hydrogen, not more than one of $R_2$ and $R_3$ is trifluoromethyl, difluoromethyl, fluoromethyl, trifluoromethoxy, difluoromethoxy, or fluoromethoxy, and not more than one of $R_2$ and $R_3$ is phenoxy, and not more than one of $R_2$ and $R_3$ is benzyloxy.

The $R_0$, $R_1$, $R_2$, $R_3$, and $R_4$ positions of formula II above may be as defined for the $R_0$, R, $R_2$, $R_3$, and $R_4$ positions in the formulas of U.S. Pat. No. 5,354,772 in column 2, line 39, through column 9, line 32, and in the formulas of U.S. Pat. No. 4,739,073 in column 2, line 21, through column 8, line 37. Definitions that define those R groups are as further detailed in that Patent, which also provides reactions for the introduction of the various groups into formula II.

Preferably, $R_0$ of formula II is —$CH(CH_3)_2$ while $R_1$, $R_2$, and $R_3$ are as defined in the formula. Alternatively, $R_1$ is a phenyl, optionally substituted with fluorine, chlorine, bromine, iodine, trifluoromethyl, difluoromethyl, fluoromethyl, trifluoromethoxy, difluoromethoxy, fluoromethoxy, or hydroxyl while $R_0$, $R_2$, and $R_3$ are as defined in formula II; the substitution is preferably fluorine, and preferably at the para position relative to the bond linking the phenyl group to the rest of the molecule. Alternatively, $R_2$ is hydrogen $R_0$, $R_1$, and $R_3$ are as defined for formula IV'; or $R_3$ is hydrogen while $R_0$, $R_1$, and $R_2$ are as defined for formula II.

In one embodiment, the pyrrole compound represented by the following formula II is a compound of formula Ia or a diastereomer, enantiomer, or pharmaceutically acceptable salt thereof:

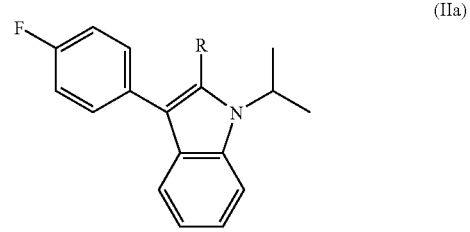

(IIa)

wherein R is as defined above for formula I.

The invention also provides prodrug forms of the above described pyrrole compounds and other compounds, wherein the prodrug is metabolized in vivo to produce a derivative as set forth above. Indeed, some of the above-described derivatives may be a prodrug for another derivative or active compound. The invention further provides for the optical isomers of the compounds disclosed herein, especially those resulting from the chiral carbon atoms in the molecule. In additional embodiments of the invention, mixtures of enantiomers and/or diastereoisomers, resulting from a single preparative step, combination, or interconversion are provided.

Methods of Synthesis

The compounds of the invention comprise pyrrole compounds and other compounds, as described herein. The compounds of the present invention, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). General methods for the preparation of pyrrole compound as disclosed herein may be derived from known reactions in the field. See for example Clive et al, J. Am. Chem 122:3018-3028 (1990) and Beck et al., J. Med. Chem. 33:52-60 (1990). In the discussion of methods that follows and on the attached pages, the reactions may be modified by the use of appropriate reagents and conditions, as would be recognized by the skilled person, for the introduction of the various moieties found in the formulae as provided herein.

Figure 28:
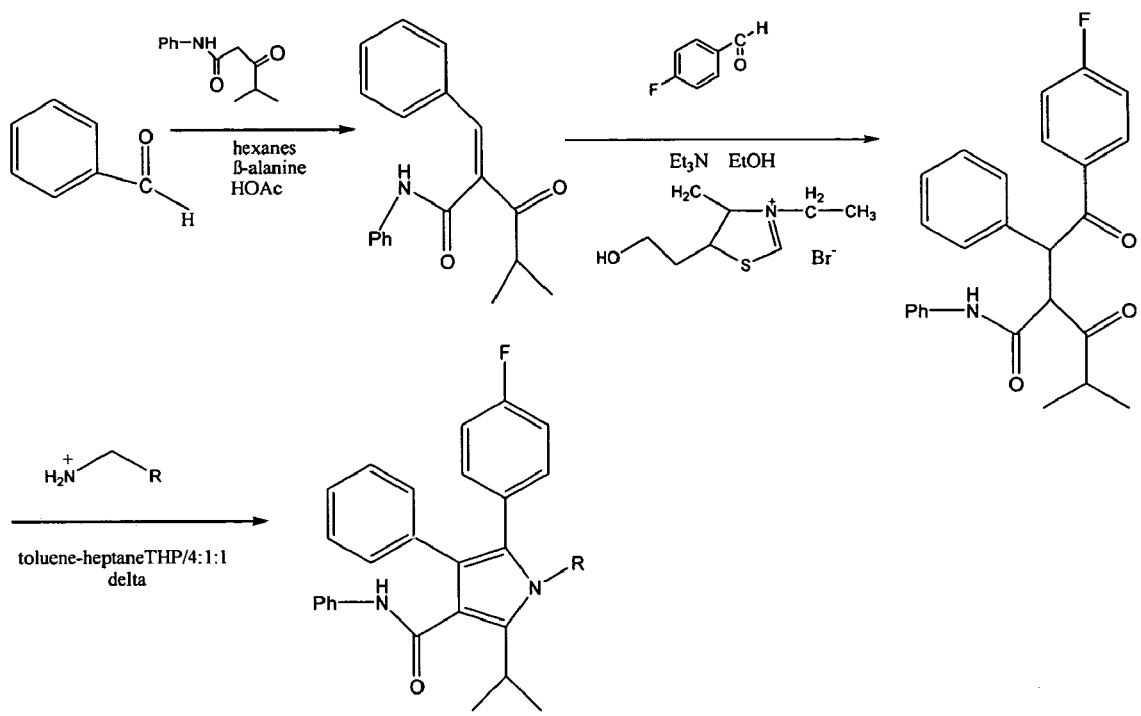
FIG. 28 shows Scheme 1 for the synthesis of pyrrole compounds.
Figure 29:
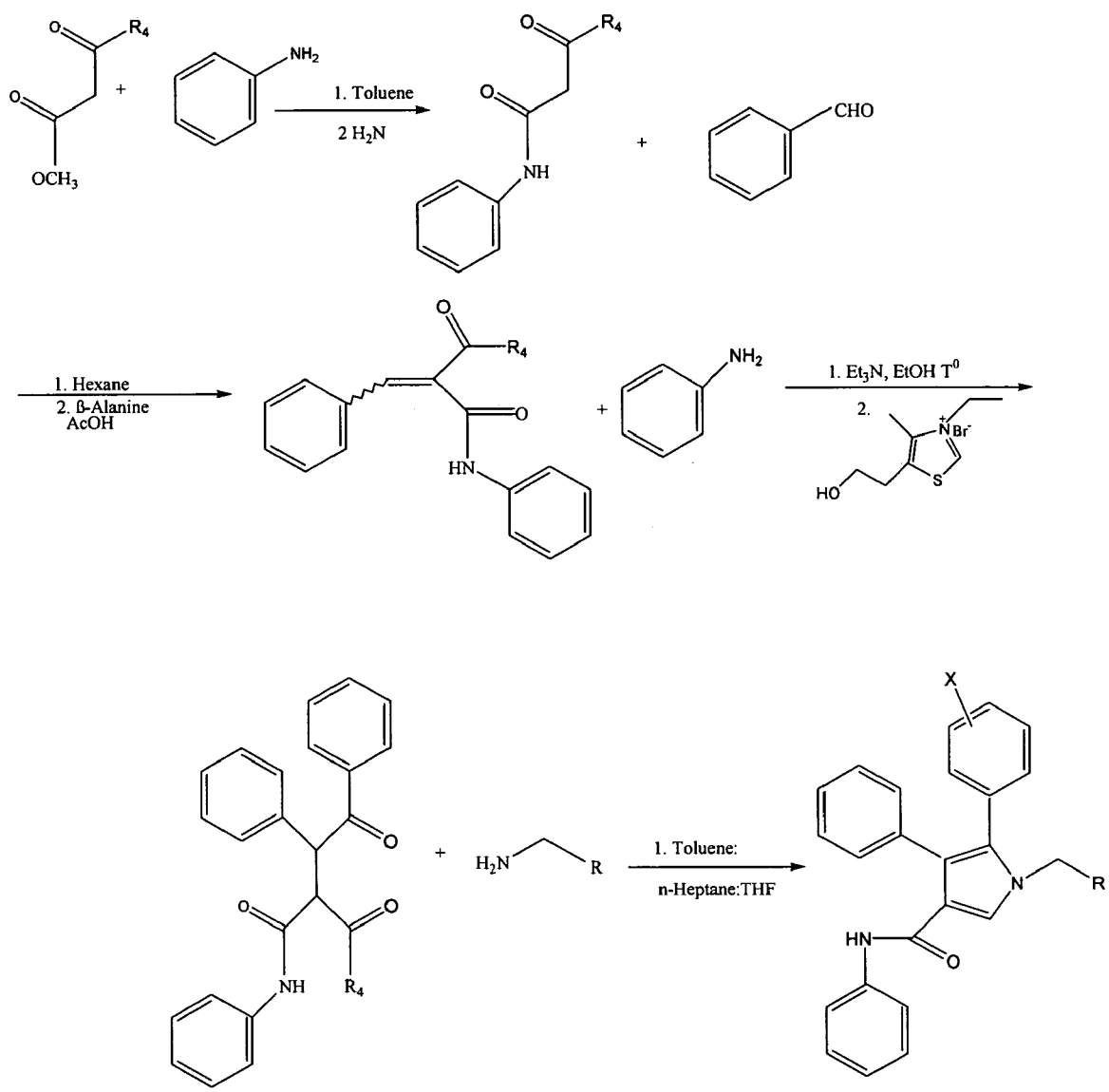
FIG. 29 shows Scheme 2 for the synthesis of pyrrole compounds.

Methods to synthesize atorvastatin are known in the field. See Atorvastatin, AN HMG-CoA Reductase Inhibitor and Effective lipid-regulating agent. Part III Syntheses of [$^{2}$H5], [$^{13}$C8] and [$^{13}$C7, $^{15}$N] Atorvastatin and their application in metabolic and pharmacokinetic studies'. J. Labelled Cpd. Radiopharm. 42, 135-145 (1999); Atorvastatin, AN HMG-CoA Reductase Inhibitor and Efficient Lipid-Regulating Agent Part I. Synthesis of ring-labeled [$^{14}$C] atorvastatin. J. Labelled Cpd. Radiopharm. 42, 121-127 (1999); and Atorvastatin, AN HMG-CoA Reductase Inhibitor and Efficient Lipid-Regulating Agent Part II. Synthesis of Side-Chain-Labeled [$^{14}$C] atorvastatin. J. Labeled Cpd. Radiopharm. 42, 129-133 (1999)). These methods can be adapted to synthesize the compounds described herein. A suitable synthesis scheme as adapted from J. Labelled Cpd. Radiopharm. 42, 135-145 (1999) is shown in FIG. 28. Another suitable synthesis scheme is shown in FIG. 29.

Activity of Pyrrole Compounds

The invention also provides methods for determining the level of activity of a pyrrole compound or another compound as disclosed herein in the treatment of a disease or unwanted condition as described herein. Such methods include the administration of a pyrrole compound to a subject followed by determination of the level of activity of said derivative in comparison to a subject who has not been administered said derivative or to a subject that has been administered a different amount or concentration of said derivative. These methods may be practiced repeatedly, with a variety of amounts or concentrations of the derivative to determine the level of activity over a range of conditions. The methods may also be used to determine that the level of activity is undetectable.

An exemplary method of determining the level of activity of a pyrrole compound may comprise a) administering a pyrrole compound or another compound as disclosed herein to a subject;

b) determining the level of efficacy against a disease or unwanted condition as disclosed herein in comparison to a subject (or group of subjects) that has not been administered said derivative or that has been administered a different amount of said derivative or administered said derivative under different administration protocols (such as, but not limited to, frequency of administration or amount of derivative administered).

The comparison may also be made between disclosed compounds to determine their relative levels of activity. The subjects are animals, preferably human, and may be those that are part of a clinical or pre-clinical trial or test of one or more of the compounds. The determination of the level of activity can be made in a variety of ways as would be known to the skilled practitioner for the diseases and unwanted conditions disclosed herein.

Biological Activity

In accordance with the present invention, compounds of formula I and II are useful for preventing and treating conditions associated with ischemic cell death, such as myocardial infarction, stroke, glaucoma, and other neurodegenerative conditions. Various neurodegenerative conditions which may involve apoptotic cell death, include, but are not limited to, Alzheimer's Disease, ALS and motor neuron degeneration, Parkinson's disease, peripheral neuropathies, Down's Syndrome, age related macular degeneration (ARMD), traumatic brain injury, spinal cord injury, Huntington's Disease, spinal muscular atrophy, and HIV encephalitis. The compounds described in detail above can be used in methods and compositions for imparting neuroprotection and for treating neurodegenerative diseases.

The compounds of formula I and II can be used in a pharmaceutical composition for the prevention and/or the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neurodegenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders, and septic shock, arthritis, fever, common cold, pain and cancer in a mammal, preferably a human, cat, livestock or a dog, comprising an amount of a compound of formula I or a pharmaceutically acceptable salt thereof effective in such prevention and/or treatment optionally with a pharmaceutically acceptable carrier.

Targets

A. PDE6 Delta (PDE6D)

The compounds described herein target PDE6, preferably PDE6D, in certain embodiments. PDE type 6 family members are associated with retinal phototransduction (Stryer, L, et al., *J. Biol. Chem.* 266:10711-14 (1991)). In phototransduction, photoreceptor cells absorb light to trigger a nerve signal via activation of an intracellular cascade of biochemical reactions leading to cGMP hydrolysis by PDE6. Decreases in cGMP result in closure of a membrane-bound cGMP-gated cation channel in the photoreceptor cell to generate a nerve signal. The dark state of the cell is recovered by PDE6 deactivation, guanylcyclase activation, and restoration of cGMP levels.

PDE6 is a tetrameric protein made up of two catalytic subunits (alpha and beta) and two inhibitory (gamma) subunits. Release of the gamma subunits from the PDE6 complex is mediated by transducin, which activates the enzyme. Reassociation of the gamma subunits is mediated by recoverin, which deactivates the enzyme. While PDE6 is associated primarily with disk membranes of outer rod segments in retinal cells, a soluble form of the enzyme contains a fourth (delta) subunit (Florio, S. K. et al. (1996) *J. Biol. Chem.* 271:24036-47).

The PDE6 holoenzyme exists as both membrane-associated and soluble forms, and only the membrane-associated form is active in phototransduction. Importantly, only the soluble form contains the PDE6D subunit. PDE6D regulates the subcellular localization and thus the activity of PDE6, and the release of PDE6 from membranes is mediated by PDE6D. Indeed, PDE6D has been observed to reduce light-induced cGMP hydrolysis in rod outer segments (Cook et al., J. Biol. Chem 276(7):5248-5255 (2001)), presumably by removing the PDE6 holoenzyme from the membrane. PDE6D solubilizes PDE6 by binding specifically to prenylated peptide sequences near the C-termini of the PDE6A and PDE6B subunits. In one. embodiment, the invention provides for treatment of visual impairment disorders, particularly those associated with the phototransduction signaling cascade through the modulation PDE6's participation in cGMP hydrolysis.

The PDE6 delta (PDE6D) is a 17 kDa subunit that has not been found in association with membrane bound PDE6 but has been observed to solubilize membrane-bound PDE6. This release of PDE6 from the rod membrane appears to be via delta subunit binding to the C-terminal portion of PDE6 and is thought to reduce the likelihood of PDE6 activation by membrane-bound transducing. The delta subunit is also hypothesized as providing another level of enzyme regulation.

The human PDE delta gene product (PDE6D) has been recognized as a chaperone for the catalytic PDE alpha and beta subunits. Prenylated PDE alpha and beta subunits have been found to be bound by PDE6D and to be solubilized from membranes possibly as a regulatory mechanism in the visual cascade. Retinitis pigmentosa (RP) is a hereditary retinal dystrophy characterized by impaired dark adaptation and severe reductions in visual acuity. The RP gene has been identified as the retinitis pigmentosa GTPase regulator (RPGR) protein, which has been observed to have binding affinity for members of the PDE6 family even in the absence of prenylation (Linari M, et al., *Proc. Natl. Acad. Sci. USA* 96:1315-1320 (1999)). PDE6D interacts with the retinitis pigmentosa GTPase regulator (RPGR) in a thermosensitive fashion. Interaction is abolished by mutations in the RCC1-domain of RPGR. In one embodiment, the invention provides for treatment of RP through the modulation of PDE6 interaction with RPGR and other molecules involved in the phototransduction cascade.

PDE6D is expressed in many cell types and has a general role in regulating the intracellular localization and transport of prenylated proteins, including H-Ras, Rheb, Rho6, Rac, Rap, and PDE6 (Hanzal-Bayer et al. EMBO J. 21(9):2095-2106 (2002) and Linari et al. Proc. Natl. Acad. Sci., USA 96(4):1315-1320). The role of PDE6D in regulating the membrane localization of these prenylated proteins is still unclear, but it has been proposed that PDE6D delivers proteins from endomembranes (endoplasmic reticulum and Golgi) to trafficking structures that ensure correct delivery to the ultimate membrane compartment.

PDE6D interacts with GTPases, a large super-family of proteins that play a major role at the cell membrane as molecular switches, active when GTP-bound and inactive when GDP-bound. The majority of these GTPases have a covalently attached prenyl group for anchorage to the intracellular side of the cell membrane. They function by shuttling between the membrane-anchored form and a free cytosolic form. The delta subunit can bind the isoprenylated region of the small Rab13 GTPase and displace it from the plasma membrane. (Marzesco et al., *J. Biol. Chem.* 273(35): 22340-22345 (1998)). In addition, PDE6D is capable of interacting with the C-terminal regions of both the Ras and Rap GTPases and regulating their association with the plasma membrane. For Ras binding PDE6D requires a prenylated region of the C-terminus. (Nancy et al., *J. Biol. Chem.* 277(17):15076-15084 (2002)).

PDE6D has also been observed to interact with H-Ras, Rheb, Rho6 and Gα (i1) and suggested as a transport factor for prenylated proteins, including subunits of PDE6 and small GTP-binding proteins. (Hanzal-Bayer et al. *EMBO J.* 21 (9):2095-2106 (2002)). cGMP PDE-specific inhibitors which act on PDE6 and PDE5 include zaprinast, desmethylsildenophil, vinopocetine, milrinone, amrinone, pimobendan, cilostamide, enoximone, peroximone, vesnarinone, rolipran, R020-1724, and dipyridamole. The compounds of the invention may be administered to treat medical disorders or diseases attributable to errant intracellular transport of prenylated proteins and/or GTP-binding proteins.

The biosynthetic pathways for prenyl groups (e.g. farnesyl and geranyl-geranyl) and cholesterol are overlapping and both require HMG-CoA reductase activity. PDE6D can also be considered an important component of the prenylation pathway since it regulates the transport and localization of prenylated proteins. Prenylated proteins have critical roles in signal transduction (e.g. Ras), and there is evidence suggesting a role for prenylated proteins in neurotoxicity (Liao J. K. J. Clinical Investigation, 110: 285-288 (2002)). Thus, compounds that bind to PDE6D and modulate its activity should perturb directly the localization and function of prenylated proteins, and be useful in the prevention and treatment of conditions and diseases.

PDE6D has been observed to reduce light-induced cGMP hydrolysis in rod outer segments (Cook et al., J. Biol. Chem 276(7):5248-5255 (2001)). The delta subunit interacts directly with the prenylated C-terminal regions of two G-protein coupled rhodopsin kinases, GRK1 and GRK7 that are specific to photoreceptors. (Zhang et al., J. Biol. Chem. 279(1):407-413 (2004)). Rhodopsin kinases phosphorylate membrane photoreceptors to regulate phototransduction. In one embodiment, the invention provides for a method of treatment of visual impairment through modulation of PDE6 interaction with rhodopsin kinases and other molecules involved in the phototransduction signaling cascade.

PDE6D has also been found to interact with other proteins absent post-translational prenylation. For example, PDE6D interacts with the unprenylated region of the retinitis pigmentosa GTPase regulator (RPGR) protein. (Linari et al., *Proc. Natl. Acad. Sci., USA* 96(4):1315-1320 (1999)). In addition, the delta subunit can interact with two members of the GTPase subfamily known as Arl proteins or the ARF (ADP-ribosylation factor)-like proteins. PDE6D interacts with the Arl2 and Arl3 proteins independent of any post-translational modification (Hanzal-Bayer et al., *EMBO J.* 21(9):2095-2106 (2002) and Linari et al., *FEBS Letter* 458:55-59 (1999)). Based on their structure-function studies, Hanzal-Bayer et al., have postulated that the delta subunit is a transport factor for membrane bound prenylated proteins, such as the GTP binding molecules, and Arl2/3 serves as the mediator of the delta subunit in the release and/or uptake of prenylated proteins. In one embodiment, the invention provides a method of treating a PDE6-related and/or GTP-binding protein-related disorder through the modulation of Arl2/3 molecule activity. The use of the term "PDE6" and references to its activities and/or modulation, herein, is intended to also include activity and/or modulation of PDE6D without an interaction with PDE6.

B. Quinone Reductase 2 (QR2)

The compounds described herein target QR2 in certain embodiments. Quinone reductase 2 (QR2), also known as NAD(P)H:(quinine-acceptor) oxidoreductase (NQO2), has been identified as a FAD-dependent flavoenzyme (Liao et al. (1962) *J. Biol. Chem.* 237:2981-2987), related to NQO1 (dioxin-inducible cytosolic form of NAD(P)H:(quinine-acceptor) oxidoreductase, previously known as DT diaphorase) and identified by EC 1.6.99.2 (Zhao et al. (1997) *Proc. Natl. Acad. Sci, USA* 94:1669-1674), a puromycin aminonucleoside-binding protein (Kodama et al. (1997) *Nephrol. Dial. Transplant.* 12:1453-1460), and the melatonin-binding site MT3 (Nosjean et al. (2000) *J. Biol. Chem.* 275(40): 31311-31317). As a flavoenzyme and related to NQO1, QR2 may catalyze 2-electron reductions of various compounds, such as quinines, quinine imines, oxidation-reduction dyes. Jaiswal et al. (1994, *J. Biol. Chem.* 269(20):14502-14508) describe QR2 as catalyzing 4-nitroreduction of the antitumor compound CB 10-200 but not acting on 2,6-dichlorophenolindophenol or menadione, which are metabolized by NQO 1. QR2 is believed to be cytosolic and was identified as being expressed in human heart, lung, liver, skeletal muscle, kidney, and pancreas tissues but not in placenta. This is in contrast to $NQO_1$, which is expressed in all tissues.

QR2 reduces quinines by N-ribosyl- and N-alkyldihydronicotinamides but not by NADH, NADPH, or NMNH (reduced nicotinamide mononucleotide or NMN) and is weakly inhibited by dicumarol or Cibacron blue. QR2 is a homodimer and is strongly inhibited by benzo[α]pyrene. Zhao et al. 1997 note that QR2 may play a role in the reductive bioactivation of quinone and nitro group-containing cytotoxic agents. Graves et al. (2002, *Mol. Pharmacol.* 62(6):1364-1372) identified human QR2 as a quninoline-binding protein.

The compounds of the invention do not interact with QR2 but can affect QR2 activity such as the bioactivation of quinone and nitro group-containing cytotoxic agents, particularly in heart, brain lung, liver, skeletal muscle, kidney, and pancreas tissues. The use of compounds that inhibit QR2 activity may have a protective effect against toxic and/or cytotoxic agents, particularly in the tissues described above.

C. Calbindin-2 (CLB2)

Calretinin (also known as calbindin-2, CR, CLB2, and CALB2) is a calcium binding protein of the EF-hand family related to calbindin D-28K and calmodulin. Calretinin has been observed as a useful marker of ovarian sex cord-stromal tumours as well as neoplasms that have been found therewith. (See abstract of *Histopathology* 38(5):403-8 (2001)). The presence of calretinin has also been correlated with neuronal survival in some neurodegenerative diseases, including Alzheimer's Disease and a rat model of Parkinson's disease.

Calbindin is a $Ca^{2+}$-binding protein and is mainly distributed in friable site of the brain against ischemic disease. Calbindin is reported to possess buffering effects for a rise in cytotoxic intracellular $Ca^{2+}$ concentration. [Lacopino et al., Neurodegeneration, 3: 1 (1994); Mattson et al., Neuron, 6: 41 (1991)]. Accordingly, the modulation of the activity of calbindin is expected to provide neuroprotective effects against ischemic disorders. That is, it is expected that modulation of the activity of calbindin would be effective therapeutic and improving agents for the alleviation or treatment of symptoms such as sequelae of cerebral infarction, sequelae of intracerebral hemorrhage, sequelae of cerebral arteriosclerosis, senile dementia, sequelae of head trauma, Alzheimer's disease, Parkinson's disease, amyotrophic lateral sclerosis, ovarian sex cord-stromal tumours, neoplasms, and the like.

Clinical Uses of Pyrrole Compounds

The pyrrole compounds and other compounds of the invention may be used to treat a variety of diseases and unwanted conditions. In some embodiments, the compounds described herein are used in the treatment of PD E6-related, QR2-related and CLB2-related conditions. It is not intended that the pyrrole compounds of the invention only act by modulating PDE6, QR2, or CLB2. Hence, these compounds can be used to treat diseases in which cellular constituents other than PDE6, QR2, or CLB2 play a role. Diseases that may be treated with the compounds described herein include, but are not limited to, cerebral accident (or cerebrovascular accident, including stroke), inflammation (including inflammation due to autoimmune diseases), multiple sclerosis, blood vessel growth (angiogenesis), bone formation/bone growth, immune system stimulation, acute coronary syndromes (including myocardial infarction, non-Q-wave myocardial infarction and unstable angina), and cardiovascular disease. In one aspect, the compounds of the invention may be used to reduce the likelihood of stroke or cardiovascular disease, and to decrease damage following brain and/or heart infarction or other trauma. In another aspect, the compounds may be used to reduce the severity of damage caused by stroke or cardiovascular disease in a subject. Non-limiting examples of the benefit provided by the compounds include decreased brain and/or heart infarction.

The term "PDE6-related condition", "QR2-related condition" or "CLB2-related condition" as used herein refers to a condition in which directly or indirectly modulating the activity and/or production of a PDE6, QR2 or CLB2 molecule, respectively, is desirable. This modulation includes modulation of one or more molecules in the upstream or downstream signaling cascades of PDE6, QR2 or CLB2. For example, a PDE6-related condition may involve the PDE6D subunit, over-production or unwanted production of one or more prenylated PDE6 subunits, such as PDE6D, prenylated PDE6α or PDE6β, or other chemical messengers of cell signaling pathways associated with phototransduction (including responses to and expression of PDE6 alpha and PDE6 beta). In certain embodiments, the enzyme HMG CoA reductase plays a minimal role in the PDE6-related condition, QR2-related condition or CLB2-related condition.

In some embodiments, the methods of the present invention employ a PDE6 modulating compound. The term "PDE6 modulating compound" as used herein and its grammatical conjugations refer to a compound that preferably modulates PDE6, for example by binding to PDE6, preferably by binding to PDE6D. For example, a PDE6 modulating compound may modulate one or more prenylated PDE6 subunits, such as PDE6D, prenylated PDE6α or PDE6β, or other chemical messengers of cell signaling pathways associated with phototransduction (including responses to and expression of PDE6 alpha and PDE6 beta). In some embodiments the term "preferable modulation" and its grammatical conjugations refers to a specific modulation of PDE6. In other embodiments, the term refers to preferable modulation of PDE6 with minimal modulation with HMG Co A reductase. The term "minimal modulation" refers to essentially no modulation, but does not require a complete lack of modulation; preferably, it refers to essentially no observable or measurable activity. In treatment scenarios, the "minimal modulation" refers to modulation that is not sufficient to produce a therapeutic and/or prophylactic benefit in a condition caused by the activity that is not being modulated.

Modulating the activity of a PDE6, QR2 or CLB2 molecule includes reducing, increasing, or stabilizing the activity of these molecules. Reducing the activity of PDE6, QR2 or CLB2 is also referred to as "inhibiting" the molecule. The term "inhibits" and its grammatical conjugations, such as "inhibitory," is not intended to require complete reduction in PDE6, QR2 or CLB2 activity. Such reduction is preferably by at least about 50%, at least about 75%, at least about 90%, and more preferably by at least about 95% of the activity of the molecule in the absence of the inhibitory effect, e.g., in the absence of an inhibitor, such as a compound of the invention. Most preferably, the term refers to an observable or measurable reduction in activity. In treatment scenarios, preferably the inhibition is sufficient to produce a therapeutic and/or prophylactic benefit in the condition being treated. The phrase "does not inhibit" and its grammatical conjugations does not require a complete lack of effect on the activity. For example, it refers to situations where there is less than about 20%, less than about 10%, and preferably less than about 5% of reduction in PDE6, QR2 or CLB2 activity in the presence of an inhibitor such as a compound of the invention.

The PDE6-modulating agents of the invention can be administered to a mammalian subject to treat a disorder by modulating the binding of PDE6D to prenylated GTPases, thereby modulating GTPase-dependent signal transduction pathways. The disruption of GTPase-dependent pathways contributes to a variety of medical conditions, such as vascular hyperplasia, thrombin-induced cell death, the pathogenesis and progression of bladder cancer, chronic inflammatory disease, endothelial dysfunction in cardiovascular disease, cardiac hypertrophy, a change in cerebral blood flow to ischemic regions of the brain, phagocytosis of amloid-beta fibrils in Alzheimer's disease patients, immunodeficiency disorders and increased free radical production in aortic vascular smooth muscle cells.

PDE6-related, QR2-related or CLB2-related conditions can include neurodegenerative diseases, including ischemic stroke, basal ganglia or Parkinson's disease, epilepsy or brain or spinal cord ischemia or trauma; Alzheimer's disease, dementia, diabetic peripheral neuropathy, multiple sclerosis, amyotrophic lateral sclerosis, traumatic brain injury, spinal cord injury, Huntington's disease, heart failure (e.g. congestive heart failure, acute heart failure, cardiac hypertrophy, etc.) or renal diseases.

PDE6-related, QR2-related or CLB2-related conditions can include visual impairment disorders, including macular degeneration, amblyopia, Blepharitis, Bietti's Crystalline Dystrophy, corneal disease, diabetic eye disease, glaucoma, histoplasmosis, and retinitis pigmentosa. PDE6-related, QR2-related or CLB2-related conditions can include cardiovascular-related conditions, including atherosclerosis, myocardial infarction, congestive heart failure, ischemic-reperfusion injury and other vascular inflammatory conditions. PDE6-related, QR2-related or CLB2-related conditions can also include proliferative disorders, including cancers, e.g., leukemia, melanoma, Non-Hodgkins Lymphoma, as well as bladder, breast, colon, endometrial, head and neck, lung, ovarian, prostate and rectal cancers.

PDE6-related, QR2-related or CLB2-related conditions can also include neurological deficits that develop from a stroke-induced impairment of blood flow to the brain regardless of cause. Potential causes include, but are not limited to, thrombosis, hemorrhage and embolism. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

In one embodiment, the PDE6-modulating agent modulates the activity small GTP binding protein Rho in its role in cell proliferation. It has been reported that Rho proteins are more abundant in tumor bladders than in non-tumor bladders and upregulated in ovarian carcinomas (Kamai T, et al., *Clin. Cancer Res.* July; 9(7):2632-41 (2003) and Horiuchi A, et al., *Lab Invest.* 2003 June; 83(6): 861-70 (2003)).

A disruption in Rho GTP binding activity has been shown to have the neuroprotective effect of increasing cerebral blood flow to ischemic regions of the brain (Laufs U, et al., *J. Clin. Invest.* 106(1):15-24 (2000)). The study demonstrated that under absent or decreased rho-dependent actin cytoskeleton stress fiber formation, eNOS was upregulated and the severity of cerebral ischemia was decreased. An embodiment of the invention provides for the treatment of ischemic stroke by modulation of Rho by a compound of the invention.

Researchers have reported that the cardiac hypertrophy, which requires intracellular oxidation may be reduced by statin-induced inhibition of post-translational modification of the small G proteins of the Rho family (Takemoto M, et al., *J. Clin. Invest.* 108(10):1429-37 (2001)). Takemoto M, et al. observed that an inhibition of the Rho isoprenylation produced an intracellular antioxidant effect and inhibit cardiac hypertrophy. One embodiment of the invention provides for the treatment of cardiac hypertrophy by modulation of Rho by a compound of the invention.

In another embodiment, the PDE6-modulating agent modulates the activity of the small GTP binding protein Rac in its role in Alzheimer's disease. Rac has been observed to participate in the phagocytosis of amyloid-beta fibrils from extracellular senile plaques. (Kitamura Y, et al, *J. Pharmacol. Sci.* 92(2):115-23 2003)).

Methods of Treatment

An aspect of the present invention relates to methods of using the pyrrole compounds of the present invention per se, pharmaceutical compositions and kits comprising compounds described herein to treat PDE6-related, QR2-related, and CLB2-related conditions.

Another aspect of the invention relates to the method of using atorvastatin to treat a PDE6-related condition. The PDE6D-related conditions treated include conditions in which direct or indirect modulation of the activity and/or production of a PDE6D molecule is desirable. This modulation includes modulation of one or more molecules in the upstream or downstream signaling cascades of PDE6D. For example, a PDE6D-related condition may involve overproduction or unwanted production of PDE6D subunits. When atorvastatin is used it is preferred that the conditions treated have a minimal HMG CoA reductase role. Preferably, the administration of atorvastatin produces a beneficial effect by preferably modulating PDE6. Due to the properties of atorvastatin, an effect on HMG CoA reducatase activity would be anticipated, but in some embodiments, it is not this activity that produces a beneficial effect in the condition being treated. In certain embodiments, the effect of atorvastatin in the condition being treated or in the method in which it is employed is not reversed by the addition of farnesyl pyrophosphate, geraylgeranyl pyrophosphate, and/or mevalonate. In certain embodiments, atorvastatin is used to treat NQ2 and/or CLB2-related conditions.

The present invention provides methods, pharmaceutical compositions, and kits for the treatment of subjects. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like.

The term "treating" as used herein includes achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For example, a PDE6D-modulating agent may provide a therapeutic benefit not only when Alzheimer's disease is eradicated, but also when an improvement is observed in the patient with respect to other disorders or discomforts that accompany Alzheimer's, like dementia. Similarly, inhibitors of the present invention can provide therapeutic benefit in ameliorating other symptoms associated with PDE6-related, QR2-related, and CLB2-related conditions, e.g., inflammatory, autoimmune, cancerous, impaired vision and/or neurodegenerative conditions, including redness, rashes, swelling, itching, irritation, dryness, scaling, flaking, pain, temperature increase, loss of normal function, and the like.

For prophylactic benefit, a composition of the invention may be administered to a patient at risk of developing a PDE6-related, QR2-related and CLB2-related, or to a patient reporting one or more of the physiological symptoms of such conditions, even though a diagnosis of the condition may not have been made.

As one of skill in the art will recognize, the compounds, such as the pyrrole compounds, can be administered before, during or after the occurrence of a condition or a disease, and the timing of administering the composition containing a pyrrole compound can vary. Thus, for example, the pyrrole compounds can be used as a prophylactic and can be administered continuously to subjects with a propensity to conditions and diseases in order to prevent the occurrence of the disorder. The pyrrole compounds can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 min. to about 5 hours, a pill, a capsule, transdermal patch, buccal delivery, and the like, or a combination thereof. A pyrrole compound is preferably administered as soon as is practicable after the onset of a condition or a disease, such as, e.g., a stroke, is detected or suspected, and for a length of time necessary for the treatment of the disease, such as, for example, from about 1 month to about 3 months. As one of skill in the art will recognize, the length of treatment can vary for each subject, and the length can be determined using the known criteria. For example, for stroke, typically, the pyrrole compound will be administered for at least 2 weeks, preferably about 1 month to about 1 year, and more preferably from about 1 month to about 3 months. Chronic administration of the pyrrole compounds can be used to promote recovery following a CVA or in a neurodegenerative disorder.

In the case of a CVA, such as stroke, and in one embodiment of the invention, a pyrrole compound of the invention can be used following an initial stroke to decrease the frequency and/or severity of damage, such as from brain infarction, that result from subsequent strokes. The invention thus provides methods for decreasing the damage resulting from stroke (post stroke trauma). The invention thus provides for decreasing the frequency of and/or damage from post myocardial trauma.

In another aspect of the invention, the compounds of the invention that bind the PDE6D, QR2 and/or CLB2 targets are used to treat or prevent conditions as mediated by PDE6, QR2 and/or CLB2 in vivo. In some embodiments, a compound affects the function and/or activity of PDE6D, QR2 and/or CLB2 such that it may be administered to a mammalian subject, preferably human, in need of a change in the function and/or activity of PDE6D, QR2 and/or CLB2. The invention thus provides for the treatment of a disease or undesirable condition mediated by insufficient or unwanted, or in the alternative excess, PDE6D, QR2 and/or CLB2 activity, including the binding of PDE6D to its binding partner(s) or its association with other protein(s), particularly prenylated proteins. The compounds of the invention are expected to include those useful for the modulation of cellular signaling cascades mediated by PDE6D.

In some embodiments, methods of modulating the activity of the targets based upon alterations in the intracellular expression thereof are provided by the invention. These include increasing the expression of the targets in cells in need thereof as well as reducing expression of the targets in cells in need of such reduction. Non-limiting methods to increase expression include the use of recombinant expression vectors as well as agents that increased expression of endogenous sequences encoding a target of the invention. Non-limiting methods to decrease expression include the use of RNA interference, antisense and ribozymes mediated means, and the use of agents that decrease expression of endogenous sequences encoding a target of the invention.

In yet another embodiment, the invention provides methods for determining the level of stimulation or inhibition by a target binding compound in the treatment of a disease or unwanted condition. Such methods include the administration of a target binding compound to a subject followed by determination of the level of stimulation or inhibition mediated by said compound in comparison to a subject who has not been administered said compound or to a subject that has been administered a different amount or concentration of said compound. The level of stimulation or inhibition may be determined by the efficacy of the compound in the treatment of the disease or unwanted condition. Alternatively, the level of inhibition may be determined by the inhibition of a phenotype mediated by the target of said compound in said subject, optionally in the absence of comparison to another subject. These methods may be practiced repeatedly, with a variety of amounts or concentrations of the compound to determine the level of stimulation or inhibition over a range of conditions. The methods may also be used to determine that the level of stimulation or inhibition is undetectable.

An exemplary method of determining the level of stimulation or inhibition of a target binding compound may comprise
a) administering a target binding (stimulator or inhibitor) compound to a subject;
b) determining the level of stimulatory or inhibitory activity or efficacy against a disease or unwanted condition as disclosed herein in comparison to a subject (or group of subjects) that has not been administered said compound or that has been administered a different amount of said compound or administered said compound under different administration protocols (such as, but not limited to, frequency of administration or amount of compound administered).

The comparison may also be made between different target binding compounds to determine their relative levels of activity. The subjects are mammalian, preferably human, and may be those that are part of a clinical or pre-clinical trial or test of one or more target-binding compound. The determination of the level of stimulatory or inhibitory activity may also be performed outside, or after, a clinical trial to identify the level of inhibition by a target binding compound and can be made in a variety of ways as would be known to the skilled practitioner for a disease or unwanted condition.

The compounds of the invention, such as the PDE6D, QR2 or CLB2 modulating compounds, may be administered to a subject upon determination of the subject as having a disease or unwanted condition that would benefit by treatment with said compound. The determination may be made by medical or clinical personnel as part of a diagnosis of a disease or condition in a subject. Preferred embodiments include methods for the use of a PDE6D, QR2 and/or CLB2 binding compound to provide minimal inhibition of HMG-CoA Reductase activity. Exemplary effects include, but are not limited to, the treatment of cerebral accident (cerebrovascular accident or CVA), including stroke; inflammation (such as from autoimmune diseases); multiple sclerosis; and cardiovascular disease, including the reduction of post-myocardial infarction trauma. The PDE6D, QR2 and/or CLB2 modulating compound may also be used in the prevention of such conditions, particularly in the cases of CVA such as in subjects that suffered one or more strokes or in subjects that have been diagnosed by medical personnel as at risk for a CVA, such as a stroke.

The term "stroke" broadly refers to the development of neurological deficits associated with impaired blood flow to the brain regardless of cause. Potential causes include, but are not limited to, thrombosis, hemorrhage and embolism. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

In the case of a CVA, such as stroke, and in one embodiment of the invention, a compound of the invention may be used following an initial stroke to decrease the frequency and/or severity or damage, such as from brain infarction, that result from subsequent strokes. The invention thus provides methods for decreasing the damage resulting from stroke (post stroke trauma) using compounds that bind PDE6D, QR2 and/or CLB2.

In the case of cardiovascular disease, and in one embodiment of the invention, a compound of the invention may be used following an initial heart attack to decrease the frequency and/or severity or damage, such as from myocardial (heart) infarction (commonly referred to as heart attack), that result from subsequent heart attack(s). The invention thus provides for decreasing the frequency of and/or damage from post myocardial trauma. The compounds of the invention may also be used to treat conditions such as inflammation and multiple sclerosis.

Other non-limiting examples of PDE6D activity affected by compounds of the invention include the binding of PDE6D to the catalytic PDE alpha and/or beta subunits; and the binding of PDE6D to prenylated proteins. The invention thus provides methods for the modulation of the signaling cascade mediated by phosphodiesterase 6 (as well as other signaling cascades in which PDE6D is a component), such as, but not limited to, the cascade of rod outer segment membranes in the visual system of animals.

Additionally, PDE6D binding compounds are expected to play a role in the modulation of phosphodiesterase-mediated activities in a variety of cell types beyond retinal cells. Non-limiting embodiments of the invention include the use of PDE6D binding compounds that inhibit phosphodiesterase-mediated activities such as those inhibited by the following: zaprinast, desmethylsildenophil, vinopocetine, milrinone, amrinone, pimobendan, cilostamide, enoximone, peroximone, vesnarinone, rolipran, R020-1724, and dipyridamole. A PDE6D inhibiting compound may also be used in combination with these agents. Therefore, the methods of the present invention may be used to treat a subject having a disorder characterized by aberrant or undesired phosphodiesterase, especially PDE6, activity by administering a PDE6D inhibiting compound and/or another inhibitor.

In one embodiment, the disorder characterized by aberrant or undesired PDE6D activity is a disorder characterized by insufficient levels of membrane-bound PDE6.

The invention also provides for the use of a PDE6D binding compound to affect its binding to members of the ras superfamily and rab family of proteins, including H-Ras, Rheb, Rho6, and Rab13. The compounds of the invention can also be used to affect PDE6D binding to Gα(i1) and the Arf-like (Arl) proteins Arl2 and Arl3. Arf (ADP-ribosylation factor) subfamily members are regulators of vesicle formation in intracellular traffic. Rab13 has been identified as being involved in vesicular trafficking and associated with tight junctions in epithelial cells. The PDE6D modulating compounds of the invention may thus be used to treat diseases and unwanted conditions mediated by proteins which associate with PDE6D, including H-Ras, Rheb, Rho6, Rab13, Gα(i1), Arl2, and Arl3. Non-limiting examples includes cancer, holoprosecncephaly type 3, and sacral agenesis.

Non-limiting examples of QR2 activity affected by compounds of the invention include the binding of QR2 to quinoline and the bioactivation of quinone and nitro group-containing cytotoxic agents. The invention thus provides methods for the modulation of the bioactivation of compounds mediated by QR2.

The methods of the invention may comprise the administration of a PDE6D, QR2 and/or CLB2 binding compound alone or in combination with one or more other molecule or other agent suitable for a disease being treated. The subject is preferably human, and repeated administration over time is within the scope of the present invention.

Such combination methods can be used to treat PDE6-related, QR2-related or CLB2-related conditions, as described in detail above. The methods may comprise the administration of the compounds of the invention in combination with other therapeutic agents. The choice of therapeutic agents that can be co-administered with the compositions of the invention will depend, in part, on the condition being treated. For example, for treating arteriosclerosis, or other cardiovascular condition, a pyrrole compound of some embodiments of the invention can be used in combination with an anticoagulant, a cholesterol lowering drug, a vasodilator, a diuretic, and/or an angiotensin converting enzyme inhibitor, and the like. With respect to treating Alzheimer's disease-related conditions, a pyrrole compound of the invention can be used in combination with an acetylcholinesterase inhibitor or a glutamate receptor antagonist, and the like.

The above generally relates to methods of targeting PDE6D, QR2 or CLB2 expression or activity for therapeutic purposes. Accordingly, in an exemplary embodiment, the methods of the invention involves contacting a cell with a PDE6D, QR2 or CLB2 binding compound that stimulates or inhibits one or more of the activities of PDE6D, QR2 or CLB2 protein activity associated with the cell. These methods can be performed in vitro (e.g., by culturing the cell with the agent) or, alternatively, in vivo (e.g, by administering the agent to a subject). They may also be performed ex vivo, as in the case of cells obtained from a subject and treated in vitro followed by their return to the subject.

The identification of PDE6D, QR2 and CLB2 as the targets for treating diseases and unwanted conditions permits a number of therapeutic approaches to the treatment thereof. Accordingly, therapeutic approaches that stimulate or inhibit PDE6D, QR2 and CLB2 function and activity are provided by the invention. These therapeutic approaches generally fall into two classes. One class comprises various methods for affecting the binding or association of a PDE6D, QR2 or CLB2 protein with its binding partner or with other proteins. Another class comprises a variety of methods for affecting the transcription of the PDE6D, QR2 or CLB2 gene or translation of PDE6D, QR2 or CLB2 mRNA.

In one preferred embodiment of the invention, a small molecule identified as binding PDE6D, QR2 or CLB2 may be used to stimulate or inhibit PDE6D, QR2 or CLB2 function or activity. Alternatively, PDE6D, QR2 and CLB2 may be targeted by antibody-based therapeutic strategies. A number of antibody strategies are known in the art for targeting intracellular molecules, including the intracellular expression of single chain antibodies. Antibodies can be introduced into a patient such that the antibody binds to PDE6D, QR2 or CLB2 and inhibits a function, such as an interaction with a binding partner. Alternatively, the antibody affects ligand binding or signal transduction pathways mediated by PDE6D, QR2 or CLB2.

The present invention also comprises various methods and compositions for inhibiting the transcription of PDE6D, QR2 or CLB2 encoding sequences. Similarly, the invention also provides methods and compositions for inhibiting the translation of PDE6D, QR2 or CLB2 mRNA into protein.

In one approach, a method of inhibiting the transcription of PDE6D, QR2 or CLB2 encoding sequences comprises contacting the sequences with an antisense polynucleotide. In another approach; a method of inhibiting PDE6D, QR2 or CLB2 mRNA translation comprises contacting the mRNA with an antisense polynucleotide or triggering post-transcriptional gene silencing (PTGS, including RNA interference) as known in the art. In another approach, a PDE6D, QR2 or CLB2 specific ribozyme is used to cleave the PDE6D, QR2 or CLB2 mRNA message, thereby inhibiting translation. Such antisense and ribozyme based methods can also be directed to the regulatory regions of PDE6D, QR2 or CLB2 encoding sequences, such as the promoter and/or enhancer elements. Similarly, proteins and/or small molecules (less than 5 kDa) capable of inhibiting a PDE6D, QR2 or CLB2 gene transcription factor are used to inhibit PDE6D, QR2 or CLB2 mRNA transcription.

Gene transfer and gene therapy technologies can be used to deliver therapeutic polynucleotide molecules (i.e., antisense, ribozyme, polynucleotides encoding intrabodies and other inhibitory molecules) to cells expressing PDE6D, QR2 or CLB2. A number of gene therapy approaches are known in the art. Recombinant vectors encoding PDE6D, QR2 or CLB2 antisense polynucleotides, ribozymes, siRNAs, factors capable of interfering with PDE6D, QR2 or CLB2 transcription, and so forth, can be delivered to target cells using such gene therapy approaches.

In vivo, the effect of a PDE6D, QR2 or CLB2 therapeutic composition can be evaluated in a suitable animal model. In vivo assays that evaluate the inhibition of PDE6D, QR2 or CLB2 function or activity are also useful in evaluating therapeutic compositions.

The inhibitors of the invention may also be used in prophylactic methods to prevent in a subject, a disease or unwanted condition associated with PDE6D, QR2 or CLB2 expression or activity, by administering to the subject an agent which affects PDE6D, QR2 or CLB2 expression or at least one PDE6D, QR2 or CLB2 activity. Subjects at risk for a disease which is caused or contributed to by aberrant PDE6D, QR2 or CLB2 expression or activity can be identified by any appropriate prognostic assays as known in the field. Administration of a prophylactic agent can occur prior to the manifestation of symptoms characteristic of aberrant PDE6D, QR2 or CLB2 levels, such that a disease or condition is prevented or, alternatively, delayed in its progression.

As used herein, an effective amount of a compound or agent refers to an amount sufficient to achieve its intended purpose. Determination of the effective amounts is well within the capability of those skilled in the art based upon the achievement of a desired effect. An effective amount will depend on factors including, but not limited to, the size of a subject and/or the degree to which the disease or unwanted condition from which a subject suffers has progressed. The effective amount will also depend on whether the compound or agent is administered to the subject in a single dosage or periodically over time.

Formulations, Routes of Administration, and Effective Doses

The compounds of the invention, such as the PDE6D, QR2 and CLB2 modulating compounds, are preferably used to prepare a medicament, such as by formulation into pharmaceutical compositions for administration to a subject using techniques generally known in the art. A summary of such pharmaceutical compositions may be found, for example, in Remington's Pharmaceutical Sciences, Mack Publishing Co., Easton, Pa. The compounds of the invention can be used singly or as components of mixtures. Preferred forms of the compounds are those for systemic administration as well as those for topical or transdermal administration. Formulations designed for sustained and/or delayed release are also with the scope of the invention.

Such pharmaceutical compositions can be used to treat diseases, such as PDE6-related, QR2-related or CLB2-related conditions, as described in detail above. If necessary or desirable, the modulator or inhibitor may be administered in combination with other therapeutic agents. The choice of therapeutic agents that can be co-administered with the compositions of the invention will depend, in part, on the condition being treated. For example, for treating arteriosclerosis, or other cardiovascular condition, a pyrrole compound of some embodiments of the invention can be used in combination with an anticoagulant, a cholesterol lowering drug, a vasodilator, a diuretic, and/or an angiotensin converting enzyme inhibitor, and the like. With respect to treating Alzheimer's disease-related conditions, a pyrrole compound of the invention can be used in combination with an acetylcholinesterase inhibitor or a glutamate receptor antagonist, and the like.

The modulators may be administered per se or in the form of a pharmaceutical composition wherein the active compound(s) is in an admixture or mixture with one or more pharmaceutically acceptable carriers, excipients or diluents. Pharmaceutical compositions for use in accordance with the present invention may be formulated in conventional manner using one or more physiologically acceptable carriers compromising excipients and auxiliaries, which facilitate processing of the active compounds into preparations that can be used pharmaceutically. Proper formulation is dependent upon the route of administration chosen. The modulators useful in the present invention can be delivered to the patient using a number of routes or modes of administration, including oral, buccal, topical, rectal, transdermal, transmucosal, subcutaneous, intravenous, and intramuscular applications, as well as by inhalation.

Methods for the preparation of compositions comprising the pyrrole compounds of the invention include formulating the derivatives with one or more inert, pharmaceutically acceptable carriers to form either a solid or liquid. Solid compositions include, but are not limited to, powders, tablets, dispersible granules, capsules, cachets, and suppositories. Liquid compositions include solutions in which a pyrrole compound is dissolved, emulsions comprising a pyrrole compound, or a solution containing liposomes, micelles, or nanoparticles comprising a pyrrole compound as disclosed herein.

Compounds of this invention may also be integrated into foodstuffs, e.g, cream cheese, butter, salad dressing, or ice cream to facilitate solubilization, administration, and/or compliance in certain patient populations.

The pyrrole compounds of the invention may be labeled isotopically (e.g. with a radioisotope) or by another other means, including, but not limited to, the use of chromophores or fluorescent moieties, bioluminescent labels, or chemiluminescent labels. The compositions may be in conventional forms, either as liquid solutions or suspensions, solid forms suitable for solution or suspension in a liquid prior. to use, or as emulsions. Suitable excipients or carriers are, for example, water, saline, dextrose, glycerol, alcohols, aloe vera gel, allantoin, glycerin, vitamin A and E oils, mineral oil, propylene glycol, PPG-2 myristyl propionate, and the like. Of course, these compositions may also contain minor amounts of nontoxic, auxiliary substances, such as wetting or emulsifying agents, pH buffering agents, and so forth.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for administration.

Aqueous suspensions may contain a compound of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

For injection, the compounds of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P. These compounds may also be formulated for transmucosal administration, buccal administration, for administration by inhalation, for parental administration, for transdermal administration, and rectal administration.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In some embodiments, pharmaceutical compositions comprising compounds of the present invention exert local and regional anti-inflammatory effects when administered topically or injected at or near particular sites of inflammation. For example, ocular allergic, inflammatory and/or autoimmune conditions can be effectively treated with ophthalmic solutions, suspensions, ointments or inserts comprising one or more compounds of the present invention. Allergic, inflammatory and/or autoimmune conditions of the ear can be effectively treated with otic solutions, suspensions, ointments or inserts comprising one or more compounds of the present invention. Allergic, inflammatory and/or autoimmune conditions of the skin and skin structures can be effectively treated with skin ointments comprising one or more compounds of the present invention in an oleaginous hydrocarbon base, an anhydrous absorption base, a water-in-oil absorption base, an oil-in-water water-removable base and/or a water-soluble base. Gastrointestinal allergic, inflammatory and/or autoimmune conditions can be effectively treated with orally- or rectally delivered solutions, suspensions, ointments, enemas and/or suppositories comprising one or more compounds of the present invention. Respiratory allergic, inflammatory and/or autoimmune conditions can be effectively treated with aerosol solutions, suspensions or dry powders comprising one or more compounds of the present invention.

For example, for treating inflammatory and/or autoimmune conditions, a cream comprising a compound of the invention may be topically applied to the affected site, for example, sites displaying red plaques or dry scales in psoriasis, or areas of irritation and dryness in dermatitis. As another example, for treating inflammatory bowel disease, a suppository formulation of a compound disclosed herein can be used. In such embodiments, the active ingredient produces a benefit locally at or near the site of application, rather than systemically, by modulating PDE6, QR2 or CLB2, e.g., PDE6D.

Direct topical application, e.g., of a viscous liquid, gel, jelly, cream, lotion, ointment, suppository, foam, or aerosol spray, may be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations may also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983.

In some preferred embodiments, the compounds of the present invention are delivered in soluble rather than suspension form, which allows for more rapid and quantitative absorption to the sites of action. In general, formulations such as jellies, creams, lotions, suppositories and ointments can provide an area with more extended exposure to the compounds of the present invention, while formulations in solution, e.g., sprays, provide more immediate, short-term exposure.

The formulations also may comprise suitable solid or gel phase carriers or excipients that increase penetration or help delivery of inhibitory compounds of this invention across the permeability barrier of the skin. Many of these penetration-enhancing compounds are known in the art of topical formulation. Examples of such carriers and excipients include humectants (e.g., urea), glycols (e.g., propylene glycol and polyethylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, ORGELASE, calcium carbonate, calcium phosphate, various sugars, starches, cellulose derivatives, gelatin, other polymers and water. In some embodiments, the pharmaceutical compositions will include one or more penetration enhancers such as water, methanol, ethanol, 2-propanol, dimethyl sulfoxide, decylmethyl sulfoxide, tetradecylmethyl sulfoxide, 2-pyrrolidone, N-methyl-2-pyrrolidone, N-(2-hydroxyethyl)pyrrolidone, laurocapram, acetone, dimethylacetamide, dimethylformamide, tetrahydrofurfuryl alcohol, L-α-amino acids, anionic surfactants, cationic surfactants, amphoteric surfactants, nonionic surfactants, fatty acids, fatty alcohols, clofibric acid amides, hexamethylene lauramide, proteolytic enzymes, α-bisabolol, d-limonene, urea, N,N-diethyl-m-toluamide, and the like.

In some embodiments, the pharmaceutical compositions will include one or more antimicrobial preservatives such as quaternary ammonium compounds, organic mercurials, p-hydroxy benzoates, aromatic alcohols, chlorobutanol, and the like.

Pharmaceutical compositions suitable for use in the present invention include compositions wherein the active ingredients are present in an effective amount, i.e., in an amount effective to achieve therapeutic and/or prophylactic benefit in at least one of a PDE6-related, QR2-related or CLB2-related condition. The actual amount effective for a particular application will depend on the condition or conditions being treated, the condition of the subject, the formulation, and the route of administration, as well as other factors known to those of skill in the art. Determination of an effective amount of a PDE6, QR2 or CLB2 modulator is well within the capabilities of those skilled in the art, in light of the disclosure herein, and will be determined using routine optimization techniques.

In therapeutic use, the compounds of the invention are administered to a subject at dosage levels of from about 0.05 mg/kg to about 10.0 mg/kg of body weight per day. For a human subject of approximately 70 kg, a dosage of from about 40 mg to about 600 mg per day may be used as a non-limiting example. Preferred doses include about 1 mg/kg, about 2.5 mg/kg, about 5 mg/kg, and about 7.5 mg/kg. Lower or higher doses than those disclosed herein may be used, as required. Such dosages, however, may be altered depending on a number of variables, not limited to the activity of the compound used, the condition to be treated, the mode of administration, the requirements of the individual subject, the severity of the condition being treated, and the judgment of the practitioner. The foregoing ranges are merely suggestive, as the number of variables in regard to an individual treatment regime is large, and considerable excursions from these recommended values are not uncommon.

The effective amount for use in humans can be determined from animal models. For example, a dose for humans can be formulated to achieve circulating, liver, topical and/or gastrointestinal concentrations that have been found to be effective in animals.

The effective amount when referring to an inhibitor of the invention will generally mean the dose ranges, modes of administration, formulations, etc., that have been recommended or approved by any of the various regulatory or advisory organizations in the medical or pharmaceutical arts (eg, FDA, AMA) or by the manufacturer or supplier.

In some embodiments, administration of compounds of the present invention may be intermittent, for example administration once every two days, every three days, every five days, once a week, once or twice a month, and the like. In some embodiments, the amount, forms, and/or amounts of the different forms may be varied at different times of administration.

Assays, Screening and Identification

The present invention is based upon the identification and validation of additional cellular targets of atorvastatin action. The additional cellular targets are PDE6D, QR2 and CLB2. Based on the validation of these targets, the invention provides assays for the identification of additional compounds that bind atorvastatin targets, preferably selectively over binding to other cellular factors. The invention provides compositions and methods directed to assays for additional molecules that bind to atorvastatin target molecules as well as the use of the identified molecules to treat diseases and unwanted conditions.

In another embodiment, the invention provides compositions and methods directed to assays for additional molecules that bind the atorvastatin target molecules to identify the molecules as potentially causing unwanted effects and conditions upon administration to a subject. The methods may be applied to identify possible negative effects of a drug compound or active agent. Non-limiting examples of atorvastatin action mediated by the targets include, but are not limited to, unwanted effects that affect a subject as a whole as well as particular systems within a subject, including the digestive, respiratory, nervous, muscluloskeletal, skin and appendages, urogenital, cardiovascular, as well as hemic and lymphatic systems. The effects can also affect the senses and result in metabolic and nutritional disorders. Non-limiting examples of such unwanted effects or conditions include, but are not limited to, chest pain, face edema, fever, neck rigidity, malaise, photosensitivity reactions, generalized edema, nausea, gastroenteritis, abnormal liver function as identified by abnormal liver tests, colitis, vomiting, gastritis, dry mouth, rectal hemorrhage, esophagitis, eructation, glossitis, mouth ulceration, anorexia, increased appetite, stomatitis, biliary pain, cheilitis, duodenal ulcer, dysphagia, enteritis, melena, gum hemorrhage, stomach ulcer, tenemus, ulcerative stomatis, hepatitis, pancreatitis, cholestatic jaundice, bronchitis, rhinitis, pneumonia, dyspnea, asthma, epistaxis, insomnia, dizziness, paresthesia, somnolence, amnesia, abnormal dreams, libido decreased, emotional liability, incoordination, peripheral neuropathy, torticollis, facial paralysis, hyperkinesias, depression, hypesthesia, hypertonia, arthritis, leg cramps, bursitis, tenosynovitis, myasthenia, tendinous contracture, myositis, pruritis, contact dermatitis, alopecia (hair loss), dry skin, sweating, acne, urticaria, eczema, seborrhea, skin ulcer, urinary tract infection, urinary frequency, cystitis, hematuria, impotence, dysuria, kidney calculus, norturia, epididymitis, fibrocystic breast, vaginal hemorrhage, albuminuria, breast enlargement, metrorrhagia, nephritis, urinary incontinence, urinary retention, urinary urgency, abnormal ejaculation, uterine hemorrhage, palpitation, vasodilatation, syncope, migraine, postural hypotension, phlebitis, arrhythmia, angina pectoris, hypertension, ecchymosis, anemia, lymphadenopathy, thrombocytopenia, petechia, amblyopia, tinnitus, dry eyes, refraction disorder, eye hemorrhage, deafness, glaucoma, parosmia, taste loss, taste perversion, peripheral edema, hyperglycemia, creatine phosphokinase increase, gout, weight gain, and hypoglycemia.

A. Analogs, Homologs and Polypeptides

As used herein, the terms "PDE6D", "QR2" and "CLB2" includes analogs of PDE6D, QR2 and CLB2, respectively, which may be obtainable from other animals or humans with deviations in amino acid sequences or encoding nucleotide sequences relative to known PDE6D, QR2 and CLB2 sequences. The term "analog" refers to a molecule which is structurally similar or has the same function or activity as PDE6D, QR2 and CLB2. As a non-limiting example, an analog of the PDE6D protein can be specifically bound by an antibody or T cell that specifically binds to PDE6D. Naturally occurring analogs from other animals and other humans, as well as alleles thereof (including those resulting from genetic polymorphisms), may be used in the practice of the invention. Synthetic analogs resulting from genetic engineering, such as those based upon the use of conservative amino acid substitutions or degeneracy in the genetic code may also be used.

The term "homolog" refers to a molecule which exhibits homology to another molecule, by for example, having sequences of chemical residues that are the same or similar at corresponding positions. Homologs of PDE6D, QR2 or CLB2 proteins may be used in the practice of the invention, especially in certain methods as disclosed herein.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

As used herein, PDE6D, QR2 and CLB2 genes and proteins include the known human PDE6D, QR2 and CLB2 genes and proteins, as well as structurally and/or functionally similar analogs thereof. PDE6D, QR2 and CLB2 analogs generally share at least about 50%, 60%, 70%, 80%, 90% or more amino acid homology (using BLAST criteria). PDE6D, QR2 and CLB2 nucleotide analogs preferably share 50%, 60%, 70%, 80%, 90% or more nucleic acid homology (using BLAST criteria).

The PDE6D, QR2 and CLB2 proteins of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different PDE6D, QR2 or CLB2 proteins or fragments thereof, as well as fusion proteins of a PDE6D, QR2 or CLB2 protein and a heterologous polypeptide are also included and may be used in the practice of the invention.

In general, naturally occurring allelic variants of human PDE6D, QR2 or CLB2 share a high degree of structural identity and homology (e.g., 90% or more homology). Typically, allelic variants of a PDE6D, QR2 or CLB2 protein contain conservative amino acid substitutions. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. pages 13-15 "Biochemistry" $2^{nd}$ ED. Lubert Stryer ed (Stanford University); Henikoff et al., PNAS 1992 Vol 89 10915-10919; Lei et al., *J Biol Chem* 1995 May 19; 270(20):11882-6).

PDE6D, QR2 and CLB2 analogs can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA,* 317:415 (1986)) or other known techniques can be performed on the cloned DNA to produce the variant DNA.

As defined herein, a PDE6D, QR2 or CLB2 analog has the distinguishing attribute of having at least one epitope that is "cross reactive" with a PDE6D, QR2 or CLB2 protein, respectively, as known in the field. The term "cross reactive" means that an antibody or T cell that specifically binds to a PDE6D, QR2 or CLB2 analog also specifically binds to known PDE6D, QR2 or CLB2 proteins. A polypeptide ceases to be analog when it no longer contains any epitope capable of being recognized by an antibody or T cell that specifically binds to a PDE6D, QR2 or CLB2 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., *J. Immunol* 2000 165(12): 6949-6955; Hebbes et al., *Mol Immunol* (1989) 26(9): 865-73; Schwartz et al., *J Immunol* (1985) 135(4): 2598-608.

PDE6D, QR2 or CLB2 polypeptides may be generated using standard peptide synthesis technology or using chemical cleavage methods well known in the art. Alternatively, recombinant methods can be used to generate nucleic acid molecules that encode a PDE6D, QR2 or CLB2 polypeptide. In one embodiment, nucleic acid molecules provide a means to generate defined fragments of a PDE6D, QR2 or CLB2 protein or analog thereof. The polypeptides may contain covalent modifications and still be used in the practice of the invention. Non-limiting examples of such modifications include reacting the amino acid residues of a PDE6D, QR2 or CLB2 polypeptide with an organic derivatizing agent that is capable of reacting with selected side chains or the N- or C-terminal residues of PDE6D, QR2 or CLB2; altering the native glycosylation pattern of a protein of the invention; and linking the PDE6D, QR2 or CLB2 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PDE6D, QR2 and CLB2 proteins of the present invention can also be modified to form a chimeric molecule comprising PDE6D, QR2 or CLB2 fused to another polypeptide or amino acid sequence. Such a chimeric molecule can be synthesized chemically or recombinantly and used in the practice of the invention. A chimeric molecule can comprise a fusion of a PDE6D, QR2 or CLB2 protein with a polyhistidine epitope tag, which provides an epitope to which immobilized nickel can selectively bind, with cytokines or with growth factors. In an alternative embodiment, the chimeric molecule can comprise a fusion of a PDE6D, QR2 or CLB2 protein with an immunoglobulin or a particular region of an immunoglobulin. For the production of immunoglobulin fusions see, e.g., U.S. Pat. No. 5,428,130. Alternatively, the fusion can be with a signaling moiety, such as a fluorescent protein or chromophore, including, but not limited to green fluorescent protein.

PDE6D, QR2 or CLB2 polypeptides may also be expressed as a fusion with a phage coat protein for expression on the surface of phage particles. This approach is described in copending U.S. patent applications Ser. No. 10/115,442, filed 2 Apr. 2002, and application Ser. No. 10/406,797 filed on 2 Apr. 2003 (or PCT International Application PCT/US03/10247 filed 2 Apr. 2003), both of which are incorporated by reference as if fully set forth. The expressed proteins may be used with a compound that binds PDE6D, QR2 and/or CLB2, such as atorvastatin, in an immobilized form as described in these applications for use in screens for other compounds that bind PDE6D, QR2 and/or CLB2.

B. Uses and Methods

In another aspect of the invention, methods for the identification of additional compounds that bind PDE6D, QR2 and/or CLB2 are provided. The methods may thus be viewed as screening assays that rely upon the identity of the PDE6D, QR2 and/or CLB2 target and the ability to detect the result(s) of a binding event to the target. The detection of a binding event may be made directly or indirectly, and identifies a compound as capable of binding the target. The compound may be any chemical agent, including small molecules with a molecular weight less than about 5000 Daltons, preferably less than about 1000 Daltons. Preferred compounds of the invention bind the targets with a $K_d$ less than a range from about 1 µM to 10 nM and/or are selective for said target. Preferably, the assays are conducted under quantitative conditions such that the affinity, or relative affinity, of binding of a compound to a target may be determined.

In one embodiment of the invention, the assays are based upon the expression of a target on the surface of phage particles that is contacted with a test compound followed by detection of binding between the target and the compound. In a preferred form, the contacting may be made in the presence of another compound that binds the target, such as atorvastatin, and thus may be based upon the ability of a test compound to compete with atorvastatin for binding to the target. In a preferred embodiment, additional compounds that bind PDE6D, QR2 or CLB2 are identified by the use of screening methods as disclosed in copending U.S. patent applications Ser. No. 10/115,442, filed 2 Apr. 2002, and Ser. No. 10/406,797 filed on 2 Apr. 2003 (or PCT International Application PCT/US03/10247 filed 2 Apr. 2003), both of which are incorporated by reference as if fully set forth.

Thus the use of PDE6D, QR2 and/or CLB2 polypeptides to screen a potential drug compound or other active agent and identify it as likely to cause an unwanted effect in a subject provided with said compound or agent is provided by the invention. The identified compounds may thus be eliminated from consideration for use in subjects, such as human beings.

A test compound of the invention maybe a member of a class of compounds such that all members of the class may be tested for binding to the targets. The assaying of a class of compounds permits the identification of the selective binding of one or some members of the class, as opposed to other members of the class, as binding the targets. This may be used to identify the binding members of the class as more selective for the targets, or alternatively, the non-binding members of the class as preferentially non-selective for the targets. As a non-limiting example, statin compounds in addition to atorvastatin may be used in the practice of the invention to identify whether they bind the targets to determine whether they are capable of mediating the same action as atorvastatin binding or whether they do not bind and are thus only specific for targeting HMG-CoA reductase In another embodiment, the invention provides methods of identifying or screening for additional compounds that increase (stimulate) or decrease (inhibit) the function and/or activity of PDE6D, QR2 and/or CLB2 (target) polypeptides or fragments, portions, or analogs thereof. The methods may be performed in vitro or in vivo. One method for identifying a compound as binding and inhibiting the activity of a target comprises providing an indicator composition comprising a target polypeptide or fragment, portion, or analog thereof, contacting the indicator composition with a test compound (a potential PDE6D, QR2 or CLB2 activator or inhibitor), and determining the effect of the test compound on PDE6D, QR or CLB2 activity in the indicator composition to identify a compound that stimulates or inhibits the activity or function of the target. The methods are preferably used to identify stimulators and inhibitors that generate unwanted effects and conditions as disclosed herein and/or for use in the treatment and/or prevention of diseases and unwanted conditions as disclosed herein.

In another aspect, a compound or agent that affects the expression, function and/or activity of PDE6D, QR2 and/or CLB2 may be identified as resulting in unwanted effects upon use in a subject. Such a compound or agent may act by increasing or decreasing the expression of, or the function and/or activity of PDE6D, QR2 and/or CLB2.

In another aspect of the invention, a compound that results in an undesirable condition mediated by aberrant PDE6D, QR2 and/or CLB2 activity can be identified and thus not used. Non-limiting examples of PDE6D, QR2 activity affected by atorvastatin and other compounds include the binding of PDE6D to the catalytic PDE alpha and/or beta subunits; and the binding of PDE6D to prenylated proteins. The invention thus provides methods for identifying, and thus avoiding, compounds that modulate the cellular signaling cascades mediated by PDE6D. In one embodiment, compounds that modulate the levels and/or activities of membrane-bound PDE6D or of prenylated proteins may be identified and thus avoided.

The target polypeptides, as well as fragments, homologs, and analogs thereof, of the invention have a number of different specific uses. In particular, they may be used to identify additional compounds that bind PDE6D, QR2 or CLB2, including compounds that stimulate or inhibit PDE6D, QR2 or CLB2 function or activity. In one preferred embodiment, PDE6D, QR2 or CLB2 is expressed as a fusion protein for expression on phage particles which may then be screened against a library of compounds, either in solution or in immobilized form.

The invention also provides for the use of polynucleotides/nucleic acid molecules, proteins, protein analogs, and PDE6D, QR2 or CLB2 binding compounds described herein in one or more of the following methods: a) expression of PDE6D, QR2 or CLB2 polypeptides; b) screening assays; c) methods of determining effects of a compound on PDE6D, QR2 or CLB2; and d) methods of treatment (e.g., therapeutic and prophylactic). The polynucleotides of the invention can be used, for example, to express PDE6D, QR2 or CLB2 protein (e.g., via a recombinant expression vector in a host cell), to detect PDE6D, QR2 or CLB2 mRNA (e.g., in a biological sample) or a genetic alteration in a PDE6D, QR2 or CLB2 gene, and to inhibit expression of PDE6D, QR2 or CLB2 activity, as described further below. The PDE6D, QR2 or CLB2 proteins can be used to treat diseases or unwanted conditions characterized by undesirable levels of PDE6D, QR2 or CLB2 production or of PDE6D, QR2 or CLB2 activity.

The invention includes methods to screen for drugs or compounds which bind and/or modulate PDE6D, QR2 or CLB2 activity, which drugs or compounds may be used to treat disorders requiring an increase or decrease in PDE6D, QR2 or CLB2 function or activity or to screen a drug or compound for the effect of modulating PDE6D, QR2 or CLB2 activity, which drug or compound may then be avoided because they cause an unwanted condition in a subject treated with said drug or compound. The methods include a method for identifying and/or screening compounds, i.e., candidate or test compounds or agents (such as, but not limited to, peptides: peptidomimetics; small molecules of less than 5000, less than 4500, less than 4000, less than 3500, less than 3000, less than 2500, less than 2000, less than 1500, less than 1000, or less than 500 Daltons; or other drugs) which bind to PDE6D, QR2 or CLB2 proteins and optionally have a stimulatory or inhibitory effect thereon, or have a stimulatory or inhibitory effect on the expression of PDE6D, QR2 or CLB2, and/or result in an unwanted effect. Preferred is the identification and/or screening of compounds that bind with a $K_d$ of less than about 500 μM, less than about 100 μM, less than about 50 μM, less than about 10 μM, less than about 5 μM, less than about 1 μM, less than about 0.5 μM, or less than about 0.1 μM.

In another embodiment, the assays may detect an increase or decrease in the binding of a PDE6D, QR2 or CLB2 polypeptide or biologically active portion thereof with its cognate ligand. The invention thus provides a method for identifying a compound as binding a PDE6D, QR2 or CLB2 polypeptide by contacting the polypeptide, or a phage particle expressing the polypeptide on its surface, with a test compound, and determining whether the polypeptide binds to the test compound. The binding of the test compound to the polypeptide may be detected by direct detection of interactions between the test compound and the polypeptide; detection of binding by indirect detection of interactions between the test compound and the polypeptide; detection of binding using a competition binding assay; and detection of binding using an assay for the polypeptide's activity.

In another embodiment, a method for identifying a compound which stimulates or inhibits the activity of a PDE6D, QR2 or CLB2 polypeptide is provided by contacting a PDE6D, QR2 or CLB2 polypeptide with a test compound and determining the extent to which the test compound stimulates or inhibits the activity of the polypeptide. The methods may be performed in vitro or in vivo, such as in cells from an animal (including cell lines) or cells in an animal.

Other non-limiting examples of binding assays include biacore-type binding assays, DiscoveRx type binding assays; fluorescence and fluorescence polarization; FRET (fluorescence energy transfer); fluorescence enhancement/ quenching; effects on protein stability (binding stabilizes the protein, affecting unfolding thermodynamics as measured by a melting temperature, or the concentration of denaturants required to unfold the protein); general migration, rotation properties of the protein or small molecule; interference with chemical modification (e.g. if there is a reactive group at an active site which can be chemically labeled, this may be blocked if a small molecule binds at the active site); NMR-based measurements; crystallographic methods; other indirect cell-based methods (or methods based on artificial cells, micelles etc.); and 3-hybrid type methods.

In one embodiment of the invention, a cell-free assay is provided in which a PDE6D, QR2 or CLB2 protein or biologically active portion thereof is contacted with a test compound and the ability of the test compound to bind to the protein or biologically active portion thereof is determined. Preferably, the compound is a small molecule as described herein. In a preferred embodiment, the assay includes contacting the PDE6D, QR2 or CLB2 protein or biologically active portion thereof with a known compound which binds PDE6D, QR2 or CLB2 to form an assay mixture, contacting the assay mixture with a test compound, and determining the ability of the test compound to interact with a PDE6D, QR2 or CLB2 protein, wherein determining the ability of the test compound to interact with a PDE6D, QR2 or CLB2 protein comprises determining the ability of the test compound to preferentially bind to PDE6D, QR2 or CLB2 or biologically active portion thereof as compared to the known compound.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). The methods may also be used to confirm the binding of a compound to PDE6D, QR2 or CLB2 or to confirm the effect of a compound on PDE6D, QR2 or CLB2 function or activity.

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994)*Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds maybe presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

One can screen peptide libraries to identify molecules that interact with PDE6D, QR2 or CLB2 protein sequences. Alternatively, the particles are screened against small molecules of interest as described herein. Conversely, PDE6D, QR2 or CLB2 polypeptides may be expressed on bacteriophage particles and then screened against peptides or small molecules in solution or immobilized form. Accordingly, peptides and small molecules that bind and inhibit PDE6D, QR2 or CLB2 are identified without any prior information on the structure of the peptides and small molecules.

In another embodiment, an assay is a cell-based assay comprising contacting a cell expressing a PDE6D, QR2 or CLB2 binding ligand molecule with a test compound and determining the ability of the test compound to affect the binding of PDE6D, QR2 or CLB2 to the ligand. Determining the ability of the test compound to increase or decrease the binding of a PDE6D, QR2 or CLB2 ligand can be accomplished, for example, by determining the ability of the PDE6D, QR2 or CLB2 protein to interact with the ligand, such as by determination of direct binding between PDE6D, QR2 or CLB2 and a ligand thereof, such as by coupling the PDE6D, QR2 or CLB2 protein with a radioisotope, fluorescent, or enzymatic label such that binding of the protein to a ligand molecule can be determined by detecting the labeled protein in a complex.

Alternatively, cell lines that express PDE6D, QR2 or CLB2 are used to identify protein-protein interactions mediated by PDE6D, QR2 or CLB2 using immunoprecipitation techniques (see, e.g., Hamilton B J, et al. *Biochem. Biophys. Res. Commun.* 1999, 261:64651). The PDE6D, QR2 or CLB2 proteins can also be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins or factors, which bind to or interact with PDE6D, QR2 or CLB2. The identified proteins or factors may be used as a ligand molecule, which binds PDE6D, QR2 or CLB2 as described herein. The invention also provides for determining the ability of a compound to affect the binding of PDE6D, QR2 or CLB2 and a ligand molecule, without the labeling either of the binding members. For example, a microphysiometer can be used to detect the interaction of with its ligand without the labeling of either PDE6D, QR2 or CLB2 or the ligand. McConnell, H. M. et al. (1992) *Science* 257:1906-1912.

In another embodiment, determining the ability of a PDE6D, QR2 or CLB2 protein to bind to or interact with a ligand molecule can be accomplished by detecting the activity of the ligand. As a non-limiting example, the activity of PDE6 bound or not bound to a PDE6D polypeptide can be the detectable signal for PDE6D binding.

In more than one embodiment of the above assay methods of the present invention, it may be desirable to immobilize either PDE6D, QR2 or CLB2 or its ligand molecule to facilitate separation of complexed from uncomplexed forms of one or both of the proteins, as well as to accommodate automation of the assay. Binding of a test compound to a PDE6D, QR2 or CLB2 protein, or interaction of a PDE6D, QR2 or CLB2 protein with a ligand molecule in the presence and absence of a candidate compound, can be accomplished in any vessel suitable for containing the binding members and other reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/kinase fusion proteins or glutathione-S-transferase/target fusion proteins can be adsorbed adsorption onto glutathione sepharose beads (Sigma Chemical, St. Louis, Mo.) or glutathione derivatized microtitre plates, which are then combined with the test compound and either the non-adsorbed ligand or PDE6D, QR2 or CLB2 protein, respectively, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PDE6D, QR2 or CLB2 binding or activity determined using standard techniques.

Other techniques for immobilizing proteins on matrices can also be used in the screening assays of the invention. For example, either a PDE6D, QR2 or CLB2 protein or a ligand molecule thereof can be immobilized utilizing conjugation of biotin and streptavidin. Biotinylated PDE6D, QR2 or CLB2 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PDE6D, QR2 or CLB2 protein or ligand molecules but which do not interfere with binding of the PDE6D, QR2 or CLB2 protein to its ligand can be derivatized to the wells of the plate, and unbound target or PDE6D, QR2 or CLB2 protein trapped in the wells by antibody conjugation. Methods for detecting such complexes, in addition to those described above for the GST-immobilized complexes, include immunodetection of complexes using antibodies reactive with the PDE6D, QR2 or CLB2 protein or ligand, as well as enzyme-linked assays which rely on detecting an enzymatic activity associated with the PDE6D, QR2 or CLB2 protein or ligand.

In another embodiment, effectors of PDE6D, QR2 or CLB2 expression are identified in a method wherein a cell is contacted with a candidate compound and the expression of PDE6D, QR2 or CLB2 mRNA or protein in the cell is. determined. The level of expression of PDE6D, QR2 or CLB2 mRNA or protein in the presence of the candidate compound is compared to the level of expression of PDE6D, QR2 or CLB2 mRNA or protein in the absence of the candidate compound. The candidate compound can then be identified as a stimulator or inhibitor of PDE6D, QR2 or CLB2 expression based on this comparison. For example, when expression of PDE6D, QR2 or CLB2 mRNA or protein is less (for example, statistically significantly less) in the presence of the candidate compound than in its absence, the candidate compound is identified as an inhibitor of PDE6D, QR2 or CLB2 mRNA or protein expression. Conversely, when expression of PDE6D, QR2 or CLB2 mRNA or protein is more (for example, statistically significantly more) in the presence of the candidate compound than in its absence, the candidate compound is identified as a stimulator of PDE6D, QR2 or CLB2 mRNA or protein expression. The level of PDE6D, QR2 or CLB2 mRNA or protein expression in the cells can be determined by appropriate methods known in the field.

This invention further pertains to novel compounds and agents identified by the above-described screening assays. Accordingly, it is within the scope of this invention to further use an agent identified as described herein in an appropriate animal model. For example, a PDE6D, QR2 or CLB2 binding compound identified as described herein can be used in an animal model to determine the efficacy, toxicity, or side effects of treatment with such a compound. Alternatively, an agent identified as described herein can be used in an animal model to provide additional information concerning the mechanism of action of such an agent. Furthermore, this invention pertains to uses of novel agents identified by the above-described screening assays for treatments as described herein.

With respect to screening assays, the invention provides for monitoring the influence of agents (e.g., drugs or compounds) on the level of expression or activity of a PDE6D, QR2 or CLB2 protein, such as in clinical trials or in post-trial use. For example, the level of effectiveness of an agent determined by a screening assay to decrease PDE6D, QR2 or CLB2 gene expression, protein levels, or downregulate PDE6D, QR2 or CLB2 activity, can be monitored in clinical trials of subjects exhibiting undesirable PDE6D, QR2 or CLB2 gene expression, protein levels, or upregulated activity. In such pre-clinical or clinical trials or post-trial uses, the expression or activity of a PDE6D, QR2 or CLB2 gene, and preferably, other genes that have been implicated in a disorder, can be used as a "read out" or markers of the phenotype of a particular cell. The levels of gene expression (i.e., a gene expression pattern) can be quantified by Northern blot analysis; the use of DNA chips or microarrays or bead mediated arrays (like those of Illumina, Inc.); RT-PCR; or other techniques known in the art. Alternatively, expression can be determined by measuring the amount of protein produced, by one of the methods as described herein, or by measuring the levels of activity of PDE6D, QR2 or CLB2. In this way, the gene expression pattern can serve as a marker, indicative of the physiological response of the cells to the agent. Accordingly, this response state may be determined before, and at various points during treatment of the individual with the agent or after administration of the agent to the individual.

In a preferred embodiment, the present invention provides a method for monitoring the effectiveness of treatment of a subject by administration of a compound that binds PDE6D, QR2 or CLB2 comprising the steps of (i) obtaining a pre-administration sample from a subject prior to administration of the agent; (ii) detecting the level of expression of a PDE6D, QR2 or CLB2 protein, mRNA, or genomic DNA in the pre-administration sample; (iii) obtaining one or more post-administration samples from the subject; (iv) detecting the level of expression or activity of the PDE6D, QR2 or CLB2 protein, mRNA, or genomic DNA in the post-administration samples; (v) comparing the level of expression or activity of the PDE6D, QR2 or CLB2 protein, mRNA, or genomic DNA in the pre-administration sample with the PDE6D, QR2 or CLB2 protein, mRNA, or genomic DNA in the post administration sample or samples; and optionally (vi) altering the administration of the agent to the subject accordingly. For example, increased administration of an inhibitory compound may be desirable to increase the inhibition of PDE6D, QR2 or CLB2 to higher levels than detected, i.e., to increase the effectiveness of the compound. Alternatively, decreased administration of an inhibitory compound may be desirable to decrease inhibition of PDE6D, QR2 or CLB2 to lower levels than detected, i.e. to decrease the effectiveness of the agent. According to such an embodiment, PDE6D, QR2 or CLB2 expression or activity may be used as an indicator of the effectiveness of an agent, even in the absence of an observable phenotypic response.

Unless otherwise expressly stated, all terms of art, notations and other scientific terms or terminology used herein are intended to have the meanings commonly understood by those of skill in the art to which this invention pertains. The techniques and procedures described or referenced herein are commonly employed using conventional methodology by those skilled in the art, such as, for example, the widely utilized molecular cloning methodologies described in Sambrook et al., *Molecular Cloning: A Laboratory Manual* 2nd. edition (1989) Cold Spring Harbor Laboratory Press, Cold Spring Harbor, N.Y.

Kits/Articles of Manufacture

For use in the therapeutic applications described herein, kits and articles of manufacture are also within the scope of the invention. Such kits can comprise a carrier, package, or container that is compartmentalized to receive one or more containers such as vials, tubes, and the like, each of the container(s) comprising one of the separate elements to be used in a method of the invention. Suitable containers include, for example, bottles, vials, syringes, and test tubes. The containers can be formed from a variety of materials such as glass or plastic.

For example, the container(s) can comprise one or more pyrrole compounds of the invention, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a pyrrole compound with an identifying description or label or instructions relating to its use in the methods of the present invention.

A kit of the invention will typically may comprise one or more additional containers, each with one or more of various materials (such as reagents, optionally in concentrated form, and/or devices) desirable from a commercial and user standpoint for use of a pyrrole compound of the invention. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

The terms "kit" and "article of manufacture" may be used as synonyms.

The methods of the present invention may be carried out with other compounds such as thiazole-containing, furan-containing, imidazole-containing, oxazole-containing, and thiophene-containing compounds. Suitable examples of such compounds are described in co-pending patent applications—(i) U.S. Patent Application entitled "Heterocyclic compounds and uses thereof", Ser. No. 10/848,521, filed on May 17, 2004 and U.S. Patent Application entitled "Heterocyclic compounds and uses thereof", Ser. No. 10/847,897, filed on May 17, 2004. Also, other compounds useful in the methods described herein are described in co-pending U.S. Patent Application entitled "Compound and uses thereof", Ser. No. 10/848,515, filed on May 17, 2004.

Having now generally described the invention, the same will be more readily understood through reference to the following examples, which are provided by way of illustration, and are not intended to be limiting of the present invention, unless specified.

EXAMPLES

Example 1

Identification of Novel Molecules that Bind PDE6D with High Affinity

Forty-four molecules were screened for PDE6D binding activity in a standard phage-based competition binding assay, as described in co-pending U.S. patent applications Ser. No. 10/115,442, filed 2 Apr. 2002, and Ser. No. 10/406,797 filed on 2 Apr. 2003 (or PCT International Application PCT/US03/10247 filed 2 Apr. 2003). All compounds were screened in duplicate (duplicate sets of bars) at a concentration of 2 μM. The fraction of PDE6D-displaying phage bound to immobilized atorvastatin in the presence and absence of soluble competitor (test compound) is indicated on the y-axis. Competitors that significantly reduce the fraction bound to the immobilized atorvastatin are candidate lead molecules. Non-limiting examples of candidate lead compounds from this screen include molecules atorvastatin, 781430, 780104, 780520, 780676, and 780858.

Example 2

Synthesis of Pyrrole Compounds

The diketone precursor, 4-fluoro-α-(2-methyl-1-oxopropyl)-γ-oxo-N-phenyl-β-phenylbenzene-butaneamide, of the pyrrole compounds described herein was bought commercially and then condensed with ammonium acetate to synthesize 781430. The diketone precursor, also known as M-4 and Cu(OAc)2 (5 eq) was combined with ammonium acetate (5-10 eq) and refluxed at 100° C. for 24 hrs. Then ammonium hydroxide was added to chelate the copper and extracted with EtOAc. Final purification was by HPLC.

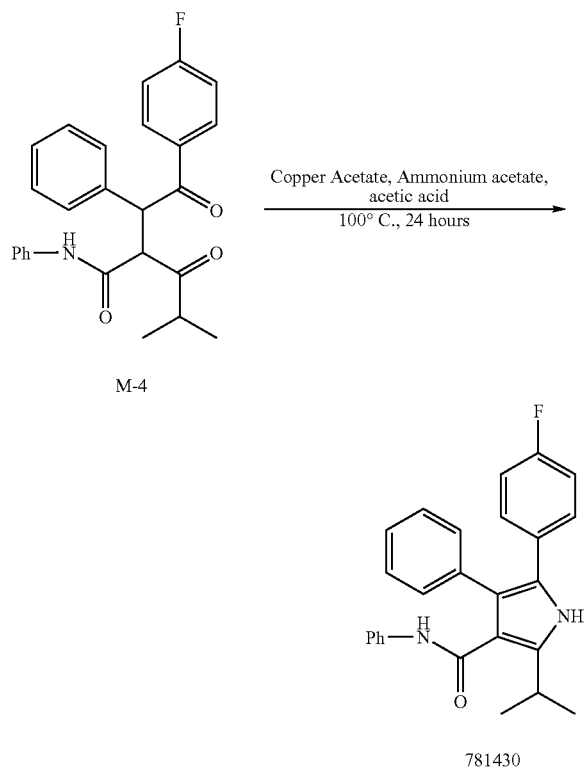

Figure 30:
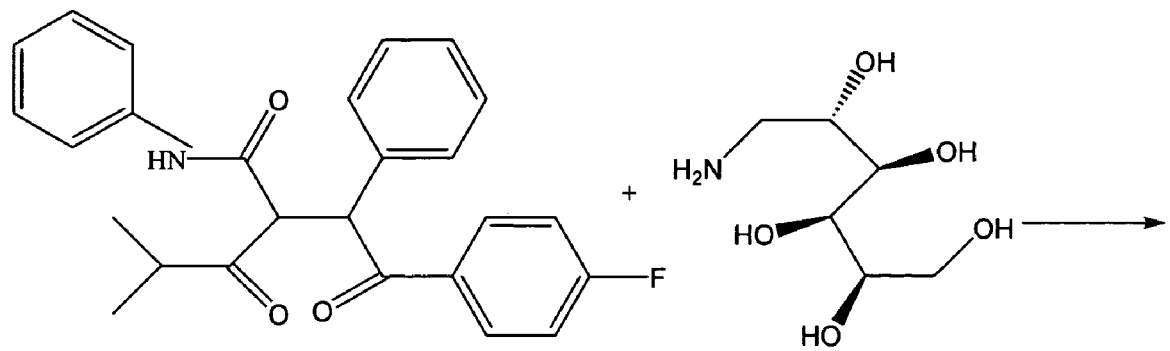
FIG. 30 shows Scheme 3 for the synthesis of pyrrole compound number 782236.
Figure 30:
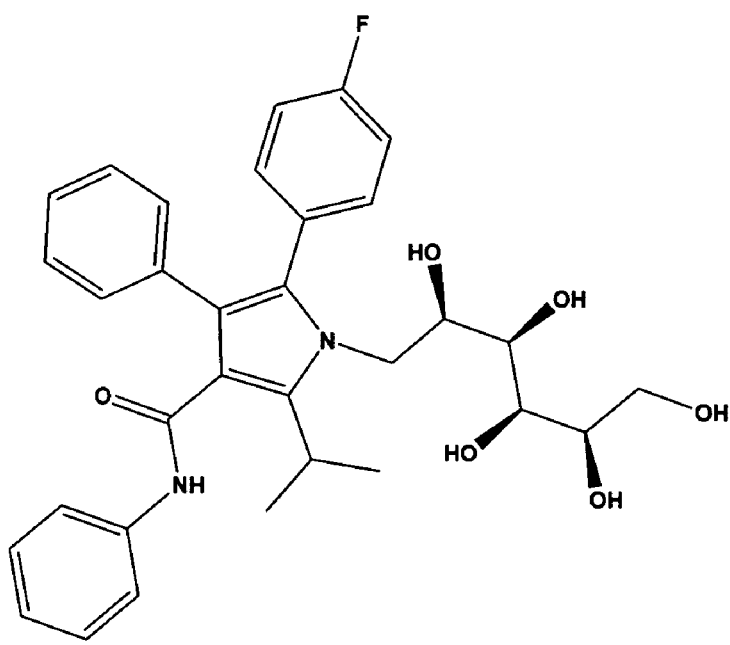
Figure 31:
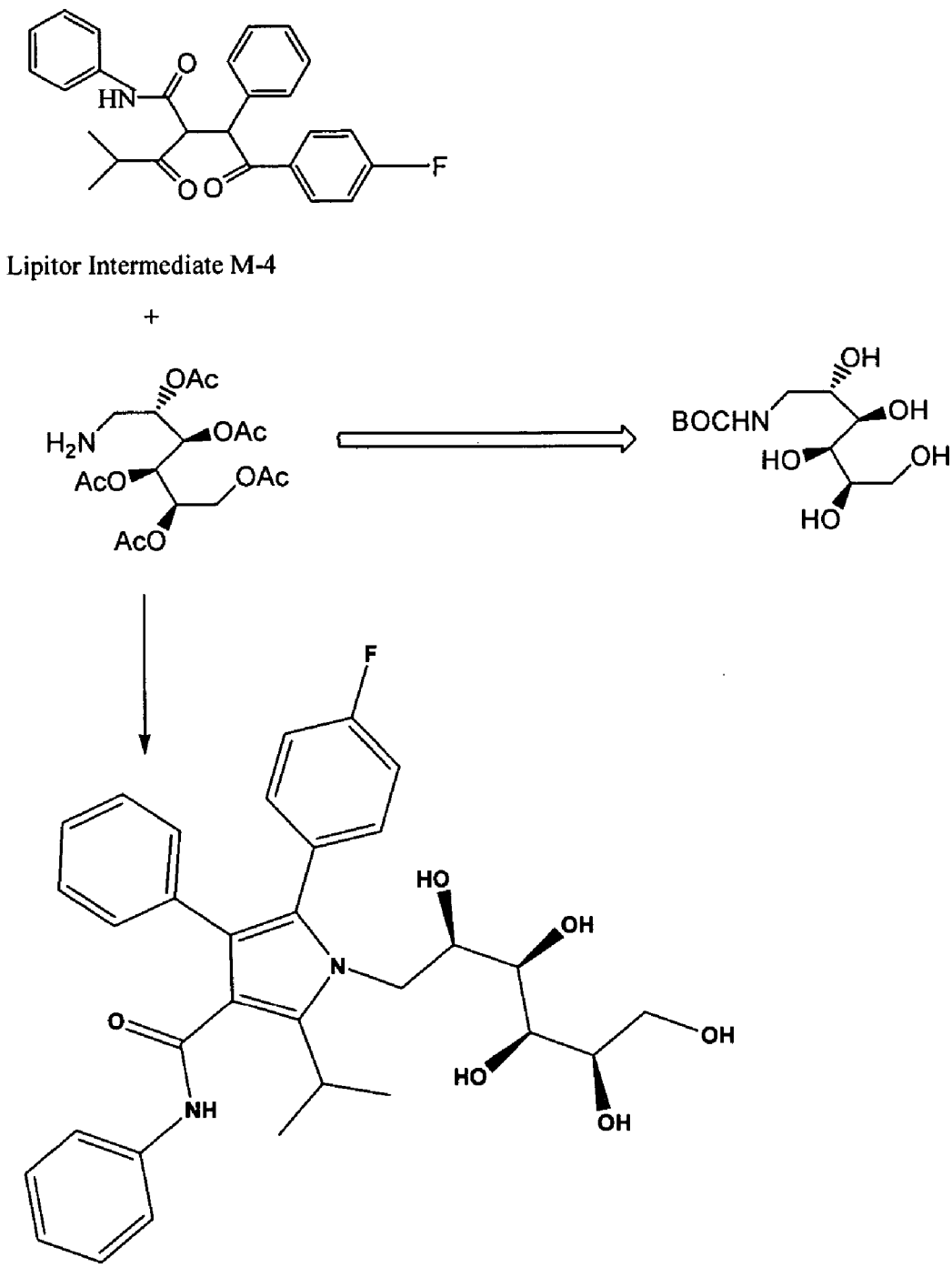
FIG. 31 shows Scheme 4 for the synthesis of pyrrole compound number 782236.
Figure 32:
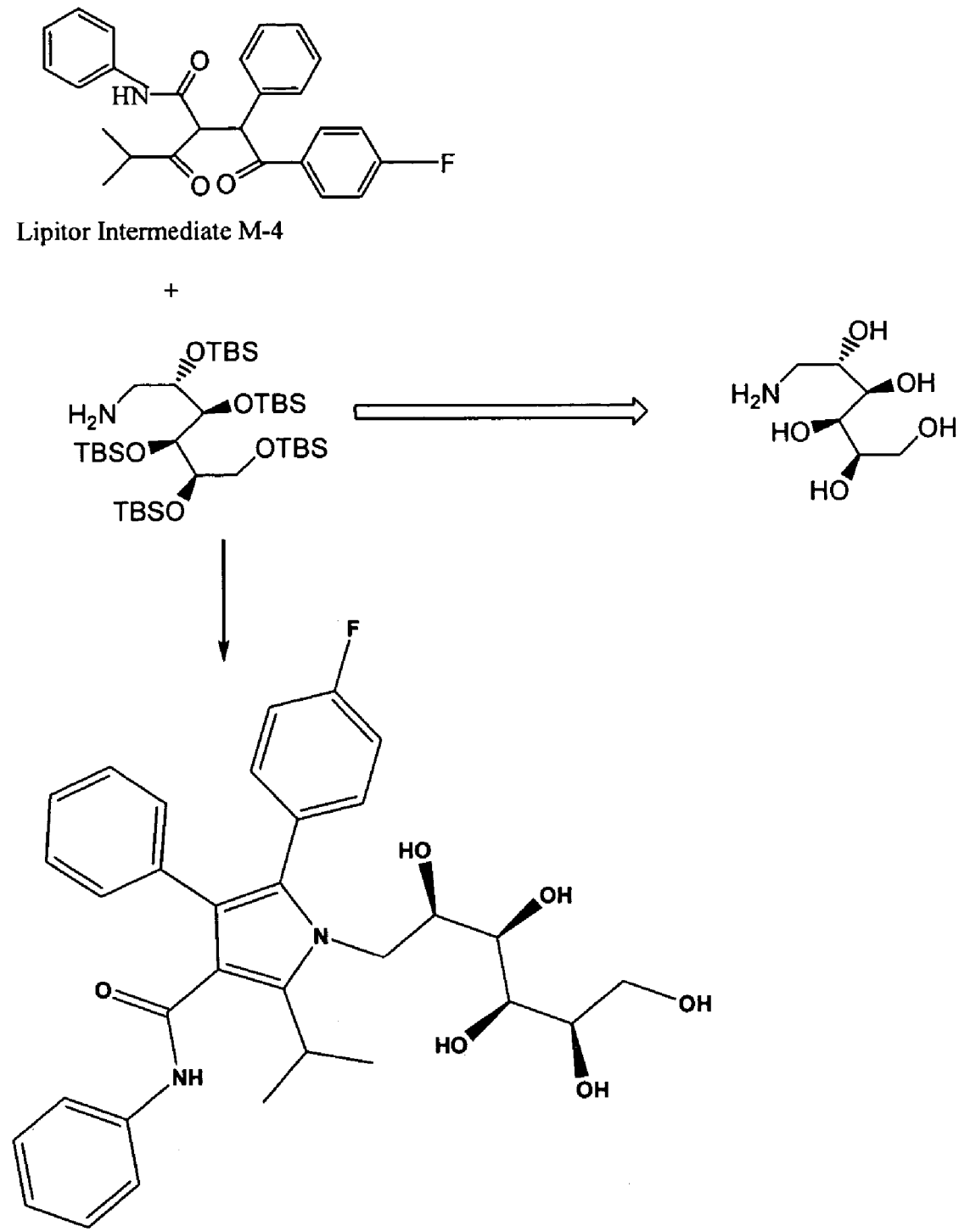
FIG. 32 shows Scheme 5 for the synthesis of pyrrole compound number 782236.
Figure 33A:
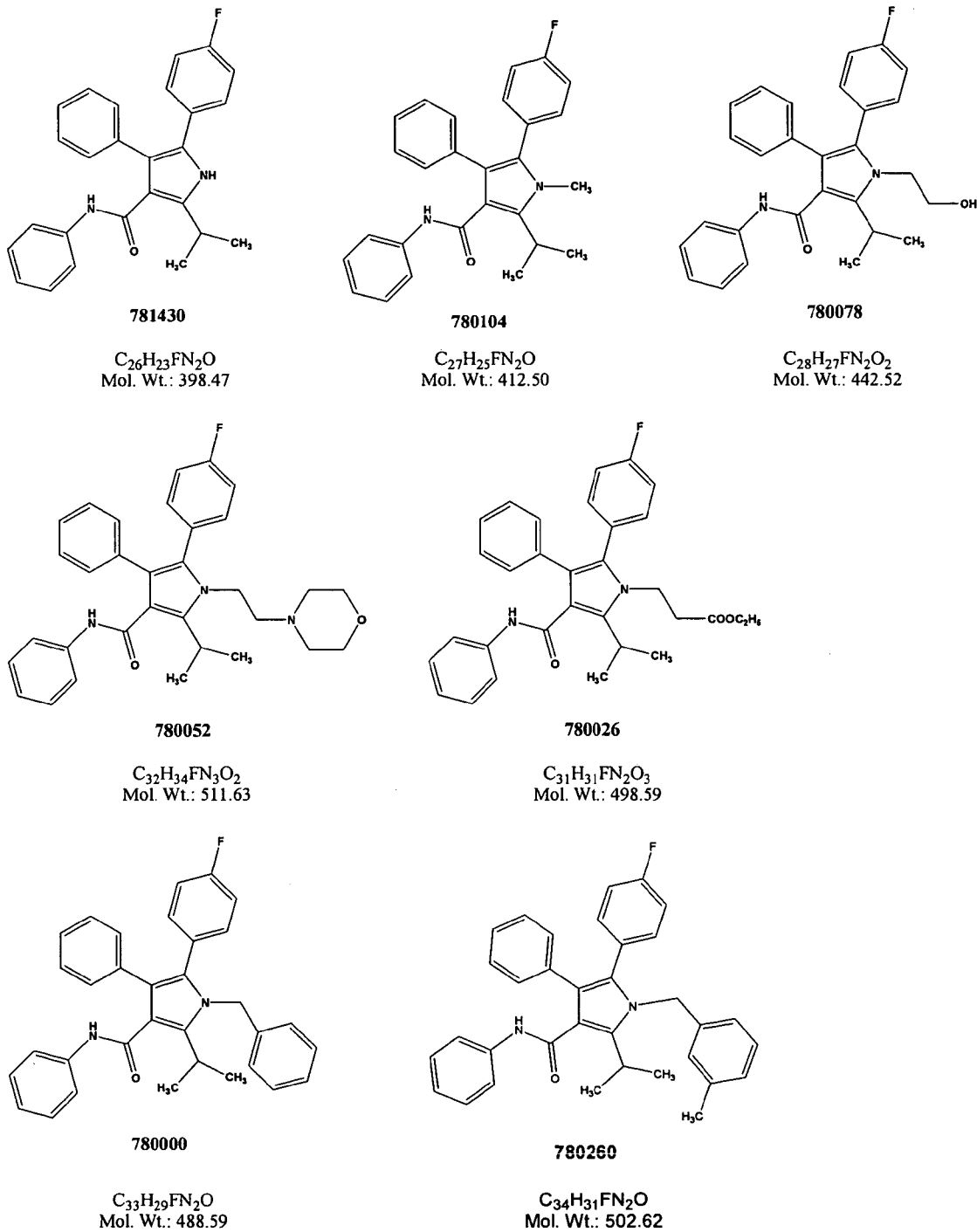
FIG. 33A through 33H shows the chemical structure of the pyrrole compounds of the invention.
Figure 33B:
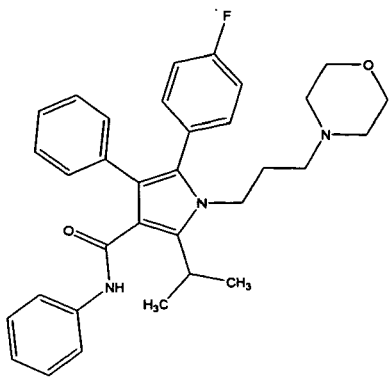
Figure 33B:
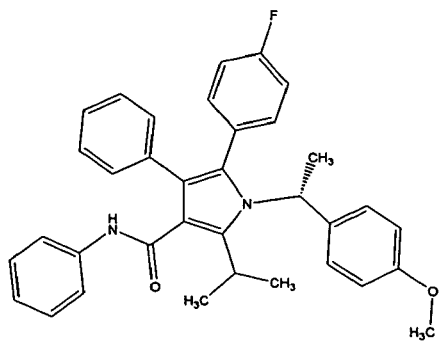
Figure 33B:
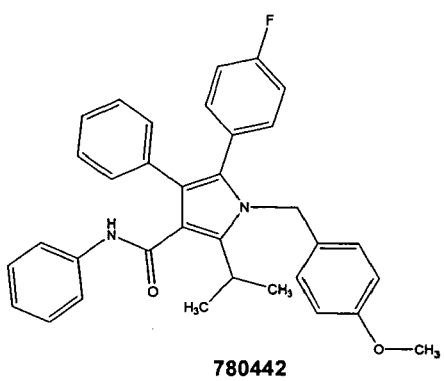
Figure 33B:
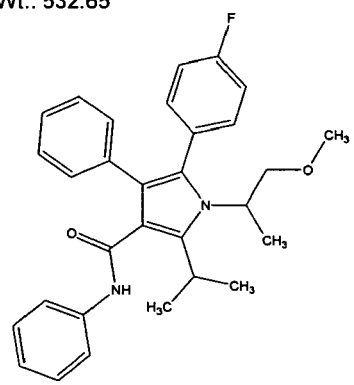
Figure 33B:
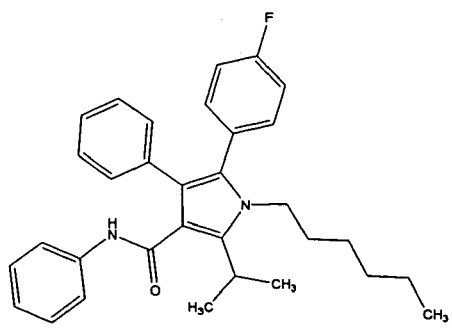
Figure 33B:
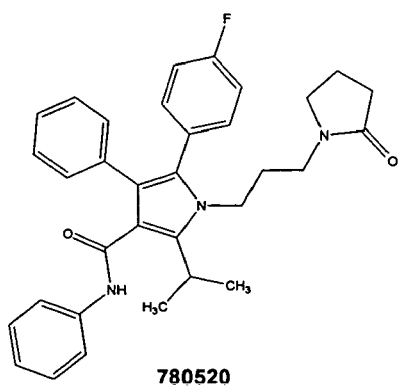
Figure 33C:
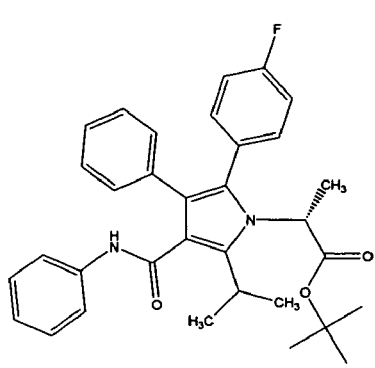
Figure 33C:
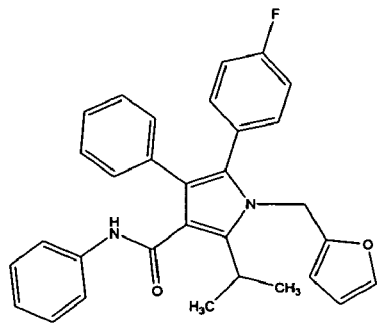
Figure 33C:
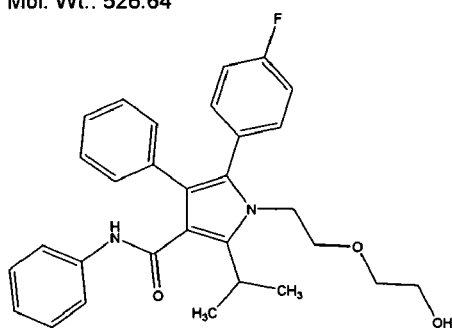
Figure 33C:
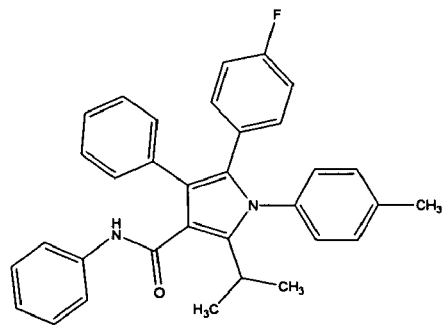
Figure 33C:
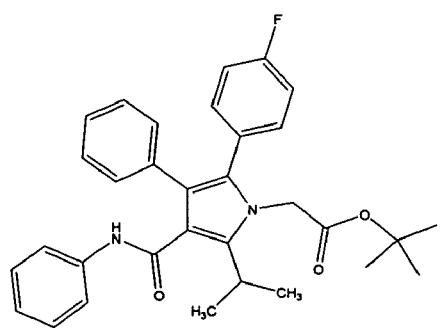
Figure 33C:
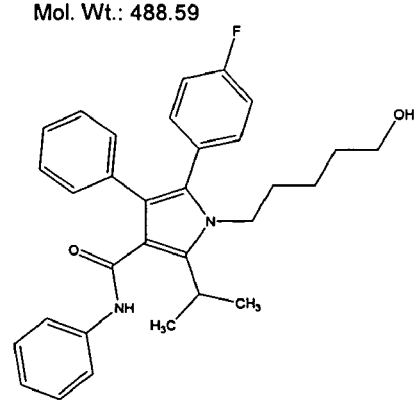
Figure 33D:
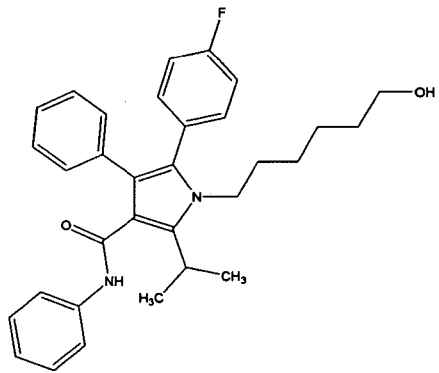
Figure 33D:
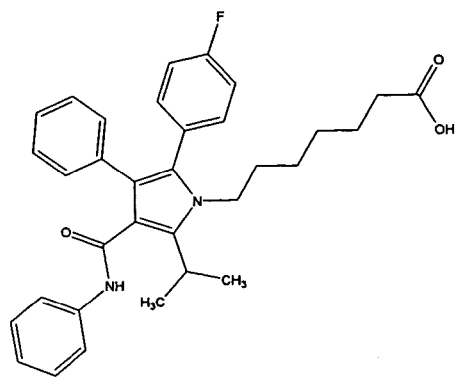
Figure 33D:
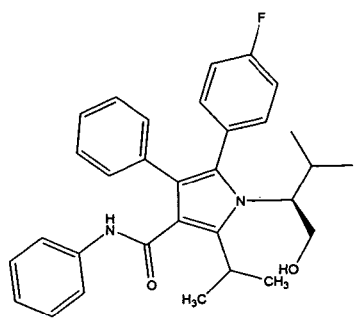
Figure 33D:
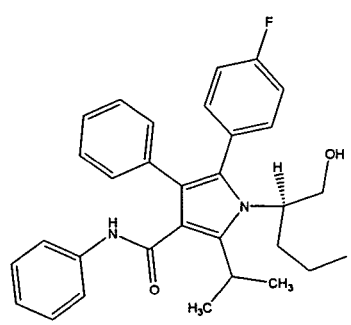
Figure 33D:
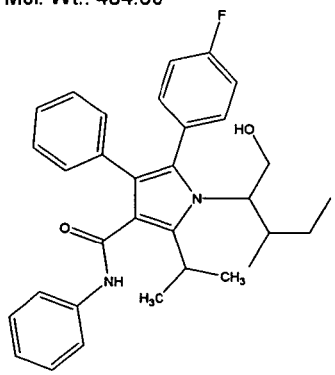
Figure 33D:
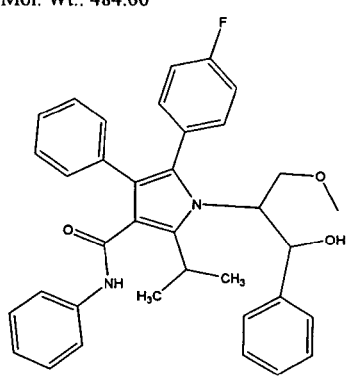
Figure 33E:
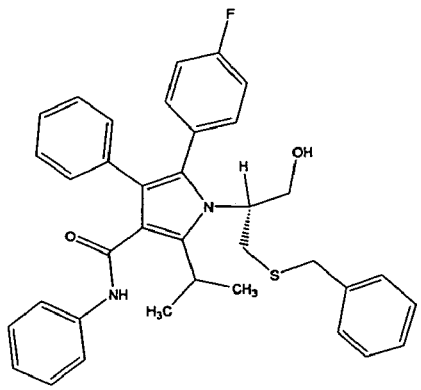
Figure 33E:
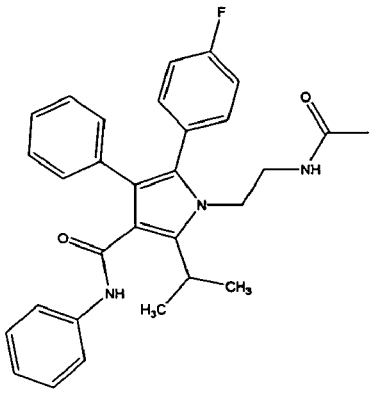
Figure 33E:
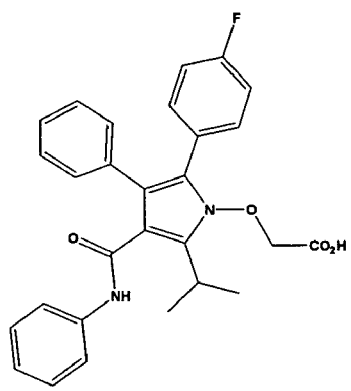
Figure 33E:
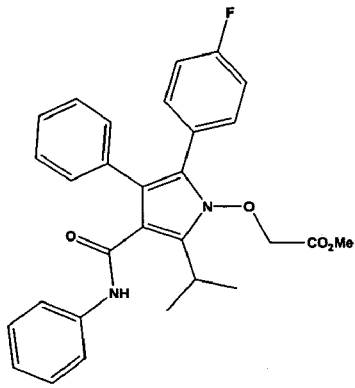
Figure 33E:
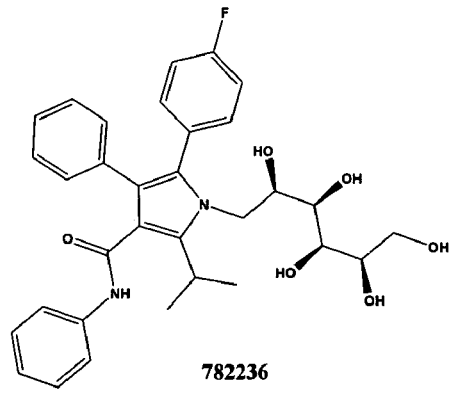
Figure 33E:
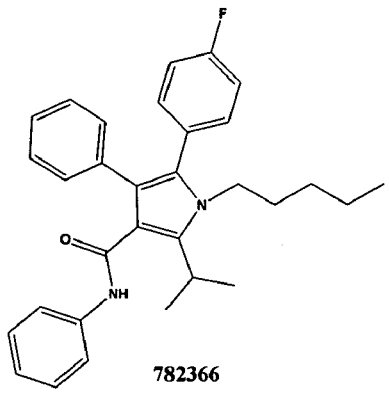
Figure 33F:
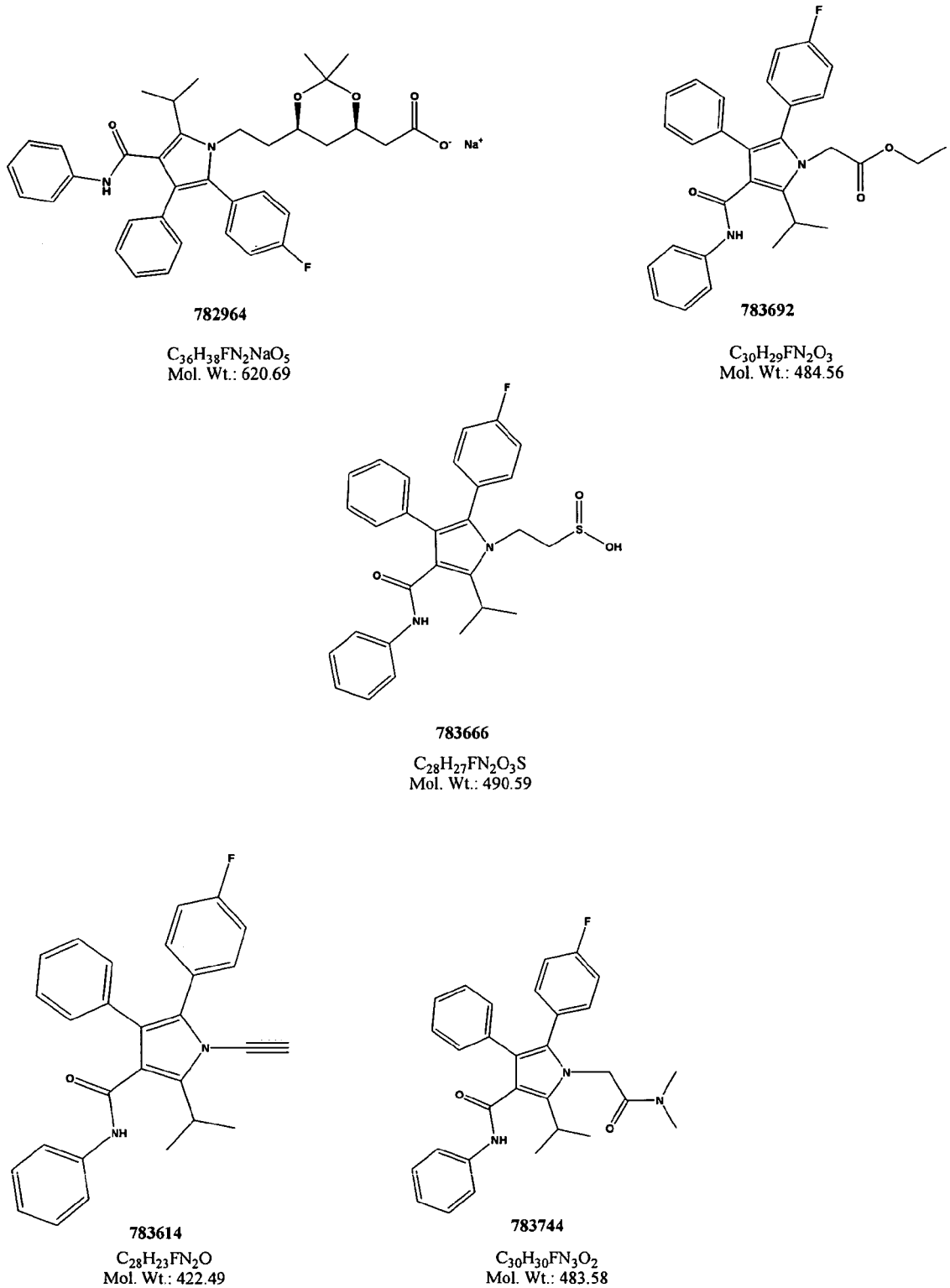
Figure 33G:
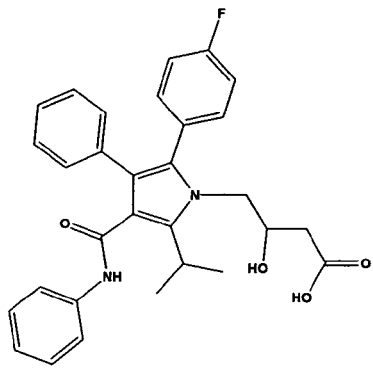
Figure 33G:
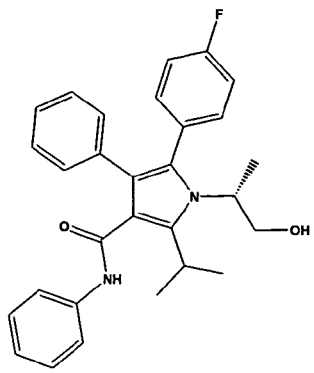
Figure 33G:
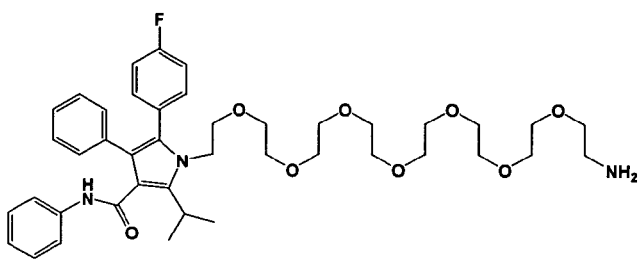
Figure 33G:
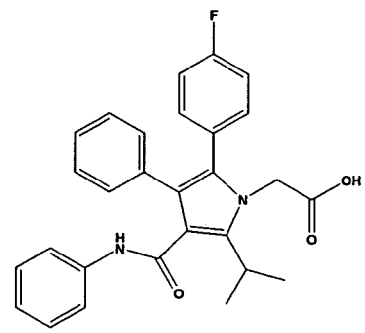
Figure 33G:
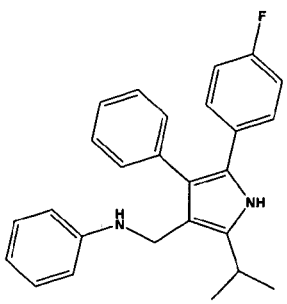
Figure 33G:
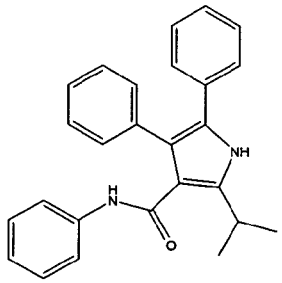
Figure 33G:
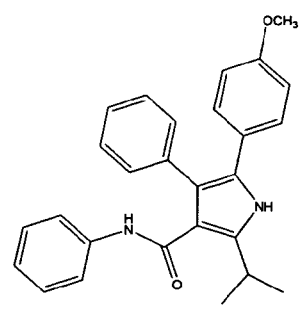
Figure 33H:
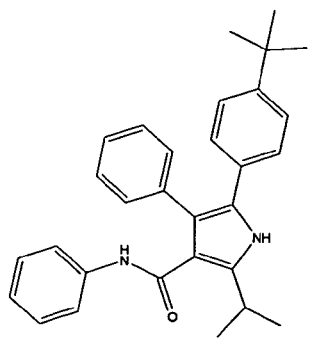
Figure 33H:
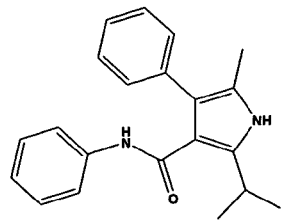
Figure 33H:
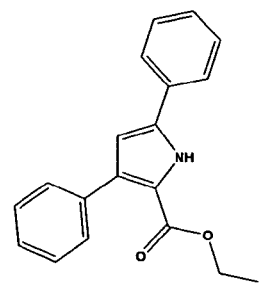
Figure 33H:
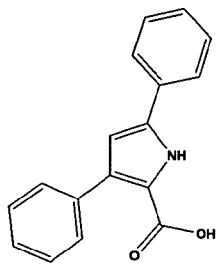
Figure 33H:
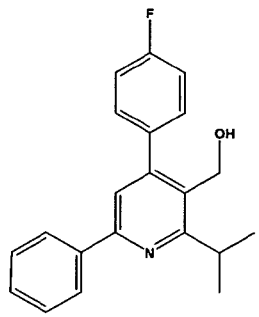
Figure 33H:
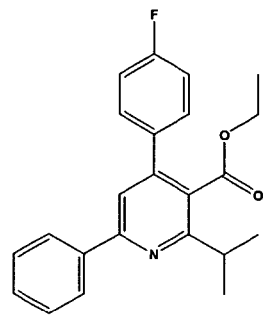

Compound number 782236 was synthesized using the scheme depicted in FIG. 30. The purification was done by concentrating down the solvent and purifying the compound on the HPLC (repeated runs about 100 mg crude per purification run). After purification and collection of the fractions, the useful fractions were purified again by HPLC using a better gradient as the separations are very tight. The solvent was then removed. Final purification involves recrystallization from MeOH and water to give pure crystalline compound 782236. Other suitable alternate synthesis schemes are depicted in FIGS. 31 and 32.

Example 3

The Affinity of the Pyrrole Compounds for PDE6D, CLB2 and HMG-CoA Reductase

The T7 phage displaying human PDE6D and CLB2 were obtained following the procedure of WO 01/18234, published Mar. 15, 2001, and U.S. patent applications Ser. No. 10/115,442, "Phage Display Affinity Filter and Forward Screen," filed Apr. 2, 2002 and Ser. No. 10/214,654, "Uncoupling DNA Insert Propagation and Protein Display," filed Aug. 7, 2002. Briefly, a T7 phage-display-based affinity chromatography procedure was used where atorvastatin was chemically coupled to a biotinylated linker moiety, which enabled the attachment of atorvastatin to streptavidin-coated magnetic beads. The atorvastatin-coated magnetic beads were used as an affinity matrix to probe the human proteome for atorvastatin-binding proteins. T7 phage display libraries that broadly cover the human proteome were mixed with the atorvastatin affinity matrix and non-binding clones were removed by washing. Atorvastatin-binding clones were eluted by incubating the affinity matrix with soluble atorvastatin. The phage eluate was then amplified by growth in E. coli and the affinity enrichment procedure was repeated. After four rounds of affinity enrichment, predominant atorvastatin-binding clones emerged and were identified by DNA sequencing as human PDE6D and CLB2. The binding of atorvastatin to PDE6D and CLB2 was further validated by competition binding assays, where the Kd's for the interactions between soluble atorvastatin (non-immobilized, no linker moiety) and the proteins were determined to be 65 nM and 500 nM for PDE6D and CLB2, respectively.

The dissociation constants, Kd's, for the interaction between the pyrrole compounds and the novel targets were obtained following the procedure of the co-pending patent applications U.S. Ser. Nos. 10/115,442, "Phage Display Affinity Filter and Forward Screen," filed Apr. 2, 2002 and 60/480,587, "Protein Family Profiling Tool and Methods," filed Jun. 20, 2003. To measure the Kd values, the T7 phage displaying human PDE6D or CLB2 were incubated with an atorvastatin-coated affinity matrix in the presence of various concentrations of a soluble (non-immobilized) pyrrole compounds of the invention, as described in detail above.

Soluble pyrrole compounds that bind PDE6D and/or CLB2 prevent binding of PDE6D and/or CLB2 phage to the affinity matrix; hence, fewer phage are recovered in the phage eluate in the presence of an effective competitor than in the absence of an effective competitor. The Kd for the interaction between the soluble pyrrole compound (competitor) molecule and PDE6D or CLB2 is equal to the concentration of soluble competitor molecule that causes a 50% reduction in the number of phage recovered in the eluate compared to a control sample lacking soluble competitor.

Data for the pyrrole compounds is provided below in Table 1. Table 1 shows the nM Kd of each listed compounds for PDE6D and CLB2. In addition, compounds 781430, 781066, 780780, 780754, 779974, 781456, 782236, 782756, 783250 and 780520 were tested in enzymatic activity-based HMG-CoA reductase assays. At concentrations up to 4 μM, none of the tested compounds inhibited the activity of HMG-CoA reductase. The Kd for atorvastatin was 65 nM for PDE6D. Blank cells indicate there was no detectable interaction while the "nd" designation indicates the Kd was not determined.

TABLE 1

| Pyrrole Compound | Kd PDE6D (nM) | Kd CLB2 (nM) | Pyrrole Compound | Kd PDE6D (nM) | Kd CLB2 (nM) |
|---|---|---|---|---|---|
| 781430 | 75 | 940 | 780910 | 280 | 1000 |
| 780754 | 58 | 1830 | 780884 | | |
| 782236 | 269 | | 780858 | 60 | 1645 |
| 780520 | 44 | 1850 | 780988 | 430 | 6000 |
| 780104 | 114 | 6067 | 781014 | | |
| 780078 | 488 | 2340 | 782028 | | |
| 780052 | 387 | 6000 | 782054 | | |
| 780026 | 6550 | | 782080 | | |
| 780000 | 598 | | 782184 | | |
| 780260 | | | 782210 | | |
| 780390 | | | 782366 | 805 | |
| 780416 | | | 782964 | 685 | 9000 |
| 780442 | | | 783016 | | |
| 780468 | | | 783094 | 900 | |
| 780494 | | | 783588 | | |
| 780650 | | 2100 | 783718 | | |

TABLE 1-continued

| Pyrrole Compound | Kd PDE6D (nM) | Kd CLB2 (nM) | Pyrrole Compound | Kd PDE6D (nM) | Kd CLB2 (nM) |
|---|---|---|---|---|---|
| 780624 | | | 783692 | | |
| 780598 | 300 | | 783666 | | 1853 |
| 780572 | | | 783640 | 290 | |
| 780546 | 880 | | 783614 | | |
| 780676 | 61 | 1893 | 783744 | | |
| 780702 | 114 | 2000 | 783770 | 1100 | 335 |
| 780728 | 350 | 1650 | 783796 | | |
| 780832 | | | 783900 | 615 | nd |
| 780962 | | | 783874 | | nd |
| 780936 | 141 | 3000 | 780234 | | |
| 780130 | | 1500 | 780364 | | 1100 |
| 780156 | | 4350 | 780338 | | |
| 780182 | | | 780312 | | |
| 780208 | | | 780286 | 2900 | |

Example 4

Preparation of Tablets

The compound 782236 (10.0 g) is mixed with lactose (85.5 g), hydroxypropyl cellulose HPC-SL (2.0 g), hydroxypropyl cellulose L-HPC, LH-22 (2.0 g) and purified water (9.0 g), the resulting mixture is subjected to granulation, drying and grading, and the thus obtained granules are mixed with magnesium stearate (0.5 g) and subjected to tablet making, thereby obtaining tablets containing 10 mg per tablet of the compound of formula 782236.

Example 5

Administering to a Subject

The tablet prepared in Example 4 is provided to a subject at time 0. One tablet every 24 h is provided for a period of one week. After administration of the third tablet, the subject is exposed to a neurodegenerative event. The treated subject exhibits symptoms of neurological disorder that are less severe compared to the subject that was not treated.

Example 6

Binding Assay with Rabbit Reticulocyte Lysate-Produced Human PDE6D

Figure 2:
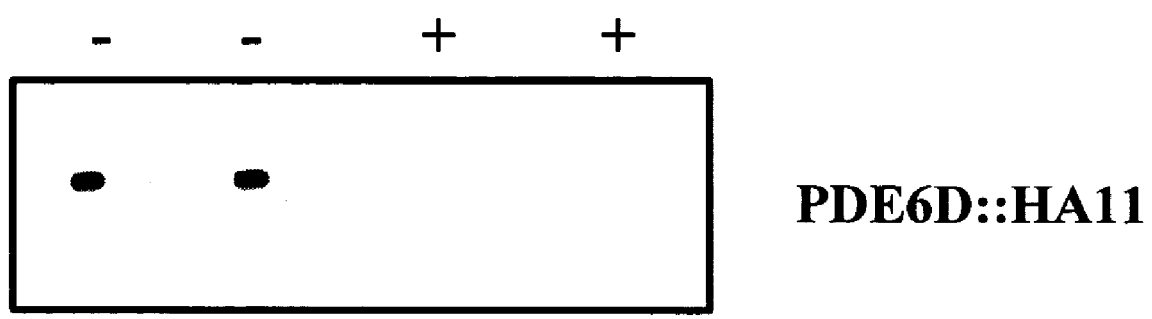
FIG. 2 shows the results of a binding experiment between atorvastatin and a PDE6D fusion protein.

The full-length coding sequence for human PDE6D was cloned into the pTNT expression vector for coupled transcription-translation (TNT) in rabbit reticulocyte lysate (RRL). The PDE6D coding sequence was fused in-frame with an HA11 epitope tag for antibody detection. The PDE6D::HA11 fusion protein produced in RRL was first analyzed by SDS-PAGE electrophoresis followed by western blotting using an HA 11 antibody to confirm the correct size of the product. The PDE6D::HA11 fusion protein was subsequently used in a binding assay with the immobilized atorvastatin bait in the absence or presence of 10 µM non-immobilized atorvastatin bait as competitor (in duplicate). This procedure allows us to recognize binding events that occur specifically to the bait in contrast to those that occur to other component of the binding reaction. In fact, if a binding event is observed in the absence of the non-immobilized bait (sample−) but it disappears when the non-immobilized bait is present during the incubation (sample+), this indicates that the binding event is bait-specific. On the contrary, if a binding event is observed with and without the non-immobilized bait in solution, this indicates that the binding event is not bait-specific (i.e. background). This procedure can also be used with other competitor molecules to identify novel interactions. The data were obtained by loading the eluates from the binding experiment on a dot blot apparatus and subsequent detection with an HA11 antibody. The results of this experiment revealed that PDE6D bound to atorvastatin as shown in FIG. 2.

Example 7

Binding Assay with Rat Brain PDE6D

Figure 3:
FIG. 3 shows the results of a binding experiment between atorvastatin and a PDE6D from rat brain.
Figure 4:
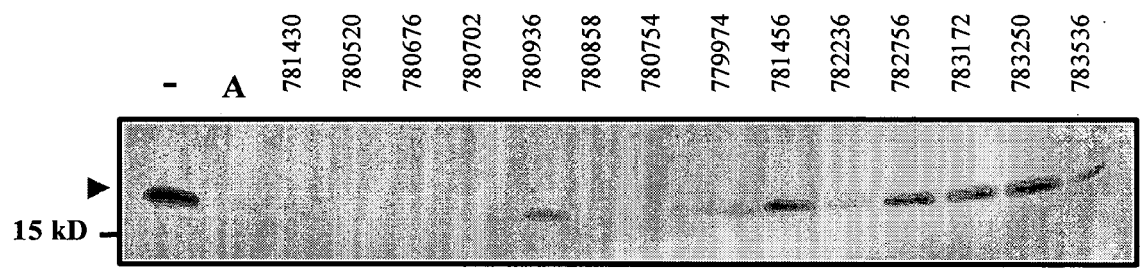
FIG. 4 shows the results of a binding experiment between atorvastatin and a PDE6D from rat brain.

The rat brain sample was homogenized in liquid nitrogen and the proteins extracted in a buffer at neutral pH containing a non-ionic detergent, a reducing agent and a mixture of protease inhibitors. After the removal of cell debris by centrifugation, the protein extract was quickly aliquoted, frozen in liquid nitrogen and stored until needed. The binding experiment was carried out using the rat brain protein extract and the immobilized atorvastatin bait in the absence or presence of 1 µM or 10 µM non-immobilized atorvastatin bait, other statins and several pyrrole compounds as competitors (see Example 6 for more information on this regard). The experiments were performed at least in triplicate and the samples pooled after elution. The data were obtained by loading the pooled eluates on a SDS-PAGE gel followed by western blot using a PDE6D-specific antibody. The results of these experiments demonstrate that rat brain PDE6D binds to atorvastatin as shown in FIGS. 3 and 4.

Example 8

Binding Assay with *E. coli*-Expressed Human PDE6D

Figure 5:
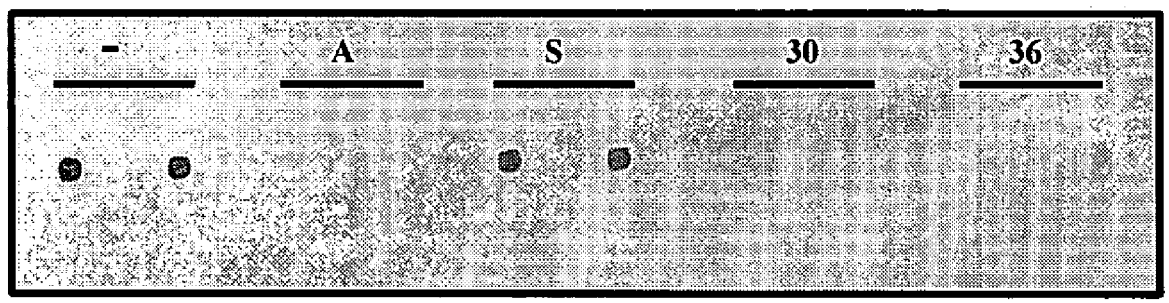
FIG. 5 shows the results of a binding experiment between atorvastatin and *E. coli* expressed human PDE6D.

The full-length coding sequence for human PDE6D was cloned into the pRSET vector for *E. coli* expression. The PDE6D coding sequence was fused in-frame with a His tag for purification purposes. The PDE6D fusion protein produced in *E. coli* was first analyzed by SDS-PAGE electrophoresis followed by western blotting using PDE6D-specific antibody to confirm the correct size of the product. The *E. coli*-synthesized PDE6D was then tested in a binding assay using the immobilized atorvastatin bait in the absence or presence of 10 µM non-immobilized atorvastatin bait, simvastatin and two pyrrole compounds as competitors (see Example 6 for more information on this regard). The experiments were performed in duplicate. The data were obtained by loading the eluates from the binding experiment on a dot blot apparatus and subsequent detection with a PDE6D-specific antibody. The results of this experiment demonstrate that *E. coli* expressed human PDE6D binds to atorvastatin as shown in the FIG. 5.

Example 9

Binding Assays with Rat Liver or Brain NQO2 and Atorvastatin Bait

Figure 6:
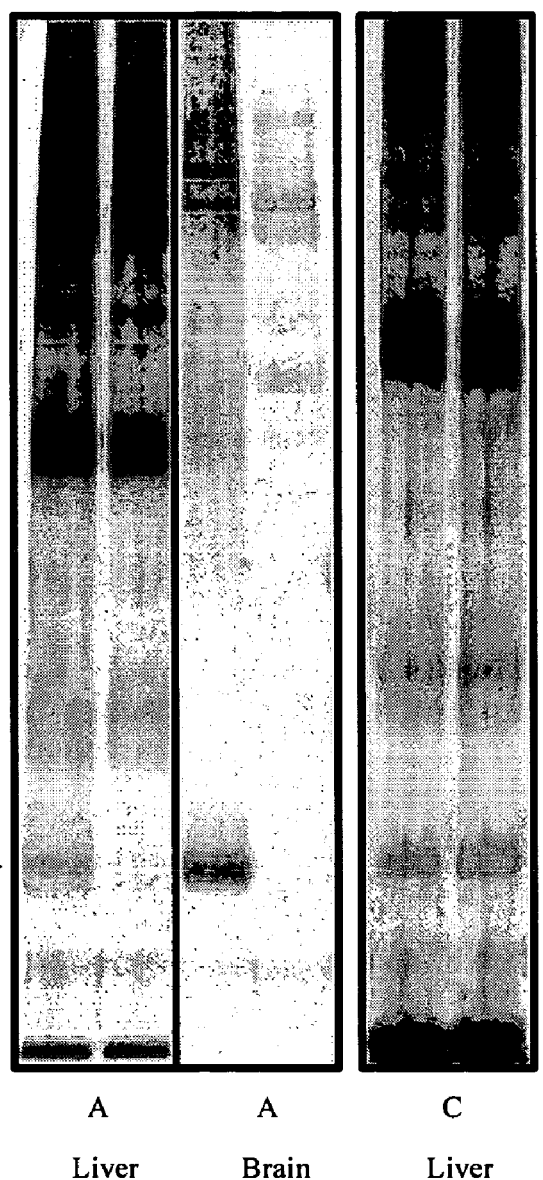
FIGS. 6A and 6B show the results of a binding experiment between atorvastatin or cerivastatin and NQO2 from rat liver or brain.
Figure 6:
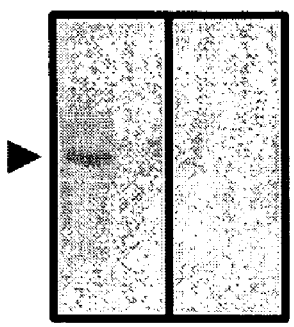

The rat liver or brain sample were homogenized and then frozen in liquid nitrogen and the proteins extracted in a buffer at neutral pH containing a non-ionic detergent, a reducing agent and a mixture of protease inhibitors. After the removal of cell debris by centrifugation, the protein extract was quickly aliquoted, frozen in liquid nitrogen and stored until needed. The binding experiment was carried out using the rat liver or brain protein extract and the immobilized atorvastatin (A) bait or cerivastatin (C) bait in the absence or presence of 10 μM non-immobilized atorvastatin bait or 10 μM non-immobilized cerivastatin bait. The experiments were performed at least in triplicate and the samples pooled after elution. The data were obtained by loading the pooled eluates on a SDS-PAGE gel followed by silver staining. NQO2 was originally identified by tryptic digest of the protein band excised form the gel and subsequent analysis by mass spectrometry. The identification was further supported by immunological detection using an NQO2-specific antibody. The results of these experiments are shown in the accompanying FIG. 6A, a silver stain and FIG. 6B, a western blot with NQO2-specific antibody. Other statins (i.e. simvastatin, rosuvastatin, pravastatin, cerivastatin and fluvastatin) have also been tested as competitors for binding to NQO2 at a concentration of 10 μM but did not display evidence of binding.

Figure 7:
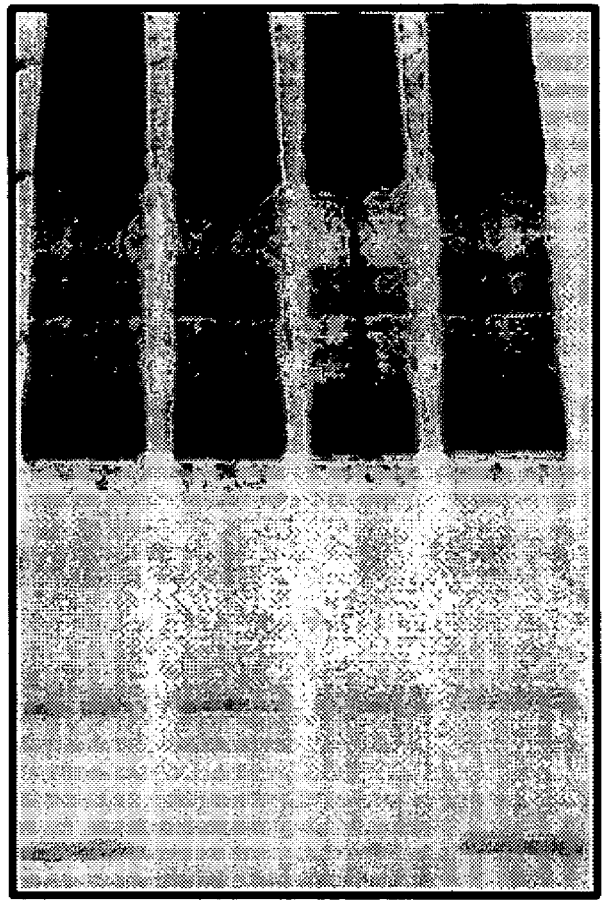
FIG. 7 shows the results of a binding curve assay between atorvastatin and NQO2 from rat liver protein extract.

The apparent Kd of the interaction between the rat liver NQO2 and the atorvastatin bait was evaluated semi-quantitatively by performing a binding curve assay in which decreasing amount (from 10 μM to 0.1 μM) of the non-immobilized atorvastatin bait were present during the binding reaction. The data were obtained by loading the pooled eluates on a SDS-PAGE gel followed by silver staining. The apparent Kd was estimated to be around 500 nM based on densitometric scanning of the gel image. The result of this experiment is shown in FIG. 7.

Figure 8:
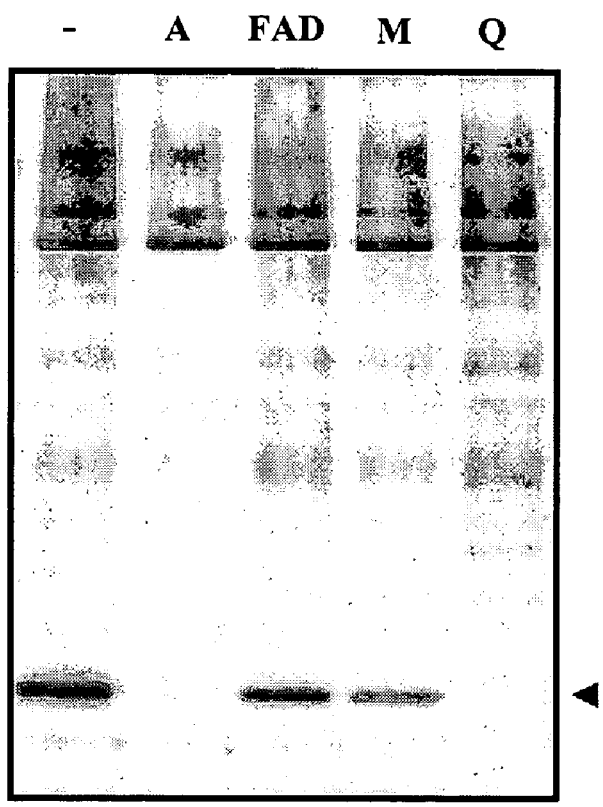
FIG. 8 show the results of a binding competition assay between NQO2 from rat brain protein extract, immobilized atorvastatin, and various binding competitors.

The crystal structure of the NQO2 protein has shown that this protein contains three distinct binding pockets. The first binds to the electron donor NRH (and the potent inhibitor quercetin), the second binds to the substrate menadione (vitamin K3) and the third binds to the FAD cofactor. To identify in which pocket atorvastatin binds, we performed a binding experiment using rat brain protein extract, atorvastatin bait and several competitors including: 10 μM non-immobilized atorvastatin (as a control), 100 μM menadione, 10 μM quercetin and 100 μM FAD. The data were obtained by loading the pooled eluates on a SDS-PAGE gel followed by silver staining. The results of this experiment are shown in the accompanying FIG. 8. The data show that atorvastatin binds the electron donor NRH pocket as quercetin does likely inhibiting the function of NQO2.

Figure 9:
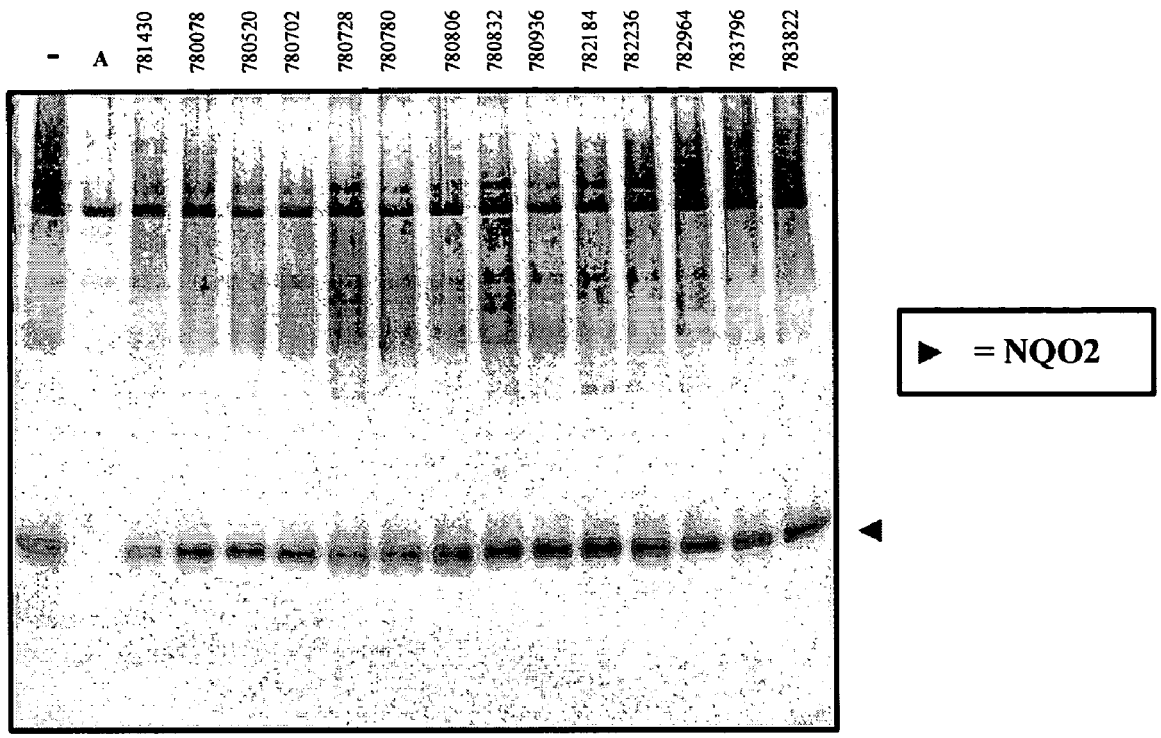
FIG. 9 shows the results of a binding competition assay between NQO2 from rat brain protein extract, immobilized atorvastatin and various compounds described herein.

To test if any of the compounds were able to compete with atorvastatin in binding NQO2 we carried out a binding experiment using rat brain protein extract, atorvastatin bait and several compounds at 10 μM concentration. The data were obtained by loading the pooled eluates on a SDS-PAGE gel followed by silver staining. The results of this experiment are shown in the accompanying FIG. 9.

Example 10

Efficacy Studies of Compounds in the Rodent MCAO Model

Two doses of compounds, 1 mg/kg or 10 mg, were tested in a standardized rat model of focal cerebral ischemia produced by permanent occlusion of the right middle cerebral artery (MCA) plus one hour of tandem carotid artery occlusion according to Chen et al. In a blinded random investigation, 782236, 781430 and atorvastatin were injected subcutaneously (S.C.) as bolus injection at 2 hrs pre MCA occlusion (MCAO) and 1 hour post occlusion (at time of carotid reperfusion) and 24 hours post MCAO. Control animals were injected with the vehicle for the test compounds. Survival was maintained for 48 hrs. The cortical infarction sizes were used as endpoints for efficacy evaluation.

There was a statistically significant difference of infarct volumes from control (154.92±9.21 mm$^3$) for groups Lo A 1 mg/kg (71.32±36.98 mm$^3$) and Hi B 10 mg/kg (65.99±25.01 mm$^3$, p>0.05, student t tests). These values represent 53% and 57% reduction in infarct volume from control, respectively.

Methods

Animal Preparation and Middle Cerebral Artery Occlusion. Male, adult, Sprague-Dawley rats (Charles River), weighing 300-400 grams, were used for the study. All animals were acclimated at least for five days before entering the study. Animals were housed in a standard animal facility and fed with commercial rodent chow ad libitum. All animals were anesthetized via intramuscular injection (4 mL/kg) of "cocktail" containing ketamine (25 mg/mL), xylazine (1.3 mg/mL) and acepromazine (0.33 mg/mL). Both carotid arteries were separated with great caution to minimize the vagal nerve stimulation. The right proximal MCA trunk was exposed through a subtemporal craniectomy without transecting the facial nerve. The artery was then occluded by micro-bipolar coagulation 1 mm above the inferior cerebral vein. Immediately following MCA occlusion, both of the common carotid arteries were occluded for 1 hour using surgical aneurysm micro-clips (ROBOZ INC). Animals were put into temperature regulated recovery chamber for 1 hour before the clips were removed from the common carotid arteries. Body temperature was maintained at 37±0.5° C. during the surgery using a heating blanket connected to a temperature controller.

Experimental Groups. A total of 50 animals divide into eight experimental groups of animals were delineated according to the following:
Group A=Compound 782236, either low A=1 m/kg high A=10 mg/kg
Group B=Compound 781430, low B and high B
Group C=Compound atorvastatin low C, and high C
Group D=Compound Vehicle 1 ml/kg body weight
Table 2 depicts the groups and administration route.

TABLE 2

| Group | N | Test Articles | Dose | Route | Time Period |
|---|---|---|---|---|---|
| Control | 15 | Vehicle | No TX | SC | 2 Hours Pre MCAo |
| | | | | | 1 Hour Post MCAo |
| | | | | | 24 Hours Post MCAo |
| Lo A | 5 | 782236 | 1 mg/kg | SC | 2 Hours Pre MCAo |
| | | | | | 1 Hour Post MCAo |
| | | | | | 24 Hours Post MCAo |
| Lo B | 5 | 779974 | 1 mg/kg | SC | 2 Hours Pre MCAo |
| | | | | | 1 Hour Post MCAo |
| | | | | | 24 Hours Post MCAo |
| Lo C | 5 | Atorvastatin | 1 mg/kg | SC | 2 Hours Pre MCAo |
| | | | | | 1 Hour Post MCAo |
| | | | | | 24 Hours Post MCAo |
| Hi A | 5 | 782236 | 10 mg/kg | SC | 2 Hours Pre MCAo |
| | | | | | 1 Hour Post MCAo |
| | | | | | 24 Hours Post MCAo |
| Hi B | 5 | 779974 | 10/mg/kg | SC | 2 Hours Pre MCAo |
| | | | | | 1 Hour Post MCAo |
| | | | | | 24 Hours Post MCAo |

Compound Administration and Storage. In a blinded random investigation, all animals were injected with the compound(s) or vehicle via S.C. as bolus injection at 2 hours pre, 1 hour post and 24 hours post-MCAo.

Body Temperature. All animal body temperatures were monitored throughout the surgery and maintained near normal values (36.8-37.5° C.). Body temperature was documented at the time of MCAo.

Body Weight. Animal body weights were measured and documented at the time of surgery.

Infarct Measurement. Forty-eight hours following MCAo, animals were euthanized with inhalation of $CO_2$. Brains were removed and chilled in ice saline for 10 min. The brains were put in a metal rodent brain slicer. Each rat brain was cut coronally into 7 sections, with each section being 2 mm thick. The brain sections were immersed in 2% TTC solution for 30 min at 37° C. The areas of cerebral infarcts were determined on seven slices, using a computer-interfaced imaging system, Image-Pro® Plus, Version 4.4 for Windows (Media Cybernetics, MD). Infarct areas were then summed among slices and multiplied by slice thickness to give the total infarct volume.

Statistics. All data are expressed as mean±SEM. Infarct volume was analyzed using Student t Test. A p value of ≦0.05 was considered a statistically significant difference. All statistical analyses were performed with the software package JMP version 4.0 (SAS Institute Inc., Cary, N.C.).

Results

Mortality. Due to the high mortality rate associated with the high A (782236, dosage 10 mg/kg) group, data points for this group are not available. Three animals received high A and died within the 24-hour period after the second injection. One animal in the control group died within the first 24 hours after MCAo. All other animals survived the 48-hour trial.

Infarct Volume. The infarct was found to be limited to the cortex supplied by the distal branches of middle cerebral artery without involving the striatum. Infarct volumes of groups Lo B (781430, dosage 1 mg/kg), Lo C (atorvastatin, dosage 1 mg/kg) and Hi C (atorvastatin, dosage 10 mg/kg) were not significantly different from controls. In groups Lo A (782236, dosage 1 mg/kg) and Hi B (781430, dosage 10 mg/kg), there were 53% and 57% reductions of infarct volumes, respectively, when compared with control. The results are shown in Table 3.

TABLE 3

| Group | Infarct Volume (mm³) |
|---|---|
| Control | 154.92 ± 9.21 |
| LoA | 71.32 ± 36.98 |
| LoB | 152.83 ± 13.78 |
| LoC | 158.06 ± 32.83 |
| HiB | 65.99 ± 25.01 |
| HiC | 124.71 ± 17.31 |

Data are mean ± SEM

Figure 10:
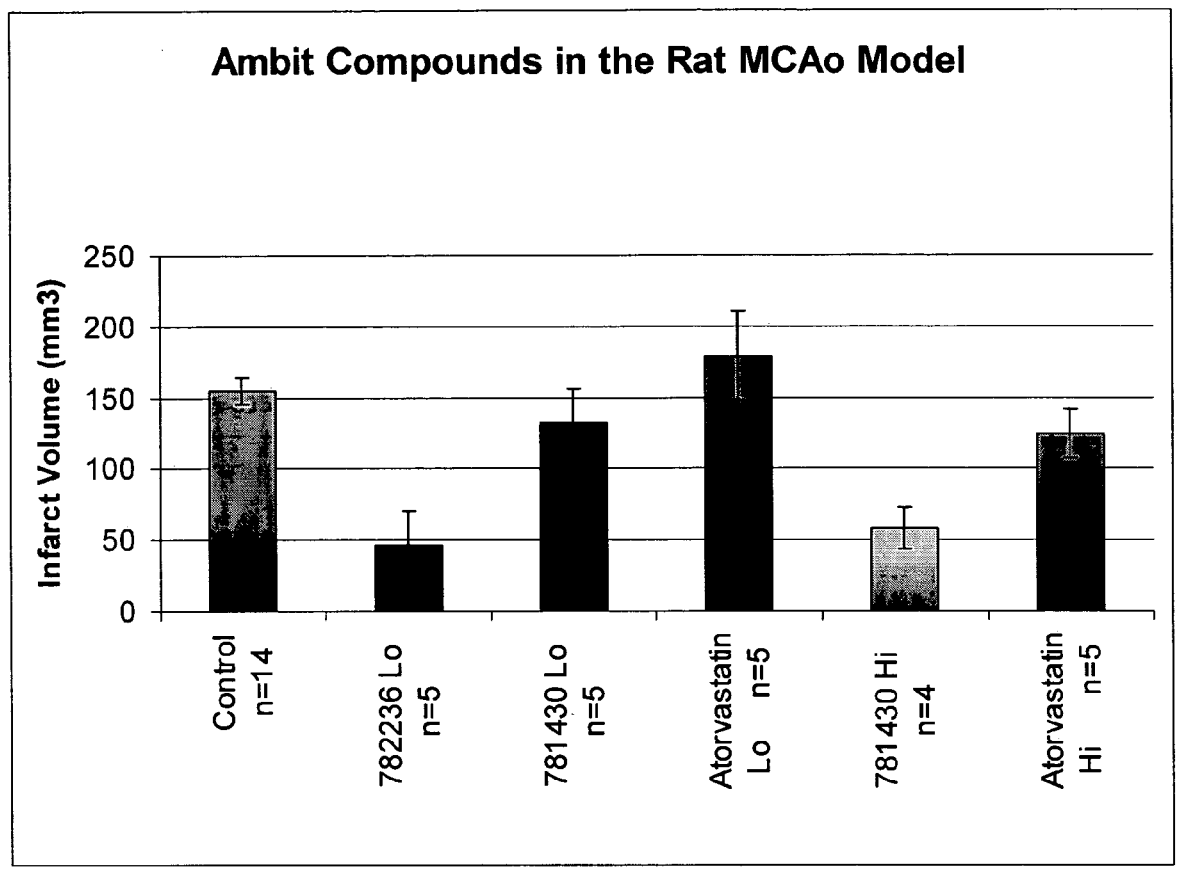
FIG. 10 shows the results of infarct volumes in animals subjected to middle cerebral artery (MCA) occlusion, followed by 48-hour recovery.

In FIG. 10, the results of infarction volumes in treated animals subjected to MCAo, followed by 48 h recovery are shown. Compared to control, group A Lo had a 53% reduction in infarct size and group B Hi had a 57% reduction. These differences were statistically significant (p>0.05, student t test). Data are mean±SEM.

Body Weight. There were no differences in body weight between all groups at the beginning of the study.

TABLE 4

| Group | Body Weight (g) |
|---|---|
| Control | 334.26 ± 10.53 |
| LoA | 353.80 ± 19.38 |
| LoB | 363.75 ± 3.75 |
| LoC | 305.83 ± 3.36 |

TABLE 4-continued

| Group | Body Weight (g) |
|---|---|
| HiB | 285.00 ± 14.71 |
| HiC | 305.00 ± 2.82 |

Data are mean ± SEM. See Table 4.

Body weights of animals subjected to MCA occlusion, followed by 24 h recovery. Body weights were taken prior to MCAo. Data are mean±SEM.

Conclusion. The infarct volumes in groups Lo A and Hi B were reduced by 53% and 57%, respectively, when compared with control. There was a 60% mortality rate in-group Hi A.

Example 11

Efficacy Studies of Compounds in the Rodent MCAO Model

The compounds were tested on a standardized rodent focal cerebral ischemia model produced by permanent occlusion of the right middle cerebral artery (MCA) plus one hour of tandem carotid artery occlusion according to Chen et al. A total of 96 animals underwent MCAo using subcutaneous administration of all test articles, according to the experimental design illustrated in Table 5 below. Three compounds at one predetermined dose were compared to vehicle and assigned to three different time schedules of administration relative to the time of MCAo. In this study, group A=782236, B=781430 C=atorvastatin, and D=Vehicle (1 ml/kg). The time schedules for administration of all treated groups were divided as follows:

a. 2 hrs pre, 3 hrs post, & 25 hrs post
b. 1 hr post, 3 hrs post, & 25 hrs post
c. 3 hrs post, 6 hrs post, & 25 hrs post A second group of eighteen animals were used to test compound A (782236) using the treatment schedule, shown (a, b & c) above via intravenous (I.V.) administration. Groups of n=5 animals per treatment time period with compound A and 3 animals per control group via tail vein.

Control animals were injected with the vehicle for the test compounds. Survival was maintained for 48 hrs. The infarct sizes were used as endpoints for efficacy evaluation.

The results of this study established a time correlation exemplified by efficacy in reducing infract size using these compounds when delivered up to 3 hours post middle cerebral artery occlusion in this rat model.

Methods

Animal Preparation and Middle Cerebral Artery Occlusion. Male, adult, Sprague-Dawley rats (Charles River), weighing 300-400 grams, were used for the study. All animals were acclimated at least for five days before entering the study. Animals were housed in a standard animal facility and fed with commercial rodent chow ad libitum. All animals were anesthetized via intramuscular injection (4 mL/kg) of "cocktail" containing ketamine (25 mg/mL), xylazine (1.3 mg/mL) and acepromazine (0.33 mg/mL). Both carotid arteries were separated with great caution to minimize the vagal nerve stimulation. The right proximal MCA trunk was exposed through a subtemporal craniectomy without transecting the facial nerve. The artery was then occluded by micro-bipolar coagulation 1 mm above the inferior cerebral vein. Immediately following MCA occlusion, both of the common carotid arteries were occluded for 1 hour using surgical aneurysm micro-clips (ROBOZ INC).

Animals were put into temperature regulated recovery chamber for 1 hour before the clips were removed from the common carotid arteries. Body temperature was maintained at 37±0.5° C. during the surgery using a heating blanket connected to a temperature controller.

Experimental Groups and Compound Administration. A total of 96 animals underwent MCAo using subcutaneous administration of all test articles, according to the experimental design illustrated in Table 5 below. Three compounds at one predetermined dose were compared to vehicle and assigned to three different time schedules of administration relative to the time of MCAo. In this study, group A=782236, B=781430 C=atorvastatin and D=Vehicle. The time schedules for administration of all treated groups were divided as follows:
a. 2 hrs pre, 3 hrs post, & 25 hrs post
b. 1 hr post, 3 hrs, & 25 hrs post
c. 3 hrs post, 6 hr post, & 25 hr post A second group of eighteen animals were used to test compound A (782236) using the treatment schedule, shown (a, b & c) above via I.V. administration. Groups of n=5 animals per treatment time period with compound A and 3 animals per control group via tail vein.

TABLE 5

Compound Administration

| Compound | Route | Schedule/Dosage | | |
|---|---|---|---|---|
| | | pre2 | post3 | post25 |
| 782236 | IV | 1 mg/kg | 0.5 mg/kg | 0.5 mg/kg |
| 782236 | SC | 1 mg/kg | 0.5 mg/kg | 0.5 mg/kg |
| 779974 | SC | 10 mg/kg | 5 mg/kg | 5 mg/kg |
| Atorvastatin | SC | 10 mg/kg | 5 mg/kg | 5 mg/kg |
| | | post1 | post3 | post25 |
| 782236 | SC | 1 mg/kg | 0.5 mg/kg | 0.5 mg/kg |
| 779974 | SC | 10 mg/kg | 5 mg/kg | 5 mg/kg |
| Atorvastatin | SC | 10 mg/kg | 5 mg/kg | 5 mg/kg |
| | | post3 | post6 | post25 |
| 782236 | SC | 1 mg/kg | 0.5 mg/kg | 0.5 mg/kg |
| 779974 | SC | 10 mg/kg | 5 mg/kg | 5 mg/kg |
| Atorvastatin | SC | 10 mg/kg | 5 mg/kg | 5 mg/kg |

Body Temperature. The body temperature of all animals was monitored throughout the surgery and maintained near normal values (36.8-37.5° C.). Body temperature was documented at the time of MCAo.

Figure 11:
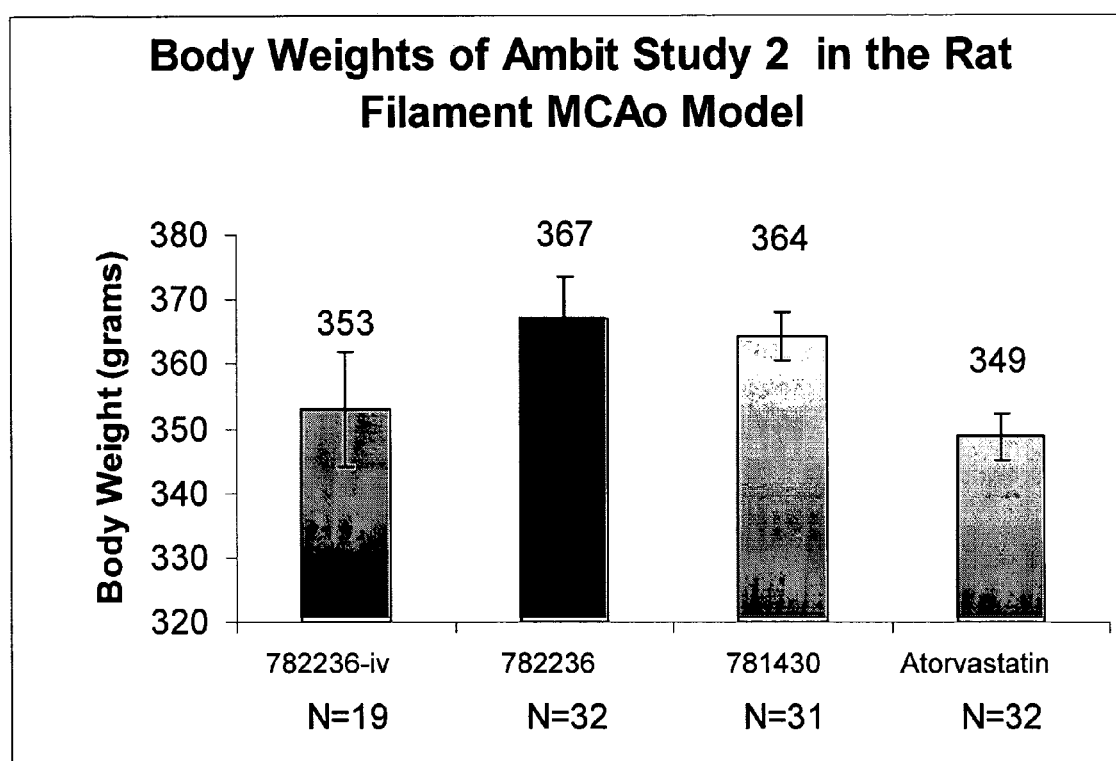
FIG. 11 shows the animal body weights at the time of surgery in a rat filament MCA occlusion study.

Body Weight. Animal body weights were measured and documented at the time of surgery. See FIG. 11. There were no statistical differences in body weights between all Groups.

Infarct Measurement. Forty-eight hours following MCAo, animals were euthanized with inhalation of $CO_2$. Brains were removed and chilled in ice saline for 10 min. The brains were put in a metal rodent brain slicer. Each rat brain was cut coronally into 7 sections, with each section being 2 mm thick. The brain sections were immersed in 2% TTC solution for 30 min at 37° C. The areas of cerebral infarcts were determined on seven slices, using a computer-interfaced imaging system, Image-Pro® Plus, Version 4.4 for Windows (Media Cybernetics, MD). Infarct areas were then summed among slices and multiplied by slice thickness to give the total infarct volume.

Statistics. All data are expressed as mean±SEM. In Section A, infarct volume was analyzed using Student t Test. A p value of ≦0.05 was considered a statistically significant difference. All statistical analyses were performed with the software package JMP version 4.0 (SAS Institute Inc., Cary, N.C.).

Results

Mortality. One animal in the control group died within the first 24 hours after MCAo. All other animals survived the 48-hour trial.

Figure 12:
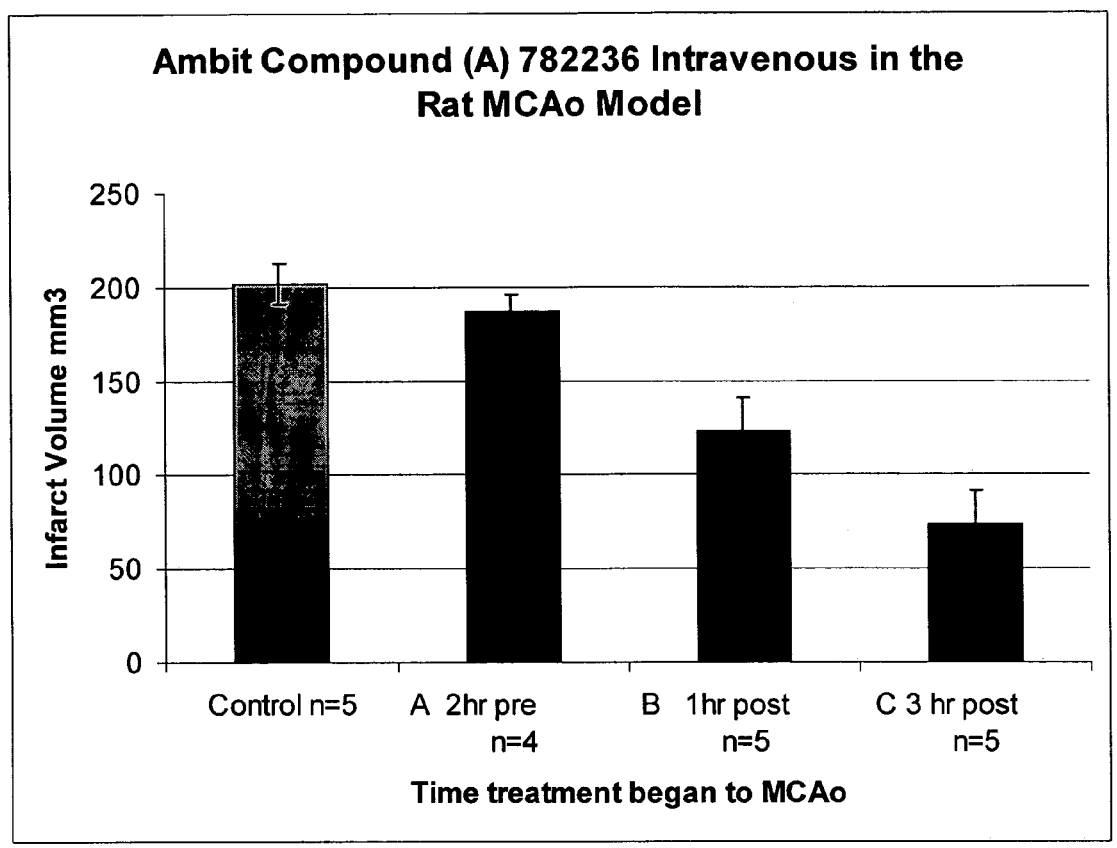
FIG. 12 shows the results of intravenous administration of 782236 in a rat MCA occlusion study.

Infarct Volume. The infarct was found to be limited to the cortex supplied by the distal branches of middle cerebral artery without involving the striatum. The results of infarct volumes of all groups comparing compound to vehicle treated control are depicted below. The treatment paradigm for each compound is as follows:
a. 2 hrs pre, 3 hrs post, & 25 hrs post
b. 1 hr post, 3 hrs post, & 25 hrs post
c. 3 hrs post, 6 hrs post, & 25 hr post Compound A 782236 IV: FIG. 12 shows the results of intravenous administration of 782236. Infarction volumes observed in groups b (122.8±17.9 $mm^3$) and c (73.8±18.1 $mm^3$) were statistically different than control (vehicle) treated animals (202.5±18.1 $mm^3$) while group a animals (186.8±9.2 $mm^3$) did not show statistical difference from control.

Figure 13:
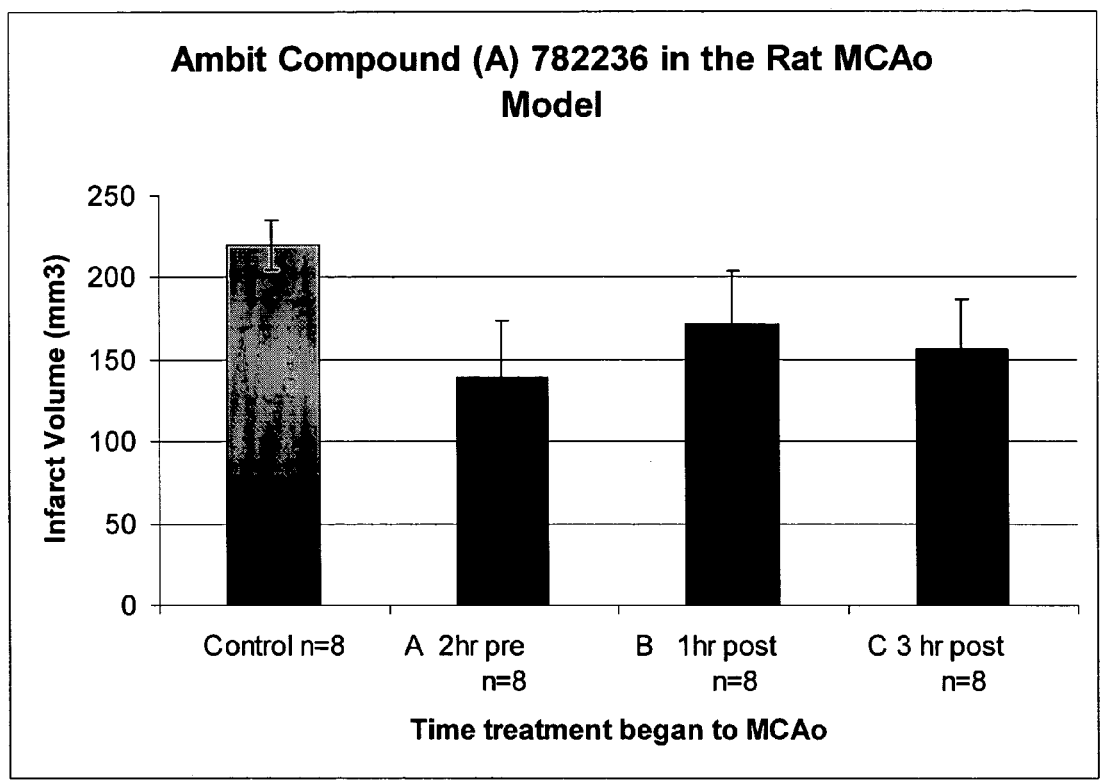
FIG. 13 shows the results of subcutaneous administration of 782236 in a rat MCA occlusion study.

Compound A 782236: FIG. 13 shows that the infarction volume observed in group a (138.6±35.13 $mm^3$) was statistically different than control (vehicle) treated animals (220.39±14.48 $mm^3$) while those observed in groups b (171.04±33.04 $mm^3$) and c (155.53±29.66 $mm^3$) animals did not show statistical difference from control.

Figure 14:
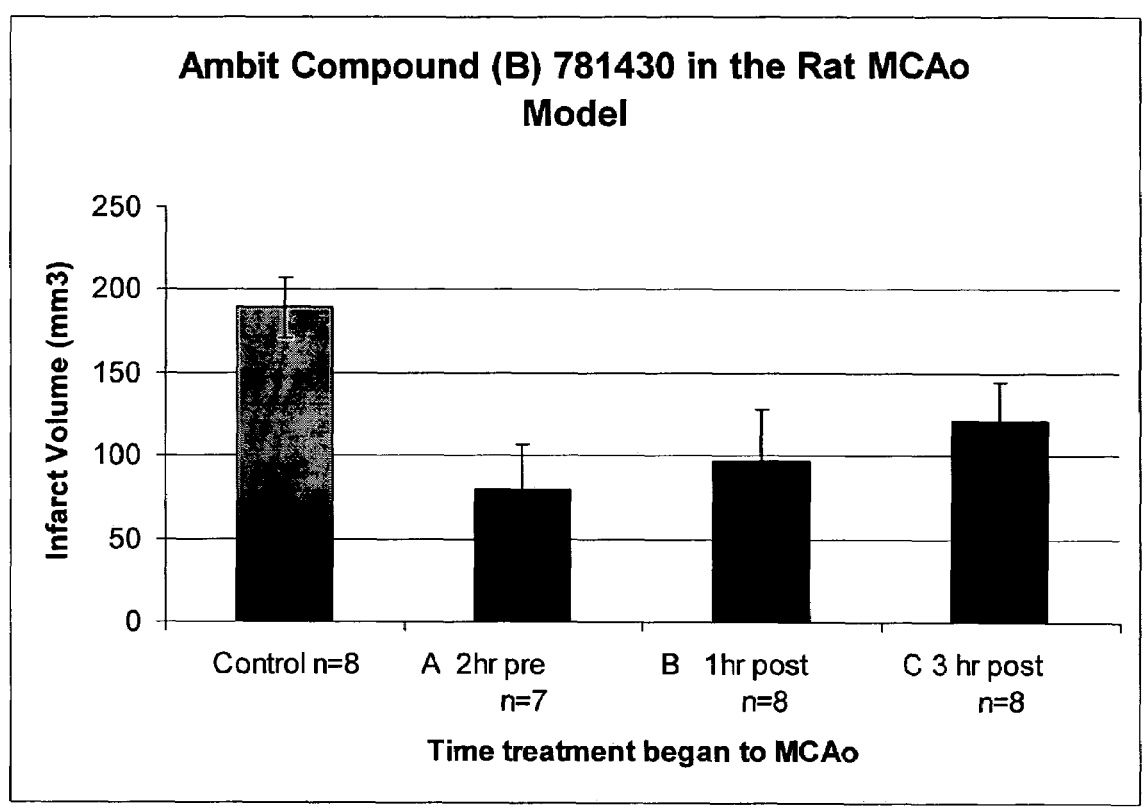
FIG. 14 shows the results of subcutaneous administration of 779974 in a rat MCA occlusion study.

Compound B 781430: FIG. 14 shows that the infarction volume observed in groups a (78.89±28.46 $mm^3$), b (96.51±31.62 $mm^3$) and c (121.39±22.53 $mm^3$) were statistically different than control (vehicle) treated animals (189.16±18.47 $mm^3$).

Figure 15:
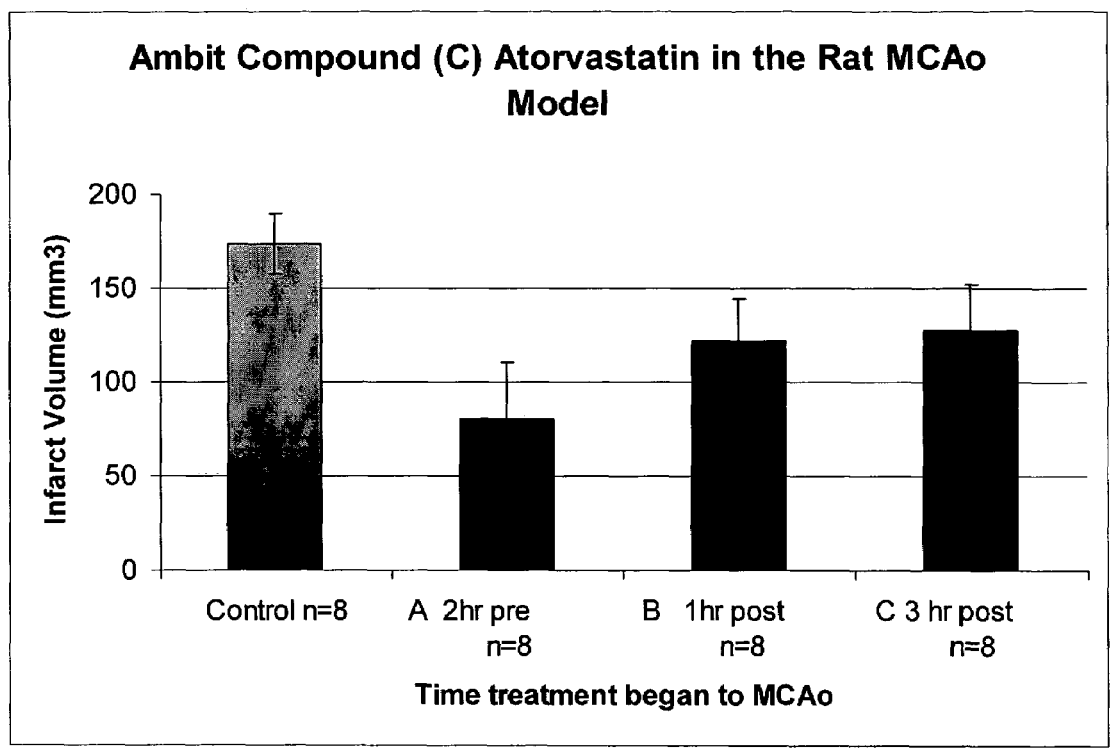
FIG. 15 shows the results of subcutaneous administration of atorvastatin in a rat MCA occlusion study.

Compound C atorvastatin: FIG. 15 shows that the infarction volume observed in group a (80.35±30.41 $mm^3$) was statistically different than control (vehicle) treated animals (174.36±16.670 $mm^3$) while the infarction volumes observed in groups b (121.52±22.58 $mm^3$) and c (127.16±25.77 $mm^3$) animals did not show statistical difference from control.

Figure 16:
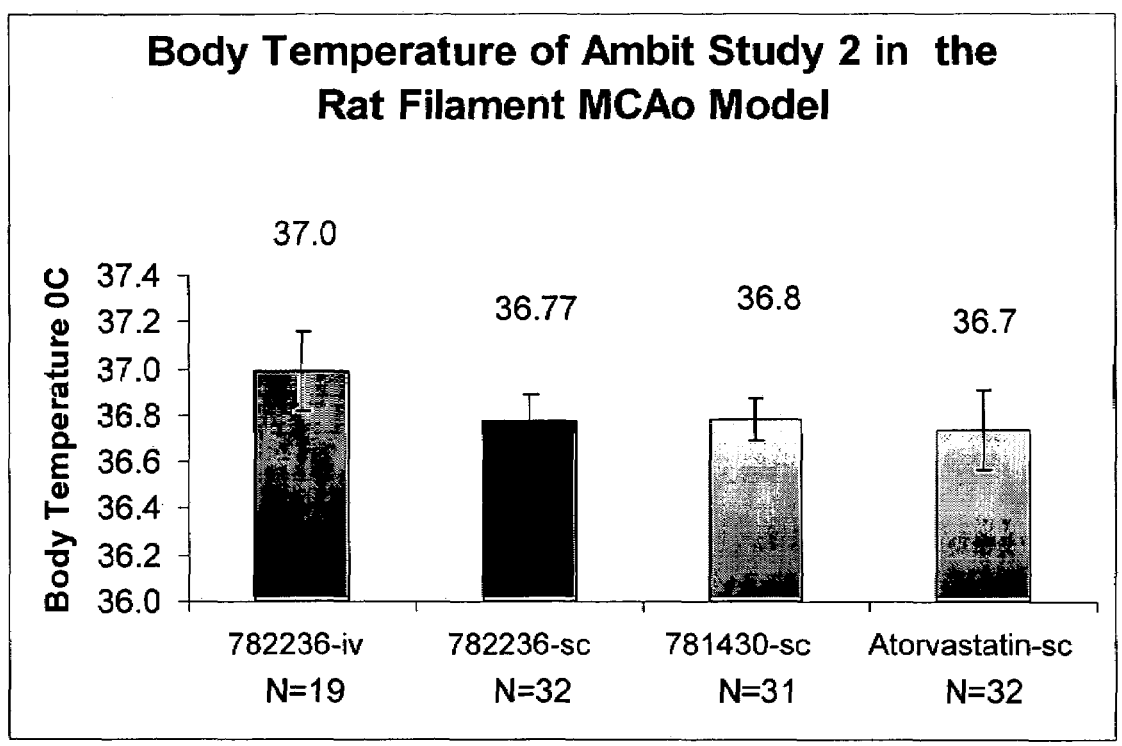
FIG. 16 shows the animal body temperatures measured at the time of MCA occlusion in a rat filament MCA occlusion study.

As shown in FIG. 16, there were no differences in body temperature between all groups at the beginning of the study. Data are mean±SEM.

Example 12

Efficacy Study of Compounds in the Rodent MCAO (Tamura) Model

The Tamura model of MCAo was utilized to determine the effect of pyrrole compounds in alleviating the neurological deficit demonstrated as motor skill performance. Behavioral assessment as well as infarct volume of compound-treated animals in comparison to control (vehicle) volume animals was used for evaluating compound efficacy over a 7 day period.

Methods

Animal Preparation. Eighty, adult, Sprague-Dawley rats (Taconic Farms), weighing 300-350 g, were used for the study. Animals were housed in a standard animal facility and fed with commercial rodent chow ad libitum. Extra animals were ordered to allow for proper randomization and mortality from the surgical procedures. The rats were approximately 10 weeks of age when they arrived at the laboratory.

All animals were housed and handled for behavioral assessment for 7 days prior to surgery for acclimation purposes. At the end of the training period, animals were randomized and assigned to different groups. Animals were given a unique identification number by tail marking. Tail number and cage cards will identify the animals.

Surgical Preparation. Middle Cerebral Artery Occlusion (MCAo), Tamura Model. Focal cerebral infarcts were made by permanent occlusion of the proximal right middle cerebral artery using a modification of the method of Tamura et al. Male Sprague-Dawley rats (300-350 g) were anesthetized with 2% isoflourane in 50% Air/50% $O_2$, and maintained with 1-1.5% isoflourane. The temporalis muscle was bisected and reflected through an incision made midway between the eye and the eardrum canal. The proximal MCA was exposed through a subtemporal craniectomy without removing the zygomatic arch and without transecting the facial nerve. The artery was then occluded by microbipolar coagulation from just proximal to the olfactory tract to the inferior cerebral vein, and transected. Body temperature was maintained at 38° C.±1 throughout the entire procedure. Animals were euthanatized at various time periods after MCA occlusion and the brains are removed for histological analysis.

Cerebral Blood Flow Measurement. Blood Flow Monitoring took place in one group of forty animals to determine the effects of the three experimental compounds (782236, 781430 and atorvastatin) on cerebral blood flow at certain times in relation to the MCAo. A Perimed Laser Doppler System 500 was used to determine percent changes in cerebral blood before MCAo, sixty minutes post MCAo and then days 1 and 5 after MCAo.

Animals were briefly anesthetized with isoflourane and a primed flow probe was inserted through a burr hole made approximately at the following stereotaxic coordinates on the ipsilateral side of the MCAo: −1.0 millimeters to bregma and +6 mm lateral to the midline. The tip of the probe was inserted 1 mm and fixed in place using cyanoacrylate glue. Recordings were made over a 5-minute period. The muscle flap and skin was sutured with running 4-0 silk and animals were returned to their cages. The results of the groups treated with the 3 test compounds was compared to Vehicle treated rats.

Behavioral Analysis. Two behavioral tests were performed, the limb placing and body swing test. This test was performed immediately after surgery and days 1,3,7 after MCAo.

Limb Placing. The limb placing tests were divided into both forelimb and hindlimb tests. For the forelimb-placing test, the examiner held the rat close to a tabletop and scored the rat's ability to place the forelimb on the tabletop in response to whisker, visual, tactile, or proprioceptive stimulation. Similarly, for the hindlimb placing test, the examiner assessed the rat's ability to place the hindlimb on the tabletop in response to tactile and proprioceptive stimulation. Separate sub scores were obtained for each mode of sensory input and added to give total scores (for the forelimb placing test: 0=normal, 10=maximally impaired; for the hindlimb placing test: 0=normal, 6=maximally impaired). Typically, there was a slow and steady recovery of limb placing behavior during the first month after stroke.

Table 6 shows the measured scores of the forelimb placing tests where compounds 782236 (A), 781430 (B) and atorvastatin (C) were administered three hours after MCAo. The results show an improvement after treatment by the pyrrole compounds and atorvastatin.

TABLE 6

| Day | | D0 | D1 | D3 | D7 |
|---|---|---|---|---|---|
| | Control | | | | |
| AVG | | 0 | 8.6 | 8.5 | 7.7 |
| SEM | | 0 | 0.3 | 0.3 | 0.3 |
| | A | | | | |
| AVG | | 0 | 8.4 | 6.7 | 5.9 |
| SEM | | 0 | 0.34 | 0.27 | 0.26 |
| | B | | | | |
| AVG | | 0 | 8.9 | 7.6 | 4.3 |
| SEM | | 0 | 0.4 | 0.6 | 0.5 |
| | C | | | | |
| AVG | | 0 | 9.2 | 7.3 | 5.6 |
| SEM | | 0 | 0.2 | 0.6 | 0.7 |

Figure 17:
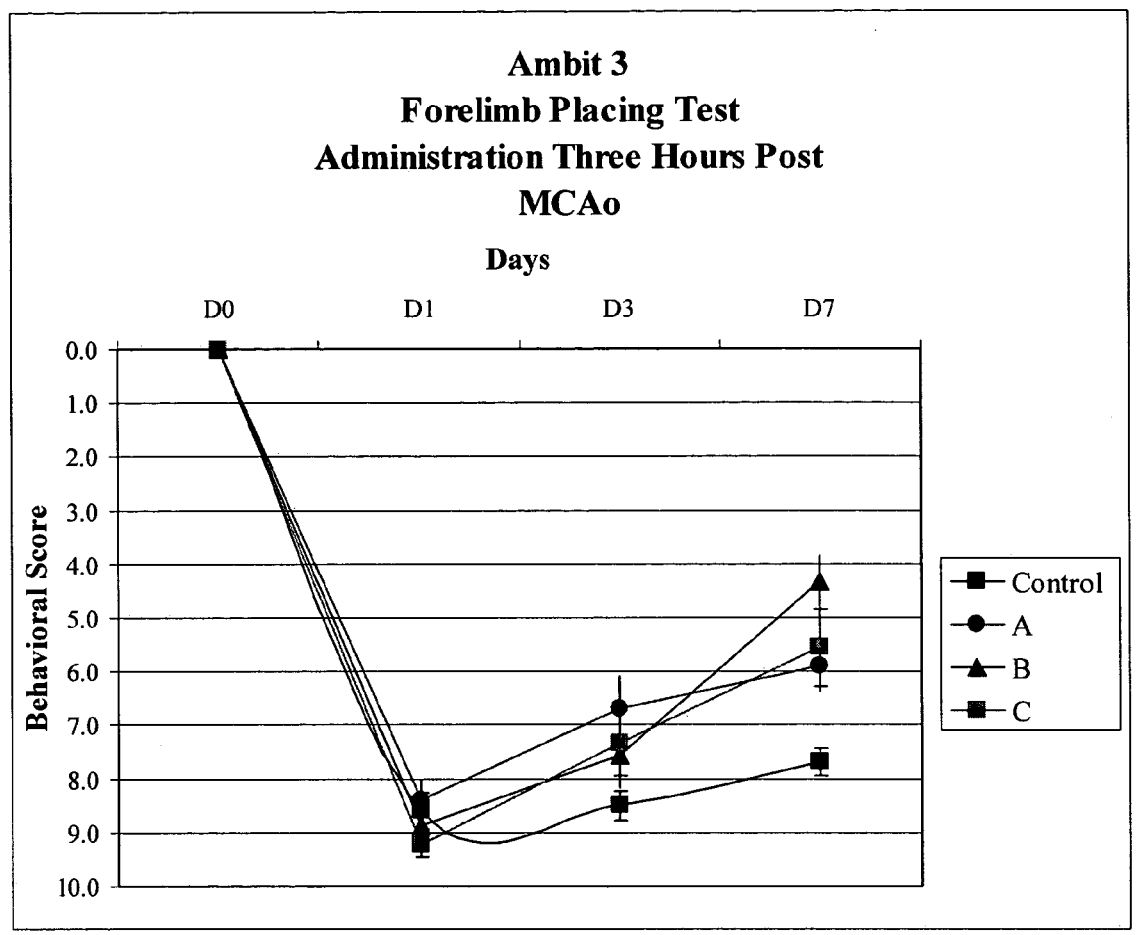
FIG. 17 shows the measured scores of the Forelimb Placing Test where the compounds of the invention were administered three hours post MCAo.

FIG. 17 provides the results of Table 6 in graph form.

Table 7 shows the measured scores of the forelimb placing tests where compounds 782236 (A), 781430 (B) and atorvastatin (C) were administered six hours after MCAo. The results show an improvement after treatment by the pyrrole compounds and atorvastatin.

TABLE 7

| | | D0 | D1 | D3 | D7 |
|---|---|---|---|---|---|
| | Control | | | | |
| AVG | | 0 | 9.1 | 8.5 | 7.2 |
| SEM | | 0 | 0.3 | 0.4 | 0.7 |
| | A | | | | |
| AVG | | 0 | 9.2 | 8.9 | 7 |
| SEM | | 0 | 0.31 | 0.43 | 0.7 |
| | B | | | | |
| AVG | | 0 | 8.9 | 8.5 | 6 |
| SEM | | 0 | 0.3 | 0.3 | 0.4 |
| | C | | | | |
| AVG | | 0 | 8.8 | 8.8 | 8 |
| SEM | | 0 | 0.4 | 0.5 | 0.3 |

Figure 18:
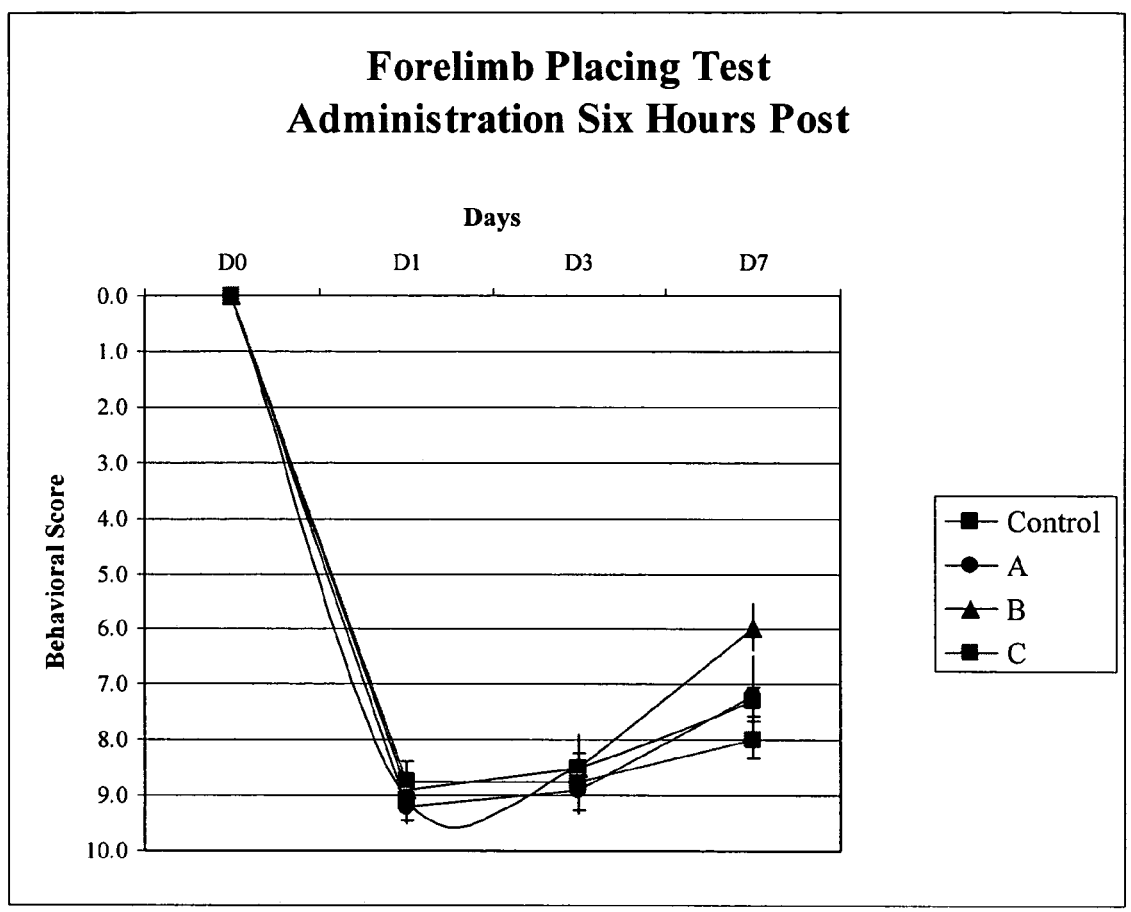
FIG. 18 shows the measured scores of the Forelimb Placing Test where the compounds of the invention were administered six hours post MCAo.

FIG. 18 provides the results of Table 7 in graph form.

Table 8 shows the measured scores of the hindlimb placing test where compounds 782236 (A), 781430 (B) and atorvastatin (C) were administered three hours after MCAo. The results show an improved effect after treatment by the pyrrole compounds and atorvastatin.

TABLE 8

| | | D0 | D1 | D3 | D7 |
|---|---|---|---|---|---|
| | Control | | | | |
| AVG | | 0 | 5.4 | 4.7 | 4.1 |
| SEM | | 0 | 0.4 | 0.4 | 0.3 |
| | A | | | | |
| AVG | | 0 | 4.6 | 4 | 3.2 |
| SEM | | 0 | 0.43 | 0.37 | 0.35 |
| | B | | | | |
| AVG | | 0 | 4.1 | 2.8 | 2.1 |
| SEM | | 0 | 0.5 | 0.1 | 0.4 |
| | C | | | | |
| AVG | | 0 | 5.6 | 4.3 | 2.8 |
| SEM | | 0 | 0.2 | 0.4 | 0.6 |

Figure 19:
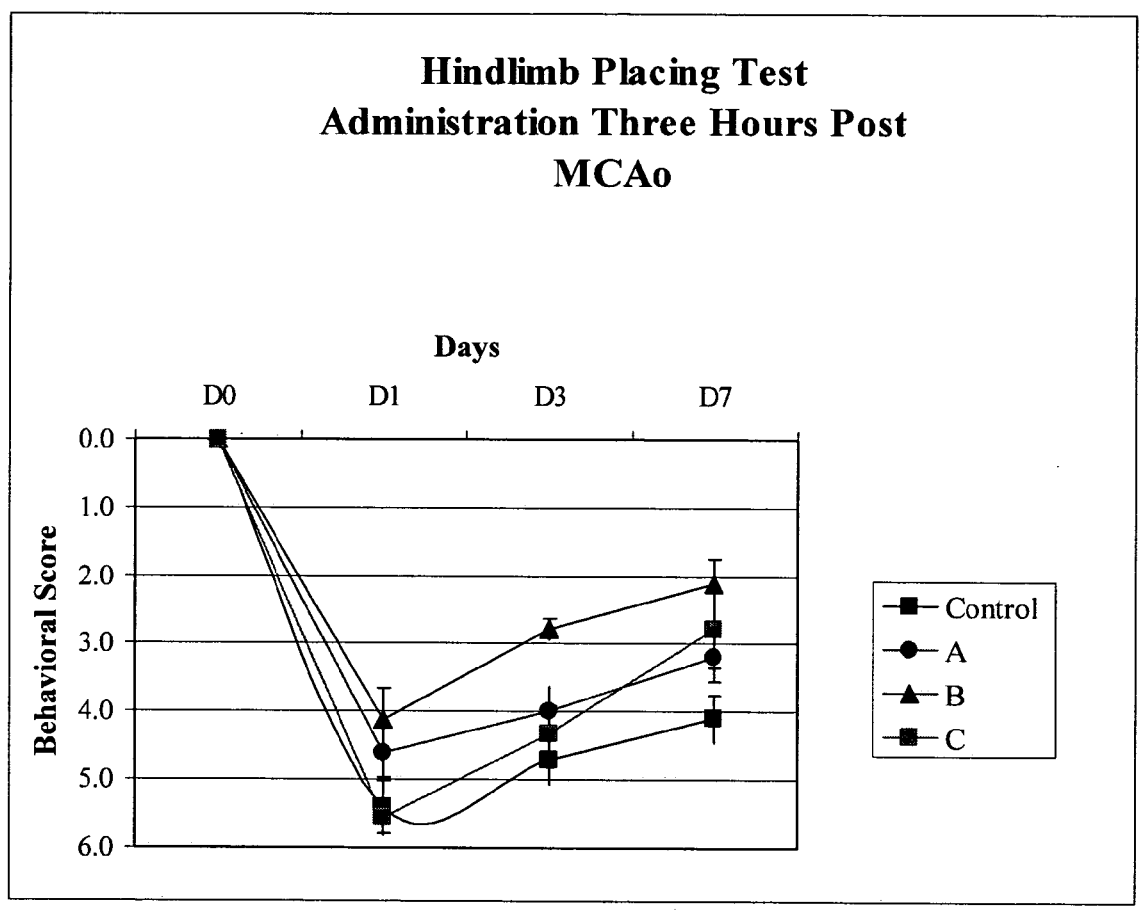
FIG. 19 shows the measured scores of the Hindlimb Placing Test where the compounds of the invention were administered three hours post MCAo.

FIG. 19 provides the results of Table 8 in graph form.

Table 9 shows the measured scores of the hindlimb placing test where compounds 782236 (A), 781430 (B) and atorvastatin (C) were administered six hours after MCAo. The results show an improvement effect after treatment by the pyrrole compounds and atorvastatin.

TABLE 9

|  | D0 | D1 | D3 | D7 |
|---|---|---|---|---|
| Control |  |  |  |  |
| AVG | 0 | 5.3 | 4.9 | 3.8 |
| SEM | 0 | 0.2 | 0.4 | 0.4 |
| A |  |  |  |  |
| AVG | 0 | 4.7 | 4 | 3.3 |
| SEM | 0 | 0.21 | 0.38 | 0.36 |
| B |  |  |  |  |
| AVG | 0 | 5.3 | 3.5 | 3 |
| SEM | 0 | 0.2 | 0.2 | 0.2 |
| C |  |  |  |  |
| AVG | 0 | 5.9 | 4.9 | 3.5 |
| SEM | 0 | 0.1 | 0.4 | 0.6 |

Figure 20:
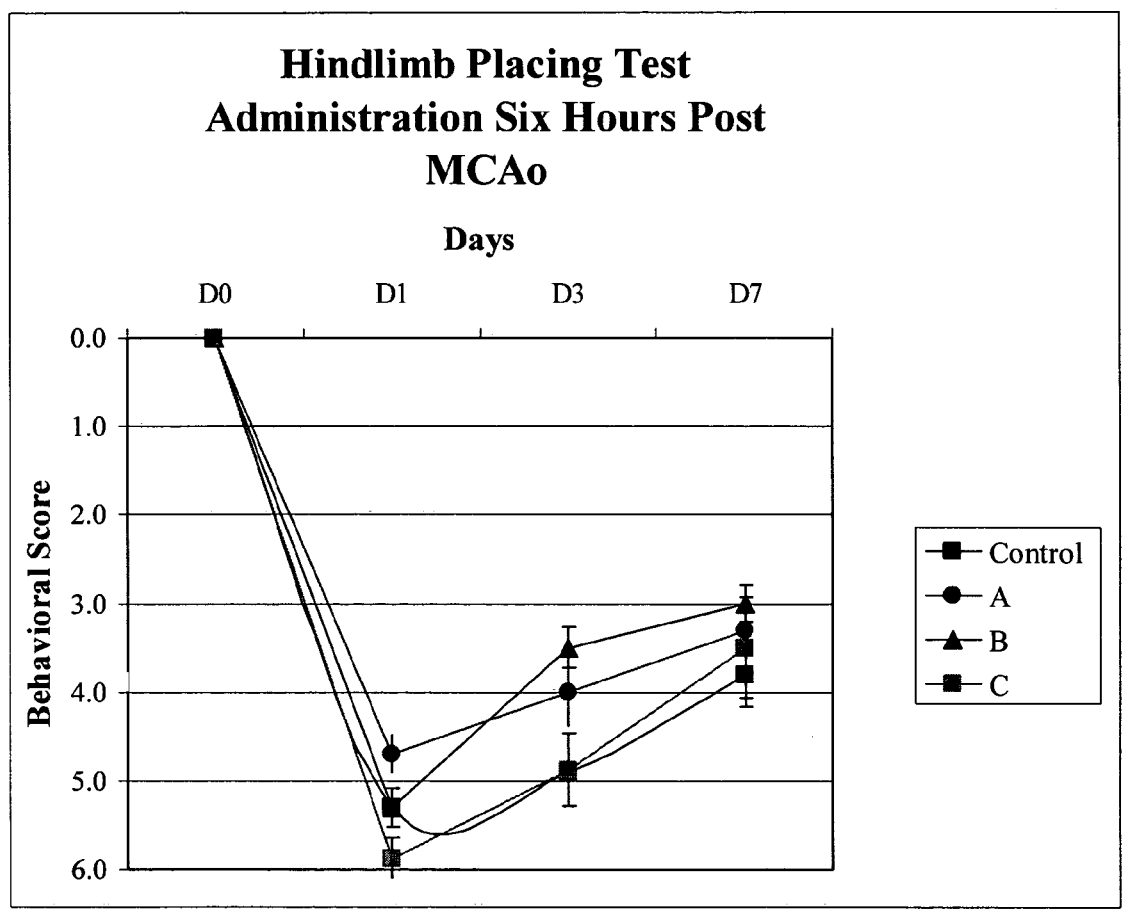
FIG. 20 shows the measured scores of the Hindlimb Placing Test where the compounds of the invention were administered six hours post MCAo.

FIG. 20 provides the results of Table 9 in graph form.

Body Swing Test. The animal was held approximately 1 inch from the base of its tail. It was then elevated to an inch above a surface of a table. The animal was held in the vertical axis, defined as no more than 10° to either the left or the right side. A swing was recorded whenever the animal moves its head out of the vertical axis to either side. Before attempting another swing, the animal must return to the vertical position for the next swing to be counted. Thirty total swings were counted. A normal animal typically has an equal number of swings to either side. Following focal stroke, the animal tends to swing to the contralateral side. There is a slow spontaneous recovery of body swing during the first month after stroke.

Table 10 shows the measured scores of the body swing test where compounds 782236 (A), 781430 (B) and atorvastatin (C) were administered three hours after MCAo. The results show an improvement after treatment by the pyrrole compounds and atorvastatin.

TABLE 10

|  | D0 | D1 | D3 | D7 |
|---|---|---|---|---|
| Control |  |  |  |  |
| AVG | 50 | 10 | 18 | 27 |
| SEM | 0 | 3 | 2 | 4 |
| A |  |  |  |  |
| AVG | 50 | 8 | 27 | 37 |
| SEM | 0 | 3 | 2 | 4 |
| B |  |  |  |  |
| AVG | 50 | 31 | 43 | 44 |
| SEM | 0 | 3 | 3 | 4 |
| C |  |  |  |  |
| AVG | 50 | 13 | 28 | 41 |
| SEM | 50 | 3 | 2 | 4 |

Figure 21:
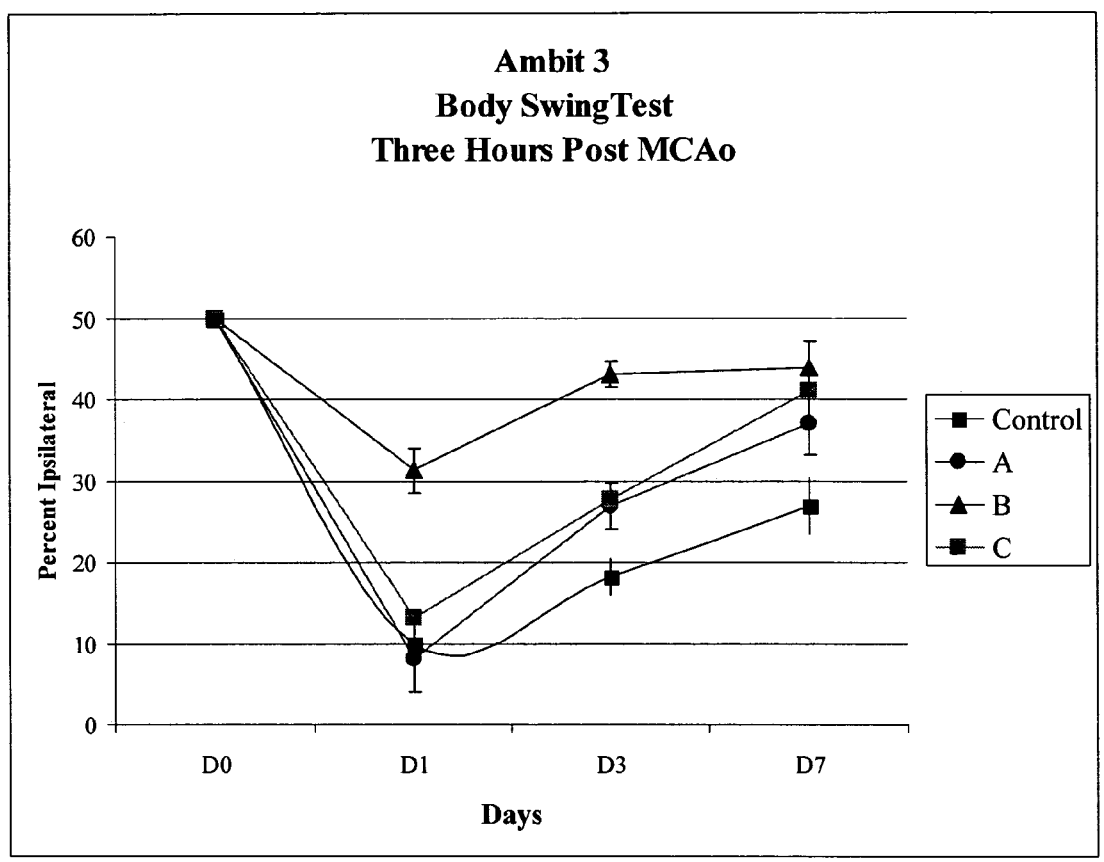
FIG. 21 shows the measured scores of the Body Swing Test where the compounds of the invention were administered three hours post MCAo.

FIG. 21 shows the results of Table 10 in graph form.

Table 11 shows the measured scores of the body swing test where compounds 782236 (A), 781430 (B) and atorvastatin (C) were administered six hours after MCAo. The results show an improvement after treatment by the pyrrole compounds and atorvastatin.

TABLE 11

|  | D0 | D1 | D3 | D7 |
|---|---|---|---|---|
| Control |  |  |  |  |
| AVG | 50 | 9 | 9 | 17 |
| SEM | 0 | 4 | 5 | 4 |
| A |  |  |  |  |
| AVG | 50 | 7 | 9 | 23 |
| SEM | 0 | 4 | 5 | 4 |
| B |  |  |  |  |
| AVG | 50 | 19 | 22 | 23 |
| SEM | 0 | 1 | 3 | 2 |
| C |  |  |  |  |
| AVG | 50 | 19 | 17 | 19 |
| SEM | 0 | 2 | 2 | 2 |

Figure 22:
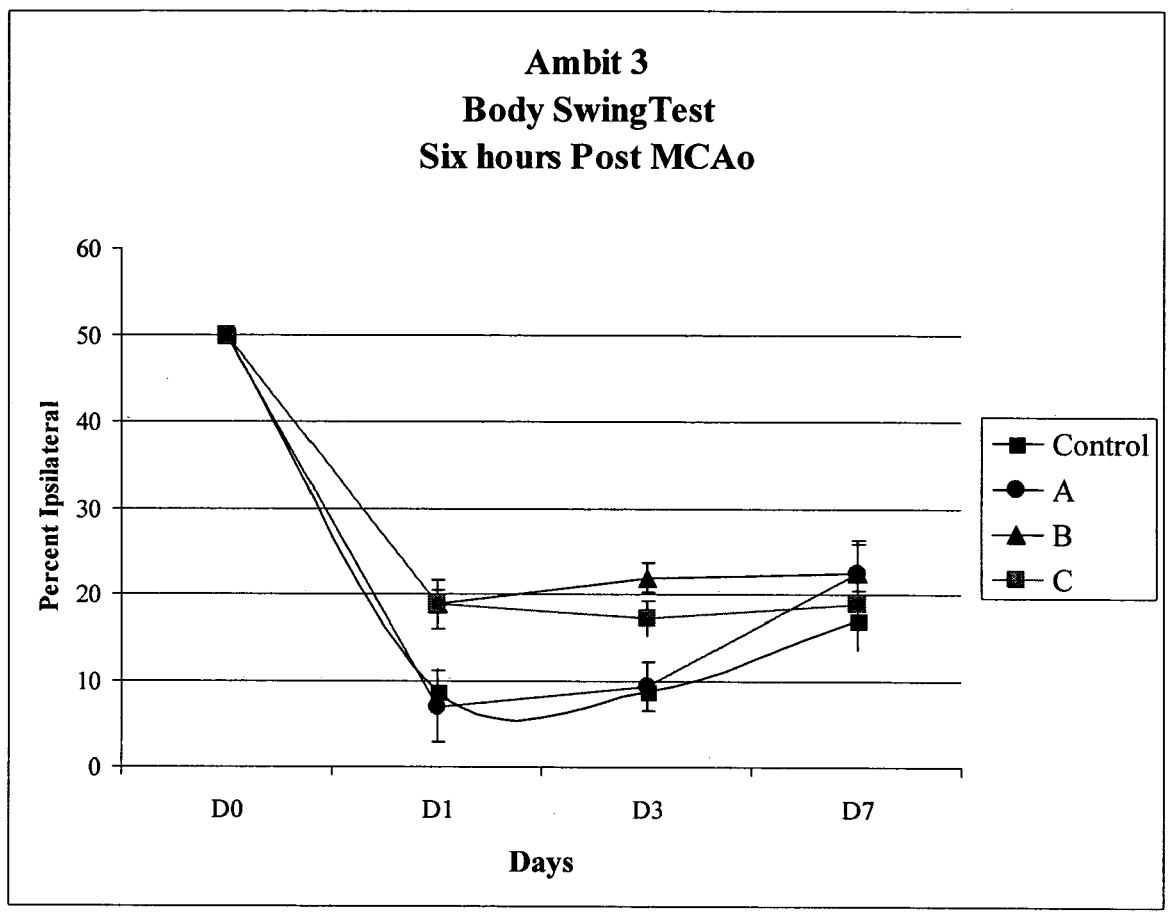
FIG. 22 shows the measured scores of the Body Swing Test where the compounds of the invention were administered six hours post MCAo.

FIG. 22 shows the results of Table 11 in graph form.

Morphometric Analysis—Brain Perfusion. Seven days after the induction of focal ischemia, rats were deeply anesthetized with a ketamine, and xylazine cocktail. The animals were then perfused transcardially with normal saline (with heparin 2 unit/ml) followed by 4% paraformaldehyde for infarct volume measurement (H&E staining). Brains were removed and stored in 10% formalin to be sectioned and stained with Hematoxylin and Eosin.

Infarct Volume Measurement. Using the Image Pro-Plus imaging system, a total of 7 images per brain of the posterior side of each slice were analyzed through digital analysis. The total direct infarct volume was calculated for the left hemisphere using the equation below. Digitizing and computation was done under blinded conditions.

$$\text{Volume (mm}^3\text{)} = \frac{\sum \text{area (mm}^2\text{) per side}}{\text{No. of sides analyzed}} \times 7 \text{ mm}$$

The total infarct volumes are calculated for each animal and subsequent group means were determined as volume of area ($mm^3$). To account for tissue shrinkage and possible edema the indirect method of infarct volume was calculated using the formula:

Total Contralateral Hemisphere Volume−Total Infarcted Hemisphere Volume ($mm^3$)

Table 12 shows the corrected infarct volume where compounds 782236 (A), 781430 (B) and atorvastatin (C) were administered three hours after MCAo. The results show an improvement after treatment by the pyrrole compounds and atorvastatin.

TABLE 12

| Corrected Infarct Volume | | | |
|---|---|---|---|
| Control | A | B | C |
| 236 | 229.2 | 180.5 | 243.8 |
| 285 | 127.9 | 224.1 | 124 |
| 264 | 222.3 | 208.1 | 162.8 |
| 152.2 | 235 | 233.4 | 164.5 |
| 213 | 139.8 | 255.3 | 218.2 |
| 347.8 | 210.9 | 200.1 | 208 |

TABLE 12-continued

| | Corrected Infarct Volume | | | |
|---|---|---|---|---|
| | Control | A | B | C |
| | 250.6 | 272.5 | 231.7 | 303.3 |
| | 256 | 275.6 | 217.7 | 262.3 |
| | 394.5 | 163.8 | 173 | 184.8 |
| | 295 | 249 | | |
| N | 10 | 10 | 9 | 9 |
| Average | 269.41 | 212.59 | 213.77 | 207.96 |
| SD | 67.73 | 52.29 | 26.31 | 55.84 |
| SEM | 21.4 | 16.5 | 8.8 | 18.6 |

Figure 23:
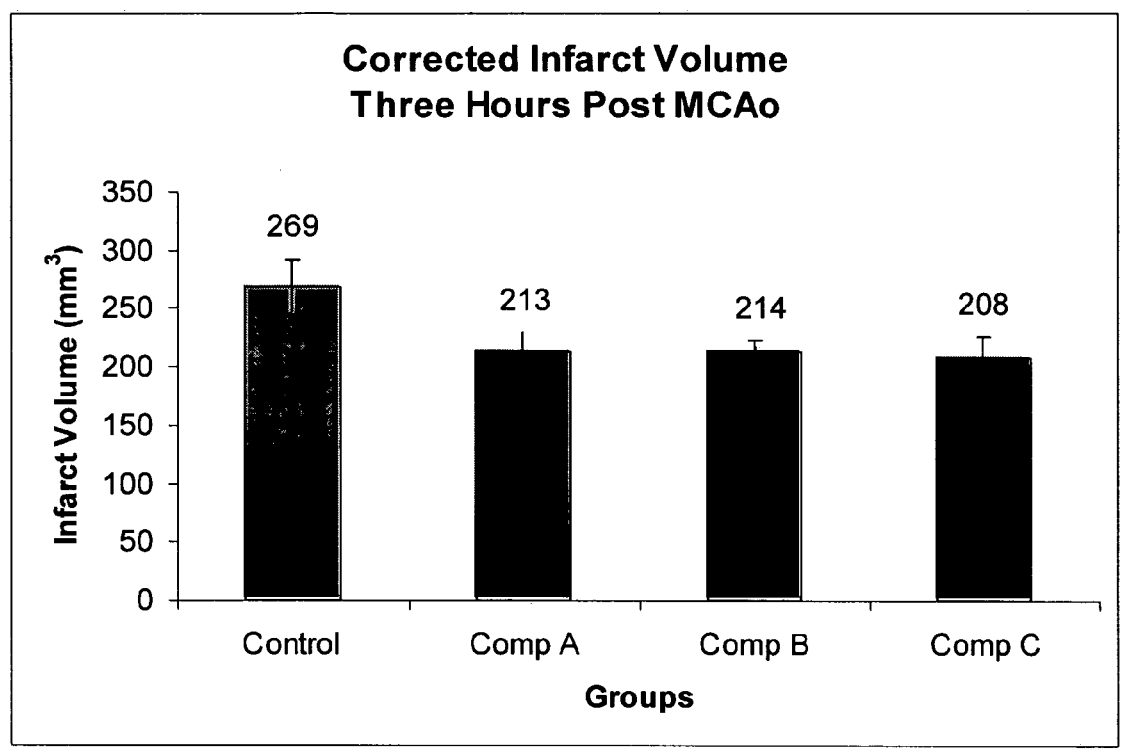
FIG. 23 shows the corrected infarct volume measurements where the compounds of the invention were administered three hours post MCAo.

FIG. 23 shows the results of Table 12 in graph form.

Table 13 shows the percent infarct volume where compounds 782236 (A), 781430 (B) and atorvastatin (C) were administered three hours after MCAo. The results show an improvement after treatment by the pyrrole compounds and atorvastatin.

TABLE 13

| | Percent Infarct Volume | | | |
|---|---|---|---|---|
| | Control | A | B | C |
| | 24.4 | 25.9 | 19.71432 | 25.43478 |
| | 34.2 | 15.9 | 23.99355 | 12.82351 |
| | 26 | 27.5 | 22.56286 | 17.39363 |
| | 17.4 | 25.4 | 24.24291 | 16.81109 |
| | 26 | 18.9 | 23.89662 | 22.80941 |
| | 33.6 | 25.1 | 19.73737 | 18.35168 |
| | 27.8 | 29 | 21.5679 | 28.19637 |
| | 29.2 | 23.7 | 24.30045 | 30.99993 |
| | 40.1 | 15.8 | 20.61765 | 16.2101 |
| | 32.5 | 28.1 | | |
| N | 10 | 10 | 9 | 9 |
| Average | 29.12 | 23.53 | 22.29 | 21 |
| SD | 6.32 | 4.92 | 1.93 | 6.15 |
| SEM | 2 | 1.6 | 0.6 | 2 |

Figure 24:
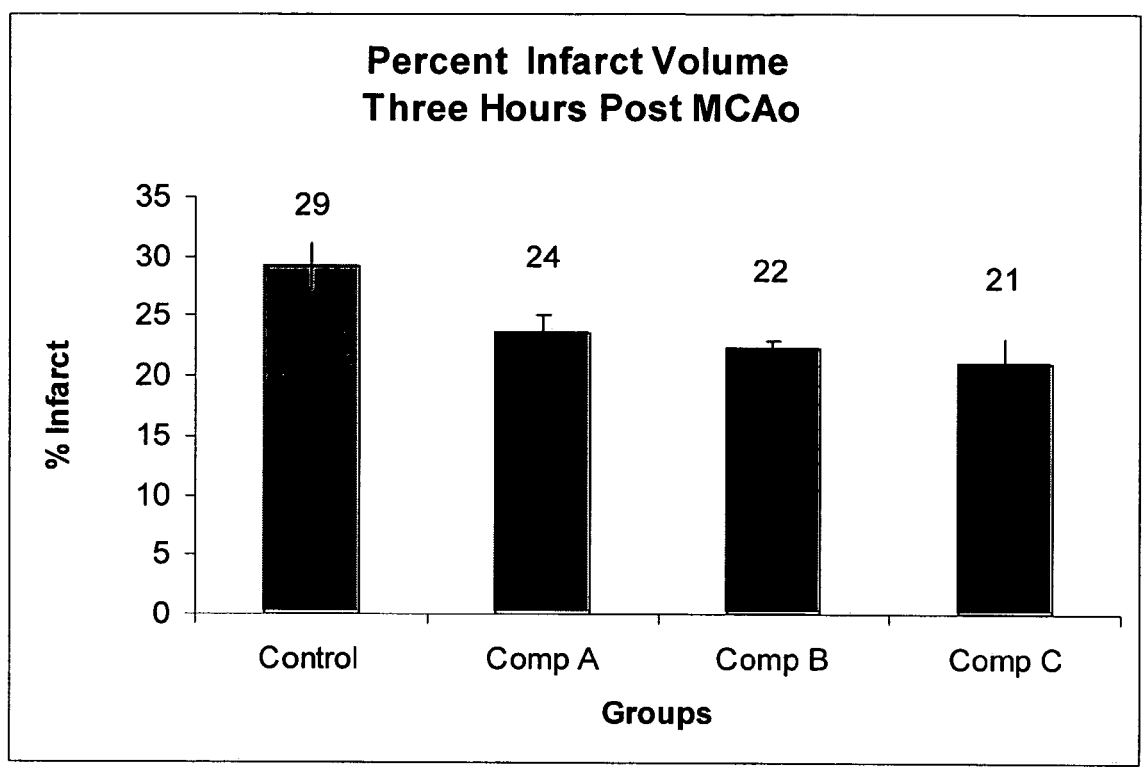
FIG. 24 shows the percent infarct volume measurements where the compounds of the invention were administered three hours post MCAo.

FIG. 24 shows the results of Table 13 in graph form.

Table 14 shows the corrected infarct volume where compounds 782236 (A), 781430 (B) and atorvastatin (C) were administered six hours after MCAo. The results show an improvement after treatment by the pyrrole compounds and atorvastatin.

TABLE 14

| | Corrected Infarct Volume | | | |
|---|---|---|---|---|
| | Control | A | B | C |
| | 242.1 | 215.8 | 352.4 | 333 |
| | 310.8 | 229 | 289.9 | 214.3 |
| | 361.3 | 213.3 | 195.4 | 291.6 |
| | 255 | 271.4 | 327.7 | 338.3 |
| | 241.1 | 316 | 276.5 | 354.3 |
| | 342.5 | 227.2 | 375.7 | 138.8 |
| | 380.9 | 166.6 | 204.5 | 267.1 |
| | 221.4 | 234.6 | 353.2 | 232.3 |
| | 243.2 | 269.8 | 262.2 | |
| | 262.2 | 249 | 196.6 | |
| N | 10 | 10 | 10 | 8 |
| Average | 286.04 | 239.27 | 283.4 | 271.2 |
| SD | 57.69 | 40.44 | 68.43 | 73.64 |
| SEM | 18.2 | 12.8 | 21.6 | 26 |

Figure 25:
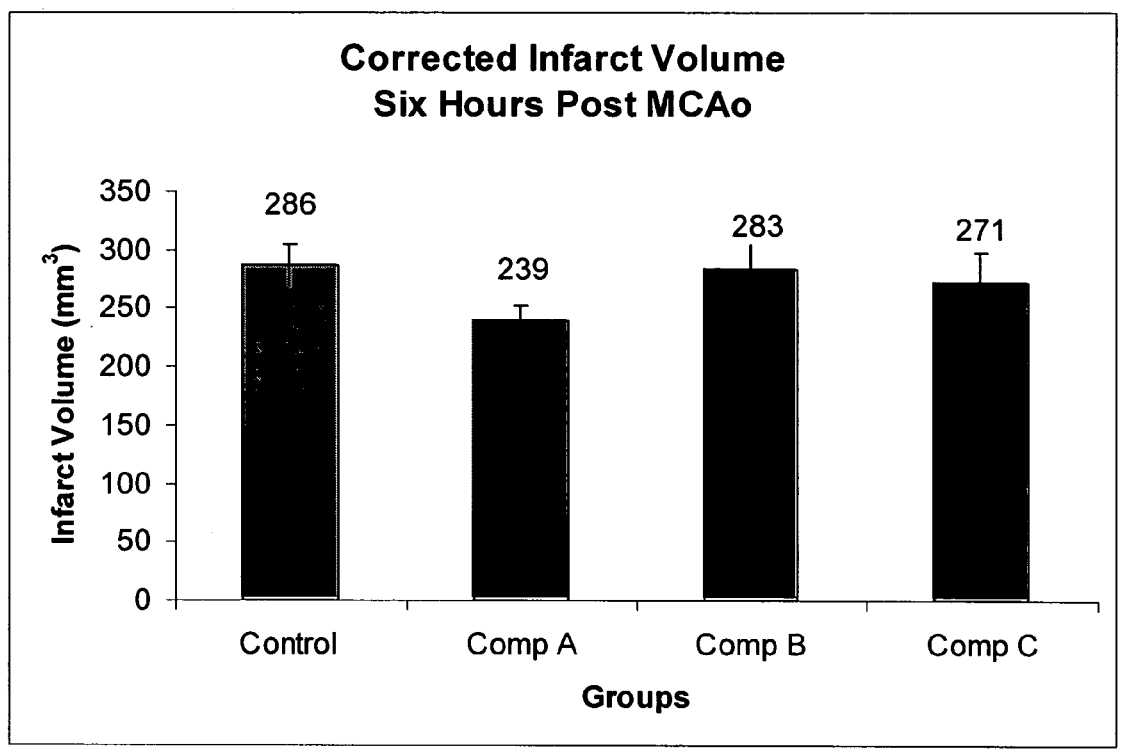
FIG. 25 shows the corrected infarct volume measurements where the compounds of the invention were administered six hours post MCAo.

FIG. 25 shows the results of Table 14 in graph form.

Table 15 shows the percent infarct volume where compounds 782236 (A), 781430 (B) and atorvastatin (C) were administered six hours after MCAo.

TABLE 15

| | Percent Infarct Volume | | | |
|---|---|---|---|---|
| | Control | A | B | C |
| | 23.2 | 28.9 | 29.1 | 31 |
| | 33.6 | 24.8 | 28.8 | 25.4 |
| | 41.3 | 23.5 | 25.4 | 29.4 |
| | 34.2 | 25.3 | 35.3 | 25.7 |
| | 22 | 25.8 | 21.8 | 26.6 |
| | 31.6 | 25.6 | 31.4 | 12.7 |
| | 29.2 | 31.5 | 21.7 | 21.6 |
| | 22.3 | 24.6 | 26.2 | 24.2 |
| | 20.7 | 28.8 | 33.9 | |
| | 25.3 | 28.1 | 15.6 | |
| N | 10 | 10 | 10 | 8 |
| Average | 28.36 | 26.69 | 26.92 | 24.56 |
| SD | 6.74 | 2.49 | 6.07 | 5.62 |
| SEM | 2.1 | 0.8 | 1.9 | 2 |

Figure 26:
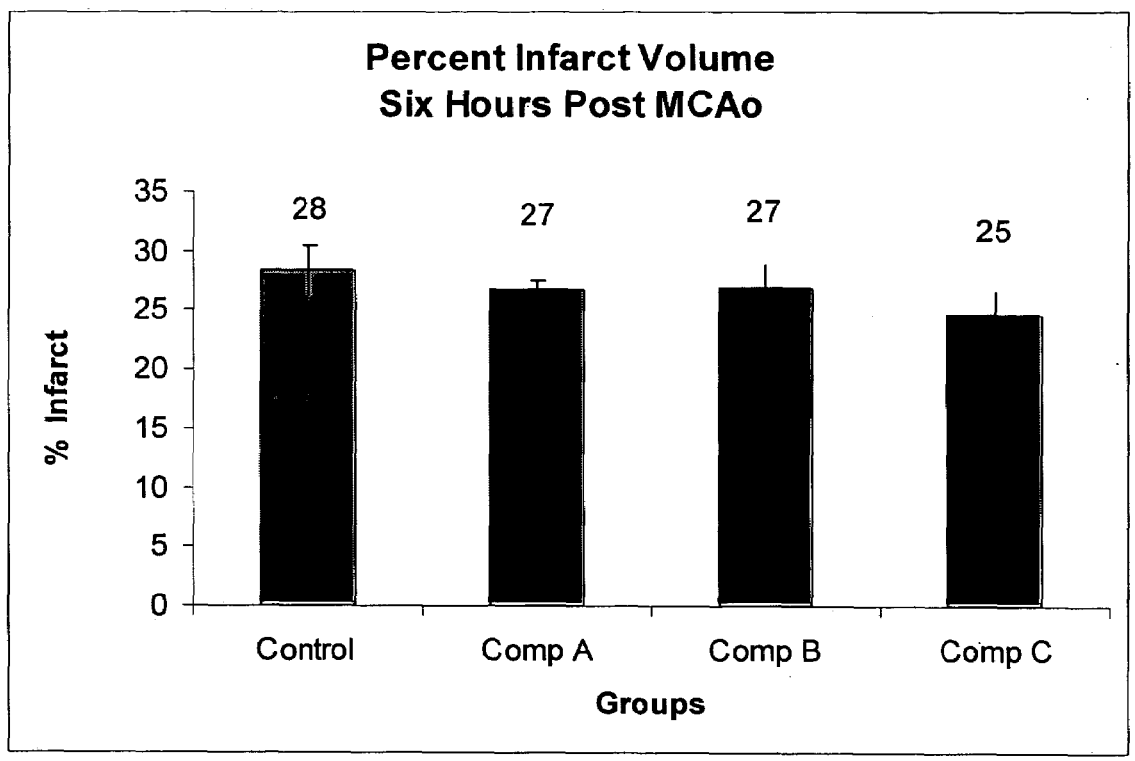
FIG. 26 shows the percent infarct volume measurements where the compounds of the invention were administered three hours post MCAo.

FIG. 26 shows the results of Table 15 in graph form.

Body Temperature and Weight. All animals' body temperature were monitored throughout the surgery and maintained near normal values (37-38° C.). Animal's body weights were measured and documented before surgery and at the end of the study immediately before euthanation.

Clinical Observations. Along with the behavioral assessment animals were observed daily for abnormal behavior, including but not limited to circling, lethargy, respiratory wheezing or discharge, hair loss, and early death. All abnormalities were recorded. Likewise, normal behavior was also noted as normal.

Statistical Analysis. Behavioral scores and body weight were analyzed by two-way repeated measures analysis of variance (ANOVA; treatment X time). Infarct volume was analyzed by one-way ANOVA. A p value of $\leq 0.05$ is considered a statistically significant difference.

Experimental Design

Experimental Groups and Compound Administration. A total of 80 animals underwent MCAo using subcutaneous administration of all test articles, according to the experimental design illustrated in Table 16. Three compounds 782236, 781430 and atorvastatin, at predetermined doses were compared to vehicle and assigned to two different time schedules of administration relative to the time of MCAo. The time schedules for administration of all treated groups (10 animals/group) was divided as follows:

a. 3 hrs, 6 hrs, & 25 hrs and days 2-7 b.i.d. post
b. 6 hrs, 9 hrs & 25 hrs and days 2-7 b.i.d. post All animals were treated with the compound(s)/vehicle(s) as a blinded random investigation. The dose and route of administration is given below in Table 16. Forty animals used in the first group of the study (group a.) Cerebral blood flow measurement was performed according to the protocol previously discussed on days 0, 1 and 5 with respect to MCAo.

TABLE 16

| Compound Administration | | | | | |
|---|---|---|---|---|---|
| | | Schedule/Dosage | | | |
| Compound | Route | Day 1 | | | Days 2-7 |
| | | post3 | post6 | post24 | b.i.d. |
| 782236 | IV-cath | 2 mg/kg | 1 mg/kg | 1 mg/kg | 1 mg/kg |
| 781430 | IV-cath | 2 mg/kg | 1 mg/kg | 1 mg/kg | 1 mg/kg |
| Atorvastatin | IV-cath | 2 mg/kg | 1 mg/kg | 1 mg/kg | 1 mg/kg |

TABLE 16-continued

Compound Administration

| | | Schedule/Dosage | | | |
|---|---|---|---|---|---|
| Compound | Route | Day 1 | | | Days 2-7 |
| | | post6 | post9 | post24 | b.i.d. |
| 782236 | IV-cath | 2 mg/kg | 1 mg/kg | 1 mg/kg | 1 mg/kg |
| 781430 | IV-cath | 2 mg/kg | 1 mg/kg | 1 mg/kg | 1 mg/kg |
| Atorvastatin | IV-cath | 2 mg/kg | 1 mg/kg | 1 mg/kg | 1 mg/kg |

Outline for the Experimental Design

Animal: 80 male Sprague Dawley Rats, 300-350 g (to arrive 7 days before surgery at 230-250 g); Groups, Dosing Schedule:

| | |
|---|---|
| 10 * AB30087 | I.V. 3 hr, 6 hr, 24 hr and days 2-7 b.i.d. post |
| 10 * AB30000 | I.V. 3 hr, 6 hr, 24 hr and days 2-7 b.i.d. post |
| 10 * AB0089 | I.V. 3 hr, 6 hr, 24 hr and days 2-7 b.i.d. post |
| 10 * Vehicle (1 ml/kg) | I.V. 3 hr, 6 hr, 24 hr and days 2-7 b.i.d. post |
| 10 * AB30087 | I.V. 6 hr, 9 hr, 24 hr and days 2-7 b.i.d. post |
| 10 * AB30000 | I.V. 6 hr, 9 hr, 24 hr and days 2-7 b.i.d. post |
| 10 * AB0089 | I.V. 6 hr, 9 hr, 24 hr and days 2-7 b.i.d. post, |
| 10 * Vehicle (1 ml/kg) | I.V. 6 hr, 9 hr, 24 hr and days 2-7 b.i.d. post |

Schedule:

| | |
|---|---|
| Day 0 | MCAo Tamura model/Blood Flow monitoring Behavioral Assessment |
| Day 1 | Behavioral Assessment/Cerebral Blood Flow monitoring |
| Day 3 | Behavioral Assessment |
| Day 5 | Cerebral Blood Flow monitoring |
| Day 7 | Behavioral Assessment Brain perfusion prep for H&E staining |

Example 12

Neuroprotection Assay $4 \times 10^5$ rat cortex cells were cultured in a poly-D-lysine coated 24-well plate in Neurobasal medium supplemented with 2 mM glutamine, 100 units/ml penicillin-streptomycin and B27 supplement at 37° C. in 5% $CO_2$. After 12-14 days of culture the cells were pre-incubated in 10 μM compound or vehicle for 1.5 hours in standard medium (final concentration of DMSO vehicle was 1%). NMDA in PBS was added to each well to a final concentration of 300 μM for ten minutes. The cells were subsequently washed three times in standard medium, and medium+10 μM compound was placed back on the cells. After 24 hours at 37° C. in 5% $CO_2$, 100 μl of medium was used for lactate dehydrogenase (LDH) detection with the Cytotoxicity Detection Kit (LDH) (Roche). Test samples were normalized relative to total LDH release in the vehicle control.

Figure 27:
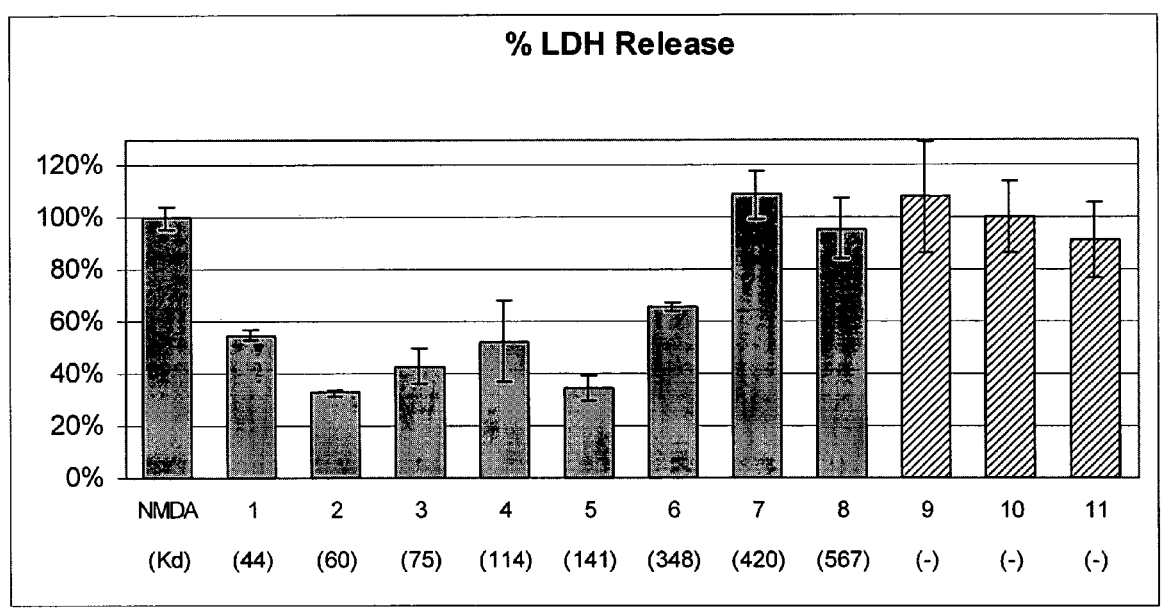
FIG. 27 shows the results of an experiment showing the effect of the compounds described herein on the percentage of lactate dehydrogenase (LDH) released, which is indicative of relative neuron cell death.

FIG. 27 shows the result that the percent of LDH released indicates relative neuron cell death. Values are normalized to vehicle control as 100% of neuronal cell death, and average percent LDH release in the presence of compounds is indicated. A decrease in LDH release indicates decreased neuronal cell death. The compound ID is indicated immediately beneath the chart, and the Kd of each compound for the target is indicated in parenthesis. The three compounds indicated by hatches do not interact with the target, and are negative controls.

| | |
|---|---|
| 1 = | 780520 |
| 2 = | 780858 |
| 3 = | 781430 |
| 4 = | 780702 |
| 5 = | 780936 |
| 6 = | 779974 |
| 7 = | 782756 |
| 8 = | 781456 |
| 9 = | 780390 |
| 10 = | 780832 |
| 11 = | 780962 |

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

The invention claimed is:

1. A pyrrole compound having the formula:

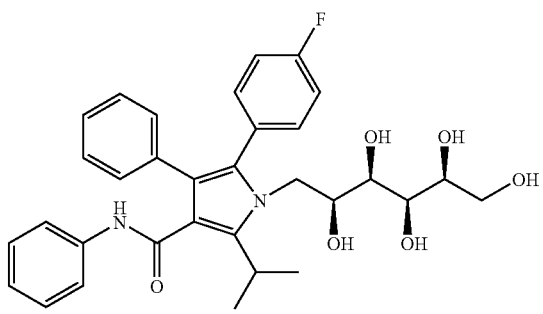

or a diastereomer, enantiomer, or pharmaceutically acceptable salt thereof.

2. A pharmaceutical composition comprising a compound of claim 1 and a pharmaceutically acceptable excipient.

3. A method of treating stroke comprising administering to a subject in need thereof an effective amount of a compound of claim 1.

4. The method of claim 3, wherein the method is for treating post stroke trauma.

5. A method for treating trauma associated with stroke comprising administering to a subject in need thereof an effective amount of a compound of claim 1 after said stroke.

6. The method of claim 5, wherein said compound is administered within the first 48 hours of the onset of symptoms.

7. The method of claim 5, wherein said compound is administered within the first 6 hours of the onset of symptoms.

8. The method of claim 5, wherein said compound is administered within the first 3 hours of the onset of symptoms.

9. The method of claim 5, wherein said compound is administered via intravenous injection, bolus injection, a pill, a capsule, transdermal patch or buccal delivery.

10. A kit comprising a carrier, package or container, wherein said carrier, package or container(s) comprises a compound of formula:

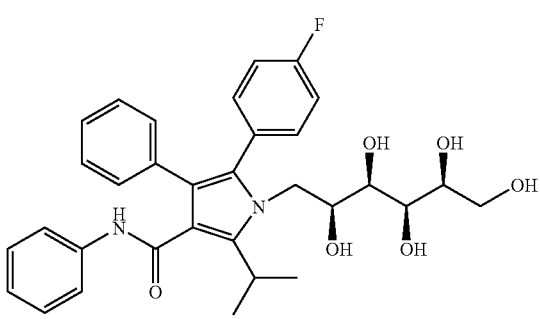

or a diastereomer, enantiomer, or pharmaceutically acceptable salt thereof, and wherein said kit optionally comprises one or more additional containers, each said container comprising one or more reagents or materials.

11. The kit of claim 10, wherein said containers are selected from bottles, vials, syringes and test tubes.

12. The kit of claim 10, wherein said materials are selected from buffers, diluents, filters, needles, syringes, carrier, package, container, vial and instructions for use.

13. The compound of claim 1, wherein the compound is

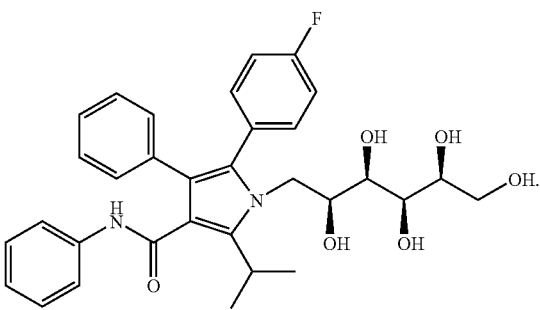

14. The compound of claim 1, wherein the compound is a diastereomer of the compound of formula

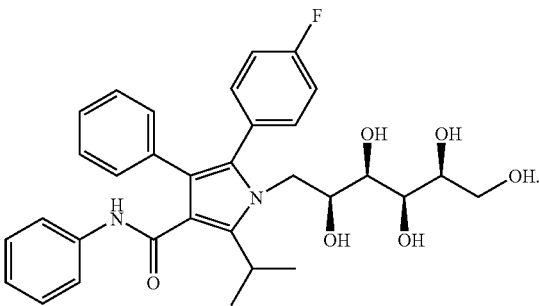

15. The compound of claim 1, wherein the compound is an enantiomer of the compound of formula

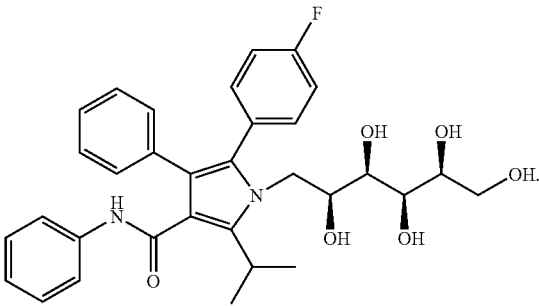

16. The compound of claim 1, wherein the compound is a pharmaceutically acceptable salt of the compound of formula

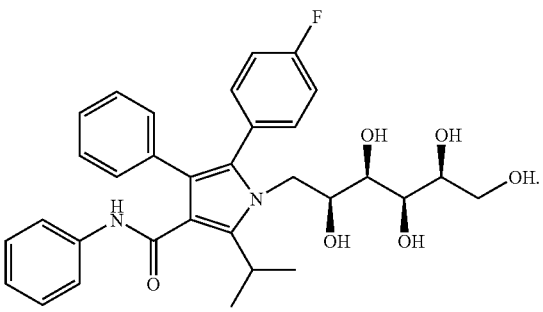

* * * * *